US008039688B2

(12) United States Patent
Hanley-Bowdoin et al.

(10) Patent No.: US 8,039,688 B2

(45) Date of Patent: Oct. 18, 2011

(54) GEMINIVIRUS RESISTANT TRANSGENIC PLANTS

(75) Inventors: Linda Hanley-Bowdoin, Raleigh, NC (US); Beverly Orozco, Raleigh, NC (US); Wilhelm Gruissem, Forch (CH)

(73) Assignees: North Carolina State University, Raleigh, NC (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 12/433,085

(22) Filed: Apr. 30, 2009

(65) Prior Publication Data

US 2009/0229013 A1 Sep. 10, 2009

Related U.S. Application Data

(63) Continuation of application No. 11/936,622, filed on Nov. 7, 2007, now abandoned, which is a continuation of application No. 10/633,850, filed on Aug. 4, 2003, now abandoned, which is a continuation-in-part of application No. 09/289,346, filed on Apr. 9, 1999, now Pat. No. 6,800,793.

(60) Provisional application No. 60/125,004, filed on Mar. 18, 1999.

(51) Int. Cl.

| | |
|---|---|
| ***C12N 15/82*** | (2006.01) |
| ***C12N 15/86*** | (2006.01) |
| ***A01H 1/00*** | (2006.01) |
| ***C07H 21/04*** | (2006.01) |

(52) U.S. Cl. ...................... 800/279; 800/278; 536/23.72

(58) Field of Classification Search ........................ None
See application file for complete search history.

(56) References Cited

U.S. PATENT DOCUMENTS 5,850,023 A 12/1998 Elmer et al. .................. 800/205

FOREIGN PATENT DOCUMENTS

| | | |
|---|---|---|
| WO | WO 97/39110 | 10/1997 |
| WO | WO 97/42315 | 11/1997 |
| WO | WO 97/42316 | 11/1997 |

OTHER PUBLICATIONS

Hong et al. 1996, MPMI 9:219-225.*
Hong et al. 1993, Journal of General Virology 74:2437-2443.*
Desbiez et al. 1995, PNAS 92:5640-5644.
Kong et al. "A geminivirus replication protein interacts with the retinoblastoma protein through a novel domain to determine symptoms and tissue specificity of infection in plants" *The EMBO Journal*, 19(13), pp. 3485-3495, 2000.
Hong, Yiguo, et al., Virus Resistance in *Nicatiana benthamiana* Conferred by African Cassava Mosaic Virus Replication-Associated Protein (AC1) Transgene, *MMPI*, vol. 9, No. 4, pp. 219-225 (May 1996).
Hanson, Stephen F., et al., Mutational Analysis of a Putative NTP-Binding Domain in the Replication-Associated Protein (AC1) of Bean golden Mosaic Geminivirus, *Virology*, vol. 211, No. 1, pp. 1-9 (Aug. 1, 1995).
International Search Report PCT/US00/06759; dated Aug. 15, 2000.
Hartl, D. *Genetics* 3rd edition, Jones & Bartlett Publishers, Boston, p. 213 (1994).
Durfee at al. "Retinoblastoma-Related Proteins in Plants: Homologues or Orthologues of their Metazoan Counterparts" *Plant Molecular Biology* 43:635-642 (2000).
Dahiya et al. "Role of the LXCXE Binding Site in Rb Function" *Molecular and Cellular Biology* 20:6799-6805 (2000).
Ach et al. "RRB1 and RRB2 Encode Maize Retinoblastoma-Related Proteins That Interact with a Plant D-Type Cyclin and Geminivirus Replication Protein" *Molecular and Cellular Biology* 17(9):5077-5086 (1997).
Orozco et al. "The Multifuncitonal Character of a Geminivirus Replication Protein is Reflected by Its Complex Oligomerization Properties" *Journal of Biological Chemistry* 275(9) 6114-6122 (2000).
Noris et al. "Resistance to Tomato Yellow Leaf Curl Geminivirus in *Nicotiana benthamiana* Plants Transformed with a Truncated Viral C1 Gene" *Virology* 224:130-138 (1996).
Picksley and Lane "P53 and Rb: Their Celular Roles" *Curr. Op. Cell. Biol.* 6:853-858 (1994).
Williams et al. "The Retinoblastoma Protein—A Bridge to Heterochromatin" *Trends in Plant Science* 5(6):239-240 (2000).
Gutierrez, Crisanto "Geminiviruses and the Plant Cell Cycle" *Plant Molecular Biology* 43:763-772 (2000).
Hong et al. 1993, Journal of General Virology 74:2437-2443.
Hong et al. 1996, MPMI 9:219-225.
Alignment of ICMV vs. Seq ID No. 101, 1993.

* cited by examiner

*Primary Examiner* — Li Zheng

(74) *Attorney, Agent, or Firm* — Myers Bigel Sibley & Sajovec, P.A.

(57) ABSTRACT

Transgenic plants with increased resistance to geminivirus infection, and nucleic acid constructs useful in producing such plants, are described. In addition, methods of making the transgenic plants of the present invention are included. The transgenic plants express a mutant AL1/C1 geminivirus protein, which increases resistance to infection by at least one geminivirus, compared to a non-transformed control plant.

15 Claims, 11 Drawing Sheets

FIGURE 1

TGMV Rep, amino acids 110-179:
TLVWGEFQVD GRSARGGCQT SNDAAAEALN ASSKEEALQI IREKIPEKYL FQFHNLNSNL DRIFDKTPEP (SEQ ID NO:2)

Ala 1 mutant:
TLVWGEFQVD GAAAAGGCQT SNDAAAEALN ASSKEEALQI IREKIPEKYL FQFHNLNSNL DRIFDKTPEP (SEQ ID NO:3)

Ala5 mutant:
TLVWGEFQVD GRSARGGCQT SNDAAAEALN ASSAAAALQI IREKIPEKYL FQFHNLNSNL DRIFDKTPEP (SEQ ID NO:15)

Ala4+5 mutant:
TLVWGEFQVD GRSARGGCQT SNDAAAAALA ASSAAAALQI IREKIPEKYL FQFHNLNSNL DRIFDKTPEP (SEQ ID NO:4)

Ala6 mutant:
TLVWGEFQVD GRSARGGCQT SNDAAAEALN ASSKEEALQI IAAAIPEKYL FQFHNLNSNL DRIFDKTPEP (SEQ ID NO:5)

Ala7 mutant:
TLVWGEFQVD GRSARGGCQT SNDAAAEALN ASSKEEALQI IREKIPAAAL FQFHNLNSNL DRIFDKTPEP (SEQ ID NO:6)

Ala8 mutant:
TLVWGEFQVD GRSARGGCQT SNDAAAEALN ASSKEEALQI IREKIPEKYL FAFAALNSNL DRIFDKTPEP (SEQ ID NO:7)

Ala9 mutant:
TLVWGEFQVD GRSARGGCQT SNDAAAEALN ASSKEEALQI IREKIPEKYL FQFHNLNSAL AAIFDKTPEP (SEQ ID NO:8)

Ala13 mutant:
TLVWGEAAVD GRSARGGCQT SNDAAAEALN ASSKEEALQI IREKIPEKYL FQFHNLNSNL DRIFDKTPEP (SEQ ID NO:9)

Ala14 mutant:
TLVWGEFQVA GRSARGGCQT SNDAAAEALN ASSKEEALQI IREKIPEKYL FQFHNLNSNL DRIFDKTPEP (SEQ ID NO:10)

Leu mutant:
TLVWGEFQVD GRSARGGCQT SNDLLLEALN ASSKEEALQI IREKIPEKYL FQFHNLNSNL DRIFDKTPEP (SEQ ID NO:11)

wt
wt
E-N139
KEE145
REK153
EKY158
Q-HN164
N-DR172
K-E179
GST-AL1
AL1
GST
GST-AL1
AL1
GST

AL1
GST-AL1119-180
GST
AL1
GST-AL1119-180
GST
1 2 3 4 5 6 7 8 9 input
bound
GST-AL1
GST-AL1119-352
GST-AL11-180
AL1EKY158
GST-AL1119-180
1 2 3 4 5 6 7 8

AL1/mRb

AL1/AL1

GEMINIVIRUS RESISTANT TRANSGENIC PLANTS

RELATED APPLICATIONS

The present application is a continuation application of, and claims priority to, U.S. application Ser. No. 11/936,622, filed Nov. 7, 2007, now abandoned, which is a continuation of U.S. application Ser. No. 10/633,850, filed Aug. 4, 2003, now abandoned, which is a continuation-in-part of, and claims priority to, U.S. application Ser. No. 09/289,346, filed Apr. 9, 1999, and issued as U.S. Pat. No. 6,800,793 on Oct. 5, 2004, which claims the benefit, under 35 U.S.C. §119(e), of U.S. provisional application Ser. No. 60/125,004, filed Mar. 18, 1999, the entire contents of each of which are incorporated by reference herein.

STATEMENT OF GOVERNMENT SUPPORT

Research directed to this invention is supported in part by USDA Grant No. NRI-2001-02619. The Government has certain rights in this invention.

FIELD OF THE INVENTION

The present invention relates to transgenic plants with increased resistance to geminivirus infection, and mutants of the AL1/C1 (Rep) geminivirus protein useful for producing such plants. Methods of screening for suitable mutants are also provided.

BACKGROUND OF THE INVENTION

The geminiviruses are a large and diverse family of plant DNA viruses, with circular single-stranded (ss) DNA genomes that replicate through circular double stranded DNA intermediates. See Hanley-Bowdoin et al., *Cri. Rev. Plant Sci.* 18:71 (1999); Lazarowitz, *Crit. Rev. Plant Sci.* 11:327 (1992); Timmermans et al., *Annu. Rev. Plant Physiol.* 45:79 (1994). Viral DNA replication, which results in both single and double stranded viral DNAs in large amounts, involves the expression of only a small number of viral proteins that are involved in either replication or viral transcription. The geminiviruses appear to rely primarily on the machinery of the host to copy their genomes and express their genes, including the nuclear DNA and RNA polymerases of their plant hosts. These properties of geminiviruses are unusual among plant viruses, most of which are RNA viruses or replicate through RNA intermediates using virus-encoded replicases. Geminiviruses infect a broad variety of plants and cause significant crop losses worldwide.

Geminiviruses are subdivided on the basis of host range in either monocots or dicots, genome structure, and insect vector. Subgroup I geminiviruses (also known as Mastreviruses) are transmitted by leafhoppers and infect primarily monocots, although Subgroup I geminiviruses that infect dicots are known. Subgroup II geminiviruses (also known as Curtoviruses) are transmitted by leafhoppers and infect dicots. Subgroup III geminiviruses (also known as Begomoviruses) are transmitted by whiteflys and infect dicots. Subgroup I & II viruses have genomes comprising a single ssDNA component; Subgroup III geminiviruses typically have a bipartite genome comprising two similarly sized DNAs (usually termed A and B), as illustrated by African cassava mosaic virus (ACMV), tomato golden mosaic virus (TGMV) and potato yellow mosaic virus. However, monopartite geminiviruses that infect dicots are known, for example Tomato Yellow Leaf Curl Virus (TYLCV). The genomes of monopartite Subgroup II and III geminiviruses have an arrangement of genes similar to the AL1, AL2 and AL3 genes found on the A DNA component of bipartite Subgroup III geminiviruses.

Subgroup III viruses are also divided into "old world" and "new world" viruses, a division based on evolutionary divergence.

For successful infection of plants by bipartite geminiviruses, both the A and B genomic components are required. Sequence analysis of the two genome components reveals six open reading frames (ORFs). Four of the ORFs are encoded by DNA A and two by DNA B. On both components, the ORFs diverge from a conserved 230 nucleotide intergenic region (common region) and are transcribed bidirectionally from double stranded replicative form DNA. The ORFs are named according to genome component and orientation relative to the common region (i.e., left versus right (L/R), or virion versus complementary sense (V/C)). Certain proteins are known to be involved in the replication of viral DNA (REP genes). See, e.g., Elmer et al., *Nucleic Acids Res.* 16:7043 (1988); Hatta and Francki, *Virology* 92:428 (1979).

The A genome component contains all viral information necessary for the replication and encapsidation of viral DNA, while the B component encodes functions required for movement of the virus through the infected plant. The DNA A component of these viruses is capable of autonomous replication in plant cells in the absence of DNA B when inserted as a greater than full length copy into the genome of plant cells, or when a copy is transiently introduced into plant cells. In monopartite geminivirus genomes, the single genomic component contains all viral information necessary for replication, encapsidation, and movement of the virus.

Geminiviruses cause substantial losses among economically important crops, including tomato, bean and cucurbit. Current strategies to control geminivirus infections target the insect vectors that carry the viruses. However, the use of insecticides to control or combat a geminivirus infection can be expensive and inefficient. Additionally, insect hosts can vary in their susceptibility to available insecticides, and resistance to insecticides can develop over time. See Markham et al., *Pestic. Sci.* 42:123 (1994).

Varied approaches have been used in attempts to generate geminivirus-resistant plants, including classical breeding and transgenic approaches, with limited success. Unlike plant RNA viruses, the introduction of geminivirus sequences into transgenic plants does not confer resistance, and conversely, frequently results in the production of functional viral proteins (Hayes and Buck, *Nucleic Acids Res.* 17:10213 (1989); Hanley-Bowdoin et al., *Proc. Natl. Acad. Sci. USA* 87:1446 (1990)). Kunik et al. describes transgenic tomatoes that contain a geminivirus coat protein gene (Kunik et al., *BioTechnology* 12:500 (1994)). Expression of antisense RNAs against geminivirus replication proteins in transgenic plants reduces the level of viral DNA accumulation up to 70% (Day et al., *Proc. Natl. Acad. Sci. USA* 88:6721 (1991)), to a level that is still sufficient to confer wild type viral symptoms (Hanley-Bowdoin et al., *Plant Cell* 1:1057 (1989)). Similarly, the presence of defective-interfering replicons in transformed plants can reduce the level of viral DNA accumulation by about 70% (Frischmuth and Stanley, *Virology* 200:826 (1994)). The antisense RNAs and defective-interfering replicons function best against their cognate viruses (Bejarano et al., *Plant Mol. Biol.* 24:241 (1994)), further limiting their usefulness. Antisense RNA targeted to mRNA of the Rep protein (encoded by the C1 gene) was used to produce transgenic *Nicotiana benthamiana* plants with altered responses to TYLCV. (Bendahmane and Gronenborn, *Plant Mol. Biol.* 33:351 (1997)).

Accordingly, it is desirable to devise new strategies to control geminivirus infection.

SUMMARY OF THE INVENTION

A first aspect of the present invention is a plant comprising transformed plant cells, said transformed plant cells containing a heterologous nucleic acid construct comprising, in the 5' to 3' direction, a promoter operable in said plant cells, a nucleic acid sequence encoding a mutant AL1 protein, where said nucleic acid sequence is located downstream from said promoter and operatively associated therewith, and comprising a mutation in the Rb binding region, whereby binding of said mutant AL1 protein to a plant Rb protein is reduced compared to binding which would occur in the presence of a wild-type AL1 protein; and a mutation in the AL1 protein, whereby said mutant AL1 protein suppresses viral replication compared to that which would occur in the presence of a wild-type AL1 protein; and a termination sequence positioned downstream from said nucleic acid sequence and operatively associated therewith, wherein expression of said mutant AL1 protein increases resistance of said plant to infection by at least one geminivirus, compared to a non-transformed control.

A further aspect of the present invention is a method of making a transgenic plant having increased resistance to geminivirus infection. The method comprises providing a plant cell capable of regeneration; transforming the plant cell with a DNA construct comprising, in the 5' to 3' direction, (a) a promoter operable in said plant cell, (b) a nucleic acid sequence encoding a mutant AL1 protein, said nucleic acid sequence located downstream from said promoter and operatively associated therewith, and comprising i) a mutation in the Rb binding region, whereby binding of said mutant AL1 protein to a plant Rb protein is reduced compared to binding which would occur in the presence of a wild-type AL1 protein; and ii) a mutation in the AL1 protein, whereby said mutant AL1 protein suppresses viral replication compared to that which would occur in the presence of a wild-type AL1 protein; and (c) a termination sequence positioned downstream from said nucleic acid sequence and operatively associated therewith; and then regenerating a transgenic geminivirus-resistant plant from said transformed plant cell, wherein expression of said mutant AL1 protein increases resistance of said plant to infection by at least one geminivirus, compared to a non-transformed control.

A further aspect of the present invention is a nucleic acid construct comprising an expression cassette, which construct comprises, in the 5' to 3' direction, a promoter operable in a plant cell, a nucleic acid sequence encoding a mutant AL1 protein, said nucleic acid sequence located downstream from said promoter and operatively associated therewith, and comprising a mutation in the Rb binding region, whereby binding of said mutant AL1 protein to a plant Rb protein is reduced compared to binding which would occur in the presence of a wild-type AL1 protein; and ii) a mutation in the AL1 protein, whereby said mutant AL1 protein suppresses viral replication compared to that which would occur in the presence of a wild-type AL1 protein; and a termination sequence positioned downstream from said nucleic acid sequence and operatively associated therewith.

A further aspect of the present invention is a method of producing nucleic acid constructs useful in conferring increased geminivirus-resistance to plants, comprising, screening mutants of a geminivirus AL1 protein to identify mutations that suppress the ability of the AL1 protein to bind to a plant Rb protein; preparing a nucleic acid molecule encoding an AL1 protein having said mutation, and further having a mutation that suppresses geminivirus replication compared to that which would occur in the presence of a wild-type AL1 protein; and preparing a nucleic acid construct comprising, in the 5' to 3' direction, a promoter operable in a plant cell, a nucleic acid sequence encoding said mutant AL1 protein, said nucleic acid sequence located downstream from said promoter and operatively associated therewith, and a termination sequence positioned downstream from said nucleic acid sequence and operatively associated therewith.

A further aspect of the present invention is a nucleic acid construct comprising an expression cassette, which construct comprises, in the 5' to 3' direction: a promoter operable in a plant cell, a nucleic acid sequence encoding a mutant AL1 protein, said nucleic acid sequence located downstream from said promoter and operatively associated therewith, and comprising: a mutation in the oligomerization domain, whereby binding of said mutant AL1 protein to wild type AL1 protein is reduced compared to binding which would occur with a wild-type AL1 protein; and a mutation in the AL1 protein, whereby said mutant AL1 protein suppresses viral replication compared to that which would occur in the presence of a wild-type AL1 protein; and a termination sequence positioned downstream from said nucleic acid sequence and operatively associated therewith.

The present invention further provides a plant comprising transformed plant cells, said transformed plant cells comprising a heterologous nucleic acid construct encoding a mutant AL1 protein, wherein said heterologous nucleic acid construct comprises a nucleotide sequence such as SEQ ID NO:40 (K144), SEQ ID NO:41 (E145), SEQ ID NO:42 (E146), SEQ ID NO:43 (EE146), SEQ ID NO:44 (A147Y), SEQ ID NO:45 (L148), SEQ ID NO:46 (L148V), SEQ ID NO:47 (L148V*), SEQ ID NO:48 (L148G), SEQ ID NO:106 (L145A), and SEQ ID NO:49 (II151) or any combination thereof. The plant of this invention can further comprise a nucleotide sequence such as SEQ ID NO:28 (Ala1), SEQ ID NO:32 (Ala5), SEQ ID NO:33 (Ala6), SEQ ID NO:34 (Ala7), SEQ ID NO:36 (Ala9), SEQ ID NO:26 (Ala13), SEQ ID NO:38 (Leu), SEQ ID NO:29 (Ala2), SEQ ID NO:30 (Ala3), SEQ ID NO:31 (Ala4), SEQ ID NO:39 (Ala4+5), SEQ ID NO:27 (Ala14), SEQ ID NO:35 (Ala8), and SEQ ID NO:37 (Ala10) or any combination thereof.

In addition, the present invention provides a method of making the transgenic plant of this invention, comprising: a) transforming a cell of a plant with a heterologous nucleic acid construct encoding a mutant AL1 protein, wherein said heterologous nucleic acid construct comprises a nucleotide sequence such as SEQ ID NO:40 (K144), SEQ ID NO:41 (E145), SEQ ID NO:42 (E146), SEQ ID NO:43 (EE146), SEQ ID NO:44 (A147Y), SEQ ID NO:45 (L148), SEQ ID NO:46 (L148V), SEQ ID NO:47 (L148V*), SEQ ID NO:48 (L148G) SEQ ID NO:106 (L145A), and SEQ ID NO:49 (II151) or any combination thereof; and b) regenerating the transgenic plant from said transformed plant cell. The heterologous nucleic acid construct of this method can further comprise a nucleotide sequence such as SEQ ID NO:28 (Ala1), SEQ ID NO:32 (Ala5), SEQ ID NO:33 (Ala6), SEQ ID NO:34 (Ala7), SEQ ID NO:36 (Ala9), SEQ ID NO:26 (Ala13), SEQ ID NO:38 (Leu), SEQ ID NO:29 (Ala2), SEQ ID NO:30 (Ala3), SEQ ID NO:31 (Ala4), SEQ ID NO:39 (Ala4+5), SEQ ID NO:27 (Ala14), SEQ ID NO:35 (Ala8), and SEQ ID NO:37 (Ala10) or any combination thereof.

Also provided herein is an isolated nucleic acid comprising a nucleotide sequence encoding a mutant AL1 protein, wherein the nucleotide sequence can be SEQ ID NO:40 (K144), SEQ ID NO:41 (E145), SEQ ID NO:42 (E146), SEQ ID NO:43 (EE146), SEQ ID NO:44 (A147Y), SEQ ID NO:45 (L148), SEQ ID NO:46 (L148V), SEQ ID NO:47 (L148V*), SEQ ID NO:48 (L148G) SEQ ID NO:106 (L145A), and SEQ ID NO:49 (II151) or any combination thereof. The nucleic acid construct can also comprise a nucleotide sequence such as SEQ ID NO:28 (Ala1), SEQ ID NO:32 (Ala5), SEQ ID NO:33 (Ala6), SEQ ID NO:34 (Ala7), SEQ ID NO:36 (Ala9), SEQ ID NO:26 (Ala13), SEQ ID NO:38 (Leu), SEQ ID NO:29 (Ala2), SEQ ID NO:30 (Ala3), SEQ ID NO:31 (Ala4), SEQ ID NO:39 (Ala4+5), SEQ ID NO:27 (Ala14), SEQ ID NO:35 (Ala8), and SEQ ID NO:37 (Ala10) or any combination thereof.

Furthermore, the present invention provides a mutant AL1 protein comprising an amino acid sequence selected from the group consisting of SEQ ID NO: 17 (K144), SEQ ID NO:18 (E145), SEQ ID NO:19 (E146), SEQ ID NO:20 (EE146), SEQ ID NO:21 (A147Y), SEQ ID NO:22 (L148), SEQ ID NO:23 (L148V), SEQ ID NO:24 (L148G), SEQ ID NO:25 (II151), SEQ ID NO:109 (L145A), SEQ ID NO:3 (Ala1), SEQ ID NO:15 (Ala5), SEQ ID NO:5 (Ala6), SEQ ID NO:6 (Ala7), SEQ ID NO:8 (Ala9), SEQ ID NO:9 (Ala13), SEQ ID NO:11 (Leu), SEQ ID NO:12 (Ala2), SEQ ID NO:13 (Ala3), SEQ ID NO:14 (Ala4), SEQ ID NO:4 (Ala4+5), SEQ ID NO:10 (Ala14), SEQ ID NO:7 (Ala8), and SEQ ID NO:16 (Ala10), as well as an isolated nucleic acid encoding any of the proteins of this invention.

BRIEF DESCRIPTION OF THE DRAWINGS

FIG. 1 shows the amino acid sequence of TGMV Rep, from amino acid 110-179, and the sequences of alanine and leucine substitution mutants. Underlined amino acids correspond to a conserved helix-loop-helix motif found in the Rep proteins of all geminiviruses; double underlined amino acids show the substitutions.

Figure 2A:
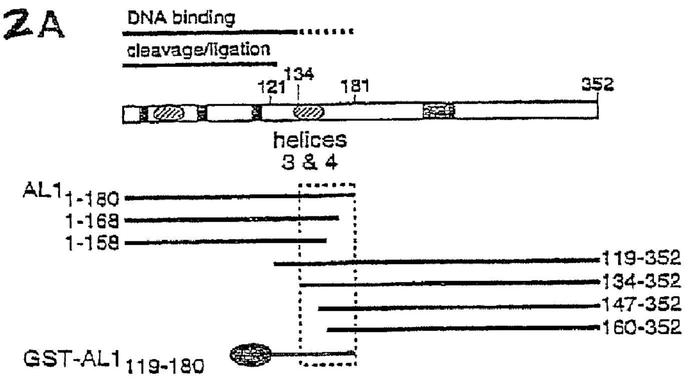
FIG. 2A diagrams the AL1 protein, showing the positions of the three conserved cleavage motifs (solid boxes), two predicted pairs of helices (hatched circles), and the ATP binding site (hatched box). The domains for DNA binding and cleavage/ligation activity are indicated by solid lines and the oligomerization domain is shown as a dashed line. Solid lines below the AL1 diagram mark the sizes of the truncated proteins and are designated by their N- and C-terminal amino acids. The boxed region indicates the limits of the core oligomerization domain.

The present invention now will be described more fully herein.

DETAILED DESCRIPTION OF THE INVENTION

As used herein, the terms "a," "an" and "the" can mean one or more than one. For example, "a cell" can mean a single cell or a plurality of cells.

The present method utilizes the expression of trans dominant mutants of the geminivirus replication protein Rep, or AL1/C1, to confer increased resistance to geminiviruses in transgenic plants. While not wishing to be held to a single underlying theory, the present inventors hypothesize that the mutant proteins interfere with the replication activity of the wild type viral protein that is produced by the infecting geminiviruses, thus reducing the replication of infecting viruses and leading to enhanced resistance.

The present inventors determined that certain mutations in the AL1 sequence enhance the properties of the Rep protein that are useful in creating transgenic geminivirus resistant plants. The present invention provides nucleic acid constructs useful in producing transgenic plants with increased resistance to geminivirus infection. Prior to the present invention, trans dominant mutants of the Rep (AL1) protein contained mutations in catalytic motifs, e.g., the active site for DNA cleavage (motif III) and the ATPase domain (e.g., in the P-loop sequence).

Nucleic acids according to the present invention encode a mutant AL1 protein, wherein the protein acts as a trans dominant negative mutant, and can comprise a mutation in the Rb binding domain that decreases binding of the AL1 protein to the plant retinoblastoma protein, compared to that which would occur in the presence of wild type AL1. In TGMV virus, the Rb binding domain is found between amino acids 100-180. The present mutation Ala5 (EKY159) and Leu are examples of such mutations, resulting in decreased Rb binding compared to wild type AL1.

Nucleic acids according to the present invention encode a mutant AL1 protein, wherein the protein acts as a trans dominant negative mutant, and has a mutation in the oligomerization domain that decreases binding of the mutant AL1 to wild type AL1, compared to that which would occur in the presence of only wild type AL1. Such mutants result in decreased replication of infecting geminiviruses. The present mutation Ala5 (EKY159) and Leu are examples of such mutations, resulting in decreased AL1/AL1 binding compared to wild type AL1.

Nucleic acids according to the present invention encode a mutant AL1 protein, wherein the protein acts as a trans dominant negative mutant, and further comprises a mutation that results in enhanced repression of the viral promoter.

Specific examples of AL1 mutations in the TGMV viral genome are provided herein. It will be apparent to those skilled in the art that, in related geminiviruses, the retinoblastoma binding domain and oligomerization domain can be determined as shown herein. Mutations similar to the present TGMV mutations for other geminiviruses can thus be obtained.

The Geminiviridae family consists of three subgroups that differ with respect to insect vector, host range and genome structure. Subgroup I includes leafhopper-transmitted viruses that generally infect monocot plants and have single-component genomes. Subgroup III includes whitefly-transmitted viruses that infect dicot plants and most commonly have bipartite genomes. Subgroup II viruses are transmitted by leafhoppers and have single-component genomes like Subgroup I, but infect dicot plants like Subgroup III. Members of the three subgroups use similar replication and transcription strategies, although differences exist.

Geminiviruses have small genomes consisting of either one or two circular ss DNA molecules ranging from about 2.5 to about $3\times10^3$ nucleotides in size. The genomic DNAs contain divergent coding sequences separated by 5' intergenic regions. The coding capacity of the genomes varies among the different subgroups. Subgroup I viruses specify four open reading frames for polypeptides greater than 10 kDa, whereas subgroup II and III viruses encode six to seven open reading frames. There are currently two nomenclatures for geminivirus genes. The first nomenclature identifies viral genes as to whether they are specified by the virion (V) or complementary (C) sense DNA strands, whereas the second nomenclature designates genes with respect to the left (L) or right (R) of the 5' intergenic region. The C and L designations are equivalent, as are the V and R designations.

The genomes of Subgroup III geminiviruses typically consist of two DNA components, designated A and B. Both components are required for efficient infection of host plants. The A component encodes all of the information necessary for viral replication and encapsidation, whereas the B component cannot replicate in the absence of A DNA, but is required for systemic movement of the virus and symptom production in infected plants. The A component typically contains five open reading frames (ORFs), four of which (AL1/C1, AL2/C2, AL3/C3 and AL4/C4) are specified by overlapping sequences on the complementary strand. Mutations in the AL3 gene result in severely delayed and attenuated symptoms (Morris et al., *J. Gen. Virol.* 72:1205 (1991); Etessami et al., *J. Gen. Virol.* 72:1005 (1991); Sung and Coutts, *J. Gen. Virol.* 76:1773 (1995)).

AL1/C1 (Rep) and AL3/C3 (Ren) proteins are involved in geminivirus replication, and AL1/C1 (Rep) and AL2/C2 proteins act in regulating viral gene expression. Mutation of the AL1 open reading frame was shown to block viral replication, whereas an AL3 mutant resulted in reduced DNA levels (Sunter et al., *Virology* 179:69 (1990); Sung and Coutts, *J. Gen. Virol.* 76:1773 (1995)). Additionally, transgenic plants that contained the AL1 gene and constitutively expressed the Rep protein in the absence of AL3 supported replication of DNA B, demonstrating that Rep is sufficient for replication in the presence of host factors. (Hanley-Bowdoin et al., *Proc. Natl. Acad. Sci. USA* 87:1446 (1990); Elmer et al. *Nucleic Acids Res.* 16:7043 (1988)).

The genomes of all geminiviruses employ the same general strategy for duplication and expression: a rolling circle replication system that amplifies ssDNA and produces dsDNAs that serve as templates for replication and transcription. The double-stranded form of DNA is divergently transcribed from a 5' intergenic region that also includes the plus-strand origin of replication.

Rolling circle replication is a two-step process involving synthesis of the leading and lagging-strand DNA, which are separate events. The single-stranded 'plus' strand is first used as a template for the synthesis of the 'minus' strand, resulting in a double-stranded replicative form (RF). The replicative form then serves as a template for plus-strand synthesis to generate free ssDNA. A site-specific nick primes plus-strand DNA synthesis (a hallmark of rolling circle replication systems). In subgroup I viruses, minus-strand synthesis appears to be primed by RNA that is most likely generated by pol $\alpha$/primase complex. The mechanism of minus-strand replication in subgroup III is unknown. (The plus strand corresponds to the virion strand found in both ssDNA and dsDNA; the minus strand is the complementary strand found only in dsDNA).

Thus, geminivirus replication requires two origins, one for plus-strand synthesis and one for minus-strand synthesis. The plus-strand origin of geminiviruses from all three subgroups has been mapped to the 5' intergenic region, which also contains the promoters for virion and complementary-sense transcription. The cis elements that mediate viral replication and transcription are best characterized for the Subgroup III geminivirus, TGMV.

Geminiviruses fall into three subgroups based on their insect vector, host range and genome structure. Most dicot-infecting viruses have two genome components, designated A and B, and are transmitted by whiteflies. The single genome components of monopartite, dicot-infecting geminiviruses most resemble the A components of the bipartite viruses. The genome components are arranged similarly with 5' intergenic regions separating divergent transcription units. The 5' intergenic regions contain the viral replication origin (Revington et al., *Plant Cell* 1:985 (1989); Lazarowitz et al., *Plant Cell* 4:799 (1992)) and transcription signals (Eagle et al., *Plant Cell* 6:1157 (1994); Orozco et al., *Virology* 242:346 (1998)).

Dicot-infecting bipartite geminiviruses encode two replication proteins, AL1 and AL3, and recruit the remainder of their replication machinery from the host plant. For monopartite dicot-infecting geminiviruses such as tomato yellow leaf curl virus (TYLCV), the equivalent proteins are designated as C1 and C3, respectively. The AL1 (Rep) protein is the only viral protein essential for viral replication (Elmer et al., *Plant Mol. Biol.* 10:225 (1988); Hayes and Buck, *Nucleic Acids Res.* 17:10213 (1989); Hanley-Bowdoin et al., *Proc. Natl. Acad. Sci. USA* 87:1446 (1990)). AL1 induces the synthesis of host replication machinery in infected plant cells (Nagar et al., *Plant Cell* 7:705 (1995)). The AL3 protein is not required for replication, but enhances the level of viral DNA accumulation (Etessami et al., *J. Gen. Virol.* 72:1005 (1991); Morris et al., *J. Gen. Virol.* 72:1205 (1991)).

AL1 interferes with normal cell cycle regulation in plants and, subsequently, transgenes are silenced after several generations. Thus, AL1 proteins defective in multiple activities offer the best strategy for production of long term resistance.

The present invention is directed to the production of transgenic plants having increased resistance to geminivirus infection, to nucleic acid constructs useful in producing such plants, and to plant cells transformed with such constructs. The nucleic acid constructs contain a nucleotide sequence encoding a mutant AL1 protein or portion of a mutant AL1 protein.

Mutant AL1 proteins according to the present invention can comprise a mutation in the Rb binding domain, such that binding of AL1 to Rb in the plant cell is decreased. Rb is a negative regulator of the cell cycle and a common target of DNA viruses. Interference with the endogenous Rb protein leads to an uncontrolled cell cycle.

Mutant AL1 proteins according to the present invention can comprise a mutation in the oligomerization domain, to produce trans dominant negative mutants. Trans dominant negative mutant proteins negatively interfere in trans with geminiviral replication during infection.

Mutant AL1 proteins according to the present invention can comprise a mutation that enhances repression of the AL1 promoter. AL1 regulates viral DNA replication and transcriptional repression by binding to a conserved sequence in the overlapping plus-strand replication origin and the AL1 promoter. Mutants with enhanced repression of the AL1 promoter will interfere with replication of infecting wild-type geminiviruses.

Specific mutant Rep proteins of the present invention (see Tables 1-3) include proteins comprising the amino acid sequences shown as Leu (SEQ ID NOs:75&76), Ala1 (SEQ ID NOs:55&56), Ala4+5 (SEQ ID NOs:77&78), Ala6 (SEQ ID NOs:65&66), Ala7 (SEQ ID NOs:67&68), Ala8 (SEQ ID NOs:69&70), Ala9 (SEQ ID NOs:71&72), Ala13 (SEQ ID NOs:51&52) and Ala14 (SEQ ID NOs:53&54); these mutants are modified in the oligomerization domain and interfere with viral replication. They also display the property of enhanced repression of transcription from the Rep promoter. Because of their enhanced repression activity, the oligomerization mutants are likely to confer enhanced geminivirus resistance to transgenic plants. Mutants Ala13, Ala4+5, Ala6, and Ala7 also display impaired Rb binding and thus can be stably expressed in plants. The present invention additionally provides mutant Rep proteins shown as Ala2 (SEQ ID NOs:57&58), Ala3 (SEQ ID NOs:59&60), Ala4 (SEQ ID NOs:61&62), Ala5 (SEQ ID NOs:63&64) and Ala10 (SEQ ID NOs:73&74).

The present invention further provides the mutant proteins listed in Tables 4 and 5, comprising the amino acid sequences shown as K144 (SEQ ID NOs:79&80), E145 (SEQ ID NOs: 81&82), E146 (SEQ ID NOs:83&84), EE146 (SEQ ID NOs: 85&86), A147Y (SEQ ID NOs:87&88), L148 (SEQ ID NOs:

89&90), L148V/L148V* (SEQ ID NOs:91&92 and 93&94), L148G (SEQ ID NOs:95&96), L145A (SEQ ID NOs: 111&112) and II151 (SEQ ID NOs:97&98). The present invention provides a mutant AL1 protein comprising the amino acid sequence of any of the mutants described herein. Such a mutant AL1 protein will have the amino acid sequence of the wild type AL1 protein (SEQ ID NO:1 for TGMV; SEQ ID NO:107 for CbLCV), which is available, for example in the Genbank database (and is incorporated herein in its entirety by reference), including the mutation as shown in the amino acid sequence of the respective mutants described herein in lieu of the wild type sequence at the mutated site. Further provided in this invention is a nucleic acid encoding the mutant AL1 protein of this invention. The nucleic acid sequence of this invention can be any sequence that encodes the mutant AL1 protein described herein and encompasses a variety of coding sequences due to the degeneracy of the nucleic acid code. For example, a nucleic acid encoding a mutant AL1 protein of this invention can have the nucleic acid sequence of wild type AL1 protein (SEQ ID NO:50 for TGMV; SEQ ID NO:110 for CbLCV) as is available, for example, from the Genbank database (and is incorporated by reference herein in its entirety), and including the mutation as shown in the nucleic acid sequence of the mutant AL1 protein as described herein in lieu of the wild type sequence at the mutated site.

Accordingly, mutant AL1 proteins of the present invention can comprise any combination of (1) a mutation in the oligomerization domain (trans dominant negative mutant); (2) a mutation in the Rb binding domain (decrease binding of AL1 to Rb); 1 and/or (3) a mutation that increases repression of the AL1 promoter.

Mutant AL1 proteins of the present invention can comprise or further comprise (in combination with another mutation as described herein) a mutation in the DNA cleavage and/or ATPase domain, where such mutations produce trans dominant negative mutants.

The present methods can thus utilize expression of a (mutant) trans dominant viral AL1/C1 protein in transgenic plants, where the mutant contains a change in the Rb binding domain that decreases binding of the Rep protein to the Retinoblastoma homologue found in the plant to be transformed (compared to binding of the Rb homologue to wild-type AL1 protein). Mutant AL1/C1 proteins can also have a mutation in the oligomerization domain, such that viral replication is suppressed (compared to that which would occur in the presence of wild type AL1 protein). The combination of a mutation in the Rb domain as described above, and a mutation in the oligomerization domain results in a stably expressed AL1 (Rep) protein capable of suppressing the replication of infecting geminivirus.

The development of geminivirus resistant plants is desirable. One approach is the expression of trans dominant negative mutants of the geminivirus protein Rep (also called AL1 or C1), which is the only viral protein required for geminivirus replication.

The geminivirus AL1 protein, which localizes to the nuclei of infected plant cells, plays key roles in geminivirus DNA replication and transcription. AL1 confers virus-specific recognition of its cognate origin of replication and initiates plus-strand DNA synthesis. AL1 also functions as a transcriptional repressor by blocking host-mediated activation of its promoter. Biochemical studies of TGMV AL1 have established that it is a sequence-specific DNA binding protein, a DNA cleavage/ligation enzyme and an ATPase. AL1 also forms large oligomers and interacts with the replication enhancer protein, AL3. All of the known activities of AL1 except for ATP hydrolysis are mediated by overlapping domains in the N-terminus of the protein.

The present invention is directed to a series of AL1 mutants modified in conserved sequence and structural domains of the protein (Orozco et al., *J. Biol. Chem.* 273:24448 (1998)). Analysis of the mutant proteins established the importance of these motifs for AL1 function and revealed that DNA binding and cleavage are tightly linked, involving many of the same amino acids. However, the domain requirements for these activities can be distinguished by their dependence on AL1/AL1 interactions, which are only required for DNA binding and not for DNA cleavage/ligation.

AL1 also acts as a plant cell regulator to create an environment that facilitates efficient viral replication. Analysis of transgenic plants that constitutively expressed the TGMV viral replication protein revealed that AL1 induces the expression of a host DNA synthesis protein, proliferating cell nuclear antigen (PCNA), in mature cells. This observation suggests that AL1 is analogous to the DNA tumor antigen proteins of mammalian viruses, which induce replication machinery in their hosts by altering cell cycle and transcriptional controls. The elevated levels of PCNA mRNA detected in TGMV infected tissue and the interaction between TGMV AL1 and a plant homologue of the animal tumor suppressor protein, retinoblastoma, suggest that AL1 can use similar strategies to modify plant cells.

The present invention utilizes mutant Rep proteins that are impaired for interaction with the retinoblastoma (RB) homologues from maize and *Arabidopsis*, Rb is a negative regulator of the cell cycle and a common target of DNA tumor viruses in mammalian cells. A Rep mutant that cannot bind Rb is likely to prove less detrimental to plants, and thus could be combined with other mutations for stable expression of trans dominant negative Rep mutants in transgenic plants.

The present invention provides Rep mutations suitable for use in transgenic plants. All of the mutations target one or more highly conserved residues in geminivirus Subgroup II and III Rep proteins.

The use of Rep mutants that are modified in the DNA cleavage or ATPase domains to produce transgenic virus resistant plants has been problematic, with a lack of stable expression of Rep in the transgenic plants. The use of Rep mutants according to the present invention, such as one combining an oligomerization mutation with a retinoblastoma binding mutation, overcomes this difficulty. The present mutants Ala4+5 and Ala7 display impaired Rb binding, indicating stable expression in plants. The Leu, Ala4+5, Ala6, Ala7, Ala8, Ala9, Ala13 and Ala14 mutants act as trans dominant negative mutants in transient replication assays, and display enhanced repression activity in transcription assays.

Together, the Ala1, Ala4+5, Ala6, Ala7 and Ala13 mutations define a novel Rb binding domain found in the Rep proteins of Subgroup II and III geminiviruses. The Rb binding motif has not been identified before. The Ala1 and Ala13 mutations are located in a 17 amino acid sequence that is highly conserved among most dicot-infecting geminiviruses. The Ala4+5 and Ala6 mutations are in a strongly predicted helix-loop-helix structural motif found in the Rep proteins of all geminiviruses. Hence, these mutations are likely to be broadly applicable for developing resistance strategies against all subgroups of geminiviruses. The Ala1, Ala 4+5, Ala6, and/or Ala7 mutations can be incorporated into a Rep trans dominant mutant to stabilize Rep expression. The interaction of a geminivirus Rep protein with a retinoblastoma homologue from a dicot species has not been described before.

The Ala4+5, Ala6, Ala7 and Ala13 mutations can be sufficient to confer stable geminivirus resistance to plants because they also display trans dominant negative interfering activity in replication assays and enhanced repression activity in transcription assays.

The Ala1, Ala4+5, Ala6, Ala7, Ala13 and LEU mutants are TGMV Rep mutants containing amino acid mutations in the sequence of TGMV Rep from amino acids 111-180 (TLVWGEFQVD GRSARGGCQT SNDAAAEALN ASS KEEALQI IREKIPEKYL FQFHINLNSNL DRIFDKTPEP (SEQ ID NO: 2)), where the underlined amino acids correspond to a conserved helix-loop-helix motif found in the Rep proteins of all geminiviruses.

AL1 is a large oligomeric protein that binds double-stranded DNA, catalyzes cleavage and ligation of single-stranded DNA, and interacts with other viral and host proteins. Earlier experiments mapped the TGMV AL1 oligomerization domain between amino acids 121-181 and the DNA binding domain within amino acids 1 to 181. In the studies reported herein, truncated TGMV AL1 proteins were used to refine the limits of the oligomerization domain and generate site-directed mutations in conserved charged hydrophobic residues of the domain to assess their importance in AL1 function. Nearly all of the mutants attenuated or abolished AL1-directed viral DNA replication. In contrast, the replication defective mutants were enhanced for AL1-mediated transcriptional repression. Yeast two-hybrid experiments revealed that several of the mutations reduced AL1 complex stability, particularly amino acids 157-159. This mutation also disrupted protein interactions in insect cells between the full-length mutant AL1 and the AL1 oligomerization domain fused to GST. In addition, replication defective AL1 mutants interfered with DNA synthesis from wild type TGMV A, indicating that these proteins are good candidates for use in developing geminivirus resistant transgenic plants.

AL1 has several functions in replication and transcription. AL1 mediates both virus-specific recognition of its cognate origin, and transcriptional repression by binding to the direct repeat sequence. Geminivirus replication and termination is regulated by AL1 DNA cleavage and ligation within an invariant sequence in the loop of a conserved hairpin. In addition, AL1 induces accumulation of a host replication factor, PCNA, in infected cells. Recombinant AL1 specifically binds double-stranded DNA, cleaves and ligates single-stranded DNA, and hydrolyzes ATP. Geminivirus AL1 also interacts with itself, AL3 and a plant homologue of the mammalian retinoblastoma protein, PRB1.

The domains of TGMV AL1 for double stranded DNA binding, single stranded DNA cleavage and ligation, and AL1 oligomerization have previously been mapped (Orozco et al., *J. Biol. Chem.* 272:9840 (1997); Orozco et al., *J. Biol. Chem.* 273:24448 (1998)). The AL1 DNA cleavage and ligation domain is located in the first 120 amino acids and the oligomerization domain maps between amino acids 120-181. DNA binding activity requires amino acids 1-130 for protein-DNA contacts and the AL1 oligomerization domain. The Examples provided herein describe truncation studies and use of site-directed mutants to show that the oligomerization domain lies between amino acids 134 and 181 and that additional sequences outside the core domain influenced protein interactions. The mutations were also tested for their impact on viral DNA replication and transcription (in protoplasts).

Yeast dihybrid assays established that Leu, Ala1, Ala4+5, Ala6, Ala7 and Ala13 Rep mutants are impaired for interaction with the Rb homologues from maize and/or *Arabidopsis*. Leu, Ala4+5, Ala6 and Ala7 were shown to act as trans dominant negative inhibitors of geminivirus replication and displayed enhanced transcriptional repression activity in *Nicotiana*. These activities in combination with impaired Rb binding make Leu, Ala4+5, Ala6 and Ala7 excellent candidates for conferring geminivirus resistance to plants.

TGMV AL1 regulates viral DNA replication and transcriptional repression by binding to a conserved sequence in the overlapping plus-strand replication origin and AL1 promoter. Previous experiments showed that AL1/DNA interactions require both the DNA binding domain (amino acids 1-131) and oligomerization domain (amino acids 121-181) of AL1. To further map the oligomerization domain, AL1 truncations of TGMV AL1 (SEQ ID NO: 1) were generated that deleted additional amino acid sequences from the N- and C-terminus. Truncating an additional 13 amino acids from the C-terminus abolished AL1 interactions, demonstrating that the C-terminal boundary of the oligomerization domain is between amino acids 168 and 181. The N-terminal boundary of the oligomerization domain was unclear when interactions were observed with the full length GST-AL1 protein. However, AL1 oligomerized with a GST-AL1 fusion protein containing AL1 amino acids 119-180, demonstrating that this region is sufficient to form AL1 complexes. When N-terminal truncations were co-purified with GST-AL1 119-180, protein interactions were lost when amino acids 134-147 were removed. Thus, the N-terminal boundary of the minimal oligomerization domain lies between position 134 and 147, which includes two highly predicted alpha-helices. In the presence of full-length GST-AL1, deletion of the helices resulted in near background levels of interactions, indicating that weak interactions can occur in the region 147 to 180 and that the helices are important for stable complex formation.

Alanine substitutions (see FIG. 1 and Table 3) were generated at highly conserved, charged or hydrophobic residues across the oligomerization domain to assess the contributions of specific amino acids in vitro and in vivo. The mutant proteins were first analyzed in insect cells for their effect on AL1 oligomerization. Although the amino acid changes were insufficient to disrupt interactions with the full-length GST-AL1, a more stringent assay using GST-AL1 119-180 revealed that AL1 EKY159 (Ala7) was impaired for oligomerization. However, AL1 EKY159 (Ala7) interacted with an AL1 truncation lacking the N-terminus (or, including the C-terminus) that retained the core oligomerization domain, suggesting that multiple interfaces stabilized the protein complexes. These results are consistent with the observation that additional contacts outside the core oligomerization domain contributed to interactions with wild type truncated AL1.

A yeast two-hybrid assay was employed to determine the quantitative effects of the mutations on AL1 oligomerization with the wild type protein. Consistent with the results from insect cells, AL1159 (Ala7) was the most impaired for protein interactions. Mutations that significantly altered AL1 interactions in yeast were clustered between amino acids 152 and 172, within the region defined as the minimal oligomerization domain by the truncation experiments. Mutations in the helices slightly impaired AL1 interactions compared to the 152 to 172 region, consistent with the deletion analysis, suggesting that this region is also required. The alanine substitutions are not predicted to disrupt helix formation although the sequence of the helices is fairly divergent among AL1 proteins. These results indicate that the sequence is an important feature of this region. Alanine substitutions adjacent to the oligomerization domain (D120 (Ala14) and RS-R125 (Ala1)) indicate that this region contributes contacts that stabilize protein interactions.

AL1 subunits defective for viral DNA replication can potentially form complexes with wild type AL1 and interfere with normal viral DNA replication. Thus, expression vectors for seven mutant proteins were co-transfected into protoplasts with a wild type TGMV replicon. All of the mutants significantly reduced single stranded and double stranded DNA synthesis. Mutations in the conserved ATP binding site and DNA cleavage motif and a C-terminal truncation of AL1 from related geminiviruses were previously shown to interfere with replication in transgenic plants. All of these mutant proteins are candidates for developing plants resistant to geminivirus infection. However, AL1 toxicity to plant cells results in silencing of transgenes over successive generations. In addition, single mutations can potentially recombine with wild type virus to produce a functional protein. The goal of the present invention is to design non-toxic mutants of AL1 that are defective in multiple functions.

Ten of the twelve mutants enhanced repression of the AL1 promoter 2- to 4-fold above wild type AL1. AL1 K-E179 is essentially wild type for replication and AL1 oligomerization. AL1 RS-R125 lacks DNA binding activity that is essential for AL1-mediated repression. No specific correlation was observed between the strength of AL1 interactions in yeast and the differential effect of the mutations on replication versus transcriptional repression. For example, AL1 EKY159 (Ala7) and AL1 Q-HN165 (Ala8) altered AL1 interactions to 0% and 102% of wild type, respectively, but displayed essentially identical effects on replication and transcription. Similarly, AL1 ND133 (Ala3) repressed expression nearly 4-fold higher than wild type AL1 and greatly reduced replication, whereas protein interactions were comparable to wild type AL1. This suggests the effect of the mutations can be attributed to changes in the structure and/or the number of AL1 subunits in the complex. Thus, structural analysis of the wild type and mutant AL1 proteins will be essential to determine the cause of the phenotypic changes observed with the mutant proteins. Ten of the mutations showed increased transcriptional repression concomitant with decreased viral replication.

The present methods utilize nucleic acid constructs encoding mutated versions of naturally occurring geminivirus AL1/C1 (Rep) proteins. The term "mutated" as used herein regarding proteins or polypeptides means that at least one amino acid in the wild-type or naturally occurring protein or polypeptide sequence has been replaced with a different amino acid, and/or added and/or deleted from the sequence. Preferably at least two or more adjacent amino acids in the wild-type sequence are replaced, added and/or deleted. Mutant AL1/C1 proteins can contain from about 2 to about 30, or more, replaced, added and/or deleted amino acids. A particularly preferred mutation is the replacement of conserved, charged or hydrophobic amino acid residues with alanine.

As used herein, the term "AL1/C1" or "Rep" protein refers to the geminivirus proteins that are known in the art as AL1/C1 proteins in geminiviruses. Subgroup II and III geminiviruses encode a protein that is identifiable by those skilled in the art, based on structure and/or function, as the AL1/C1 protein. As used herein, the term "AL1/C1" as it is applied to polypeptides includes fragments of AL1/C1 proteins. As used herein, the term "AL1/C1" as it is applied to nucleic acid sequences (including naturally occurring sequences and genes, and synthesized nucleic acid sequences) refers to sequences that encode a naturally occurring AL1/C1 protein or polypeptide, or a mutated AL1/C1 protein or peptide as described herein.

Mutated AL1/C1 proteins and polypeptides useful in the present methods are those which, when expressed in a plant cell, reduce the sensitivity of the cell (or a plant comprising such cells) to infection by a geminivirus. Mutated AL1/C1 proteins and polypeptides useful in the present methods are also those which, when expressed in a plant cell, increase or enhance the resistance or tolerance of the cell (or a plant comprising such cells) to infection by a geminivirus.

As used herein, "sensitivity" of a plant to infection by a geminivirus refers to the rate at which symptoms of geminivirus infection develop, and the severity of symptoms. Plants with reduced sensitivity to infection have delayed development of symptoms and/or less severe symptoms of geminivirus infection compared to that which occurs in a control plant.

As used herein, "tolerance" refers to plants that are infected with and contain a geminivirus, but do not show symptoms associated with viral infection. Tolerant crop plants are able to produce a good crop despite geminivirus infection. As used herein, plants that are "immune to infection" by a geminivirus are those in which replication of the virus is prevented. As used herein, plants that are "resistant" to infection by a geminivirus are those that show both immunity to infection and tolerance.

It will be apparent to those skilled in the art that the ability of a plant to survive and thrive when exposed to geminiviruses is a continuum, from plants that are less sensitive to infection, to those that are tolerant to infection, to those that are resistant to, geminiviruses. A plant that shows enhanced resistance or tolerance to geminivirus infection is considered herein to also show reduced sensitivity to geminivirus infection. In each case, the severity and/or rate of development of symptoms in plants with enhanced resistance (reduced sensitivity) to geminiviruses is less than that which occurs in a control plant.

Sensitivity, tolerance or resistance to geminivirus infection can be measured at the level of a plant cell or at the level of a single plant (e.g., by assessing the severity or rapidity of symptom development), or at the level of a plurality of plants (e.g., by assessing the prevalence and/or severity of infection, or the crop yield). Sensitivity in transgenic plants can be assessed by comparison to non-transformed control plants of the same species.

As used herein, the terms "protein" and "polypeptide" are used interchangeably, and refer to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

The mutated geminivirus AL1/C1 proteins useful in the present methods can be based on any naturally occurring AL1/C1 protein. A series of site-directed mutants of any AL1/C1 protein can be prepared and screened for the ability to enhance geminivirus resistance (for example, using tobacco protoplast complementation assays as described in the Examples, below). Mutant AL1/C1 proteins or polypeptides capable of reducing sensitivity to geminivirus infection in transgenic plants according to the methods herein are identified, and nucleic acid constructs capable of encoding the mutant protein are prepared according to methods known in the art, for use in producing transgenic plants with reduced sensitivity to (or increased resistance or tolerance to) geminivirus infection.

As used herein, a "native" or "naturally-occurring" nucleic acid sequence is a sequence that is found in non-transgenic cells or tissue. Native nucleic acid sequences are thus those that have not been artificially altered, such as by site-directed mutagenesis. Once native nucleic acid sequences have been determined, molecules having these sequences can be synthesized or produced using recombinant nucleic acid procedures as are known in the art. As used herein, a native geminivirus nucleic acid sequence is that which can be isolated from or identified in a naturally occurring geminivirus.

Mutants of AL1/C1 proteins from various geminiviruses are suitable for use in the present invention, including but not limited to: Tomato golden mosaic virus (TGMV), tomato mottle virus, tomato yellow leaf curl virus (TYLCV), tomato leaf curl virus (TLCV), potato yellow mosaic virus (PYMV), African cassava mosaic virus (ACMV), Indian cassava mosaic virus, bean golden mosaic virus (BGMV), bean dwarf mosaic virus, squash leaf curl virus, cotton leaf curl virus (CLCV), beet curly top virus (BCTV), Texas pepper virus and Pepper Huastico virus. A preferred mutant protein or polypeptide is one in which one or more amino acid residues are replaced with alanine.

The sequences of AL1/C1 proteins from various geminiviruses are known and available through the GenBank database.

Unless otherwise stated, nucleotide sequences are presented herein by single strand only, in the 5' to 3' direction, from left to right. Nucleotides are represented herein in the manner recommended by the IUPAC-IUB Biochemical Nomenclature Commission.

The methods and constructs of the present invention are useful in transforming dicot plant species to produce plants with reduced sensitivity to geminivirus infection. Dicots suitable for use in practicing the present invention include plants from the Fabaceae, Solanaceae, Brassicaceae, Rosaceae and Compositae families. Examples of plant species suitable for transformation with the DNA constructs of the present invention include but are not limited to tobacco (*Nicotiana tabacum*), potato (*Solanum tuberosum*), soybean (*glycine max*), tomato (*Lycopersicon esculentum*), cassava (*Manihot esculenta*), beets, peanuts (*Arachis hypogaea*), cotton (*Gossypium hirsutum*), citrus trees (*Citrus* spp.), corn or maize (*Zea mays*), beans (e.g., green beans (*Phaseolus vulgaris*) and lima beans (*Phaseolus limensis*)), peas (*Lathyrus* spp.), sugarbeet, sunflower, carrot, celery, flax, cabbage and other cruciferous plants, pepper, strawberry, lettuce, alfalfa, oat, wheat, rye, rice, barley, sorghum and canola. Thus an illustrative category of plants which can be transformed with the constructs of the present invention are members of the family Solanacae, and particular plants which can be transformed using the constructs of the present invention are tomato and tobacco.

A variety of techniques are available in the art for introduction of DNA constructs into a plant cell host. These include, but are not limited to, *Agrobacterium*-mediated transfection, injection, electroporation and microparticle bombardment. In preferred embodiments, plants are transfected using *Agrobacterium*-mediated transfection, or intact plants are inoculated using microprojectiles carrying a nucleic acid construct according to the present invention.

In practice, a crop comprising a plurality of plants of the invention can be planted together in an agricultural field. By "agricultural field" is meant a common plot of soil or a greenhouse. Thus, the present invention provides a method of providing a crop of transgenic plants.

Those familiar with recombinant DNA methods available in the art will recognize that one can employ a nucleic acid sequence coding for a mutant AL1/C1 protein of the present invention, joined in the sense orientation with appropriate operably linked regulatory sequences, to construct transgenic cells and plants. Appropriate regulatory sequences for expression of nucleic acid sequences in the sense orientation include any of the known eukaryotic translation start sequences, in addition to promoter and polyadenylation/transcription termination sequences.

Nucleic acid constructs (or "transcription cassettes") of the present invention include, 5' to 3' in the direction of transcription, a promoter as discussed above and, operatively associated with the promoter, a nucleic acid sequence encoding a mutant AL1/C1 protein of the present invention. The construct can optionally contain a termination sequence including stop signal for RNA polymerase. Each of these regulatory regions should be capable of operating in the cells of the tissue to be transformed. Any suitable termination signal can be employed in carrying out the present invention, examples thereof including, but not limited to, the nos terminator, the CaMV terminator, or native termination signals derived from the same gene as the transcriptional initiation region or derived from a different gene. The term "operatively associated," as used herein, refers to nucleic acid sequences on a single nucleic acid molecule, which sequences are associated so that the function of one is affected by the other. Thus, a promoter is operatively associated with a nucleic acid sequence when it is capable of affecting the transcription of that sequence (i.e., the sequence is under the transcriptional control of the promoter). The promoter is said to be "upstream" from the sequence, which is in turn said to be "downstream" from the promoter.

The various fragments comprising the various constructs, transcription cassettes, markers, and the like can be introduced consecutively by restriction enzyme cleavage of an appropriate replication system, and insertion of the particular construct or fragment into the available site. After ligation and cloning, the nucleic acid construct can be isolated for further manipulation. All of these techniques are amply exemplified in the literature (see, e.g., J. Sambrook et al., *Molecular Cloning, A Laboratory Manual* (2d Ed. 1989) (Cold Spring Harbor Laboratory)).

The term "nucleic acid sequence" as used herein refers to a DNA or RNA molecule, and more particularly a linear series of deoxyribonucleotides or ribonucleotides connected to one another by bonds, typically phosphodiester bonds, between the 3' and 5' carbon of the adjacent pentoses.

The term "promoter" refers to a region of a DNA sequence that incorporates the necessary signals for the efficient expression of a coding sequence. This can include sequences to which an RNA polymerase binds but is not limited thereto, and can include other sequences to which other regulatory proteins bind, together with regions involved in the control of protein translation. Promoters employed in carrying out the present invention can be promoters that are constitutively active in the subject plant cell. Numerous constitutively active promoters that are operable in plants are available. A preferred example is the 35S promoter from fig wort mosaic virus (FMV), or the Cauliflower Mosaic Virus (CaMV) 35S promoter. In the alternative, the promoter can be promoter that is spatially active or active only in a specific tissue of the plant (see e.g., U.S. Pat. No. 5,459,252 for root-specific promoters), or an inducible promoter (e.g., a promoter active in plants that is induced by specific conditions, such as wounding or infection by specific pathogens).

Methods of making transgenic (or 'recombinant') plants of the present invention, in general, involve first providing a plant cell capable of regeneration (the plant cell typically residing in a tissue capable of regeneration). The plant cell is then transformed with a DNA construct comprising a transcription cassette of the present invention (as described herein) and a transgenic plant is regenerated from the transformed plant cell. The transforming step can be carried out by any suitable technique as is known in the art, including but not limited to bombarding the plant cell with microparticles carrying the transcription cassette, infecting the cell with *Agrobacterium tumefaciens* containing a Ti plasmid carrying the transcription cassette, or any other suitable technique.

Vectors which can be used to transform plant tissue with the nucleic acid constructs of the present invention include both *Agrobacterium* vectors and ballistic vectors, as well as other suitable vectors known to those in the art. *Agrobacterium tumefaciens* cells containing a nucleic acid construct of the present invention are useful in methods of making transformed plants. Plant cells are infected with *Agrobacterium tumefaciens* to produce a transformed plant cell, and then a plant is regenerated from the transformed plant cell, according to methods known in the art. Numerous *Agrobacterium* vector systems useful in carrying out the present invention are known (see, e.g., U.S. Pat. No. 4,459,355; U.S. Pat. No. 4,795,855; U.S. Pat. No. 4,940,838, the entire contents of each of which are incorporated by reference herein).

Microparticles carrying constructs of the present invention, which microparticle is suitable for the ballistic transformation of a plant cell, are also useful for making transformed plants of the present invention. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050; in Christou et al., U.S. Pat. No. 5,015,58; and in Agracetus European Patent Application Publication No. 0 270 356, entitled "Pollen-mediated Plant Transformation." (the entire contents of each of which are incorporated by reference herein).

Plant species can be transformed with the nucleic acid constructs of the present invention by the DNA-mediated transformation of plant cell protoplasts and subsequent regeneration of the plant from the transformed protoplasts in accordance with procedures known in the art. Fusion of tobacco protoplasts with DNA-containing liposomes or via electroporation is known in the art (Shilleto et al., *Methods in Enzymology,* 153:313-336 (1987)).

As used herein, transformation refers to the introduction of exogenous nucleic acid molecules into cells, so as to produce transgenic cells stably transformed with the exogenous nucleic acid. Transformed plant cells are induced to regenerate intact plants through application of cell and tissue culture techniques that are known in the art. The method of plant regeneration is chosen so as to be compatible with the method of transformation. The stable presence and orientation of the exogenous DNA in transgenic plants can be verified by the Mendelian inheritance of the DNA sequence, as revealed by standard methods of DNA analysis applied to progeny resulting from controlled crosses.

Any plant tissue capable of subsequent clonal propagation, whether by organogenesis or embryogenesis, can be transformed with the constructs of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Transgenic plants of the present invention can take a variety of forms. The plants can be chimeras of transformed cells and non-transformed cells; the plants can be clonal transformants (e.g., all cells transformed to contain the transcription cassette); the plants can comprise grafts of transformed and non-transformed tissues. The transformed plants can be propagated by a variety of means known in the art, such as by clonal propagation or by classical breeding techniques.

The examples which follow are set forth to illustrate the present invention, and are not to be construed as limiting thereof.

Example 1

Mutagenesis and Cloning of AL1 proteins: The plasmid pNSB148 containing the AL1 coding sequence in a pUC 118-background, was used as the template for site directed mutagenesis. The oligonucleotide primers and resulting clones are listed in Table 4. DNA fragments containing the mutations were verified by DNA sequence analysis. Plant expression cassettes for mutant AL1 proteins were generated by subcloning SalI/NcoI fragments from the mutant clones into the same sites in a wild type AL1 plant expression cassette pMON1549 (Fontes et al., *Plant Cell* 6:405 (1994); Fontes et al., *J. Biol. Chem.* 269:8459 (1994)). In pMON1549, AL1 expression is under the control of the cauliflower mosaic virus 35S promoter with a duplicated enhancer region and the E9 3' end.

Baculovirus vectors were generated for expressing mutant and truncated AL1 proteins in insect cells. Expression vectors coding for mutant AL1 proteins were generated by subcloning BglII/BamHI inserts from the mutant plant expression cassettes into the BamHI site of pMON27025 (Luckow et al, *J. Virol.* 67:4566 (1993)). Expression vectors for the truncated proteins AL1 $_{119-352}$ (pNSB516), AL1 $_{1-120}$ (pNSB388), and AL1 $_{1-180}$ (pNSB517) have been described previously (Orozco et al., *J. Biol. Chem.* 272:9840 (1997)). N-terminal truncations, AL1 134-352 and AL1 147-352 were generated by inserting a DNA linker containing a start codon into the NotI site of pNSB593 and pNSB595. AL1 160-352 was created by inserting an SphI linker into the SspI site of pMON1539. SphI/BamHI fragments from the resulting clones were inserted into the same sites of the baculovirus vector, pNSB448, to give pNSB8O3 (AL1 134-352), pNSB876 (AL1 147-352) and pNSB633 (AL1 160-352). The C-terminal truncation AL1 1-158 (pNSB646) was created by digesting pMON1539 with NdeI and SspI, repairing with Klenow, and subcloning into the filled BamHI site of pMON27025. The AL1 1-168 truncation, pNSB7O8, was created by inserting an XbaI linker into the repaired BssHII of pNSB609.

Yeast expression cassettes were generated containing the coding sequence for AL1 fused to the Gal4 DNA binding domain, pNSB736, or Gal4 activation domain, pNSB8O9. The pAS2-1 Gal4 BD and Gal4 AD cloning vectors were purchased from Clontech. pNSB736—The BamHI/NdeI fragment of pMON1539 was cloned into the same sites of pAS2-1 pACT2-Gal4 AD vector to give pNSB736. pNSB735—the BamHI/Ndel fragment of pMon 1539 was cloned into the SmaI site of pACT2. pNSB8O9 replaced AatII/BamHI fragment from pNSB735 with the AatII/BamHI fragment from pMON1549. Mutant AL1 expression cassettes were created by replacing the AatII/BamHI wild type fragments from pNSB735 with AatII/BamHI inserts from the mutant plant expression cassettes.

Transient Replication Assays: Protoplasts were isolated from *Nicotiana tabacum* NT suspension cells, electroporated and cultured according to published methods (Fontes et al., *J. Biol. Chem.* 269:8459 (1994)). The transfections contained 15 μg each of replicon DNA containing a partial tandem copy of TGMV B (pTG1.4B described in Fontes et al., *Plant Cell,* 6:405 (1994)), wild type or mutant AL1 plant expression cassette and an AL3 plant expression cassette, (pNSB41 described in Fontes et al., *J. Biol. Chem.* 269:8459 (1994)).

Interference Assays: For the interference assays, transfections containing 2 μg of replicon DNA containing a partial tandem copy of TGMV A and 40 μg of mutant AL1 expression cassette or the empty expression vector. Total DNA was extracted 3 days post-transfection and analyzed for double- and single-stranded viral DNA accumulation by DNA gel blot hybridization.

Repression Assays: Protoplasts were isolated from *Nicotiana benthamiana* suspension cells, electroporated and cultured according to published methods (Eagle et al., *Plant Cell* 6:1157 (1994)).

AL1 Interactions in Yeast: The yeast strain Y187 was co-transformed with an expression cassette for wild type AL1 or maize Rb fused to the Gal4 binding domain (BD) and expression cassettes for mutant AL1 proteins fused to the Gal4 activation domain (AD). Total extracts were assayed for B-galactosidase activity using the substrate o-nitrophenyl B-D-galactopyranoside, essentially as described by Clontech (Palo Alto, Calif.). Protein concentrations were measured by Bradford assays. The activities were standardized against wild type AL1 fused to both the Gal4 activation domain and DNA binding domain.

Example 2

Figure 2B:
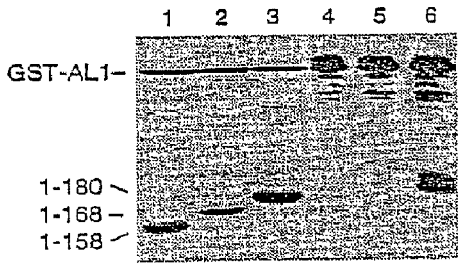
FIG. 2B shows the results of an immunoblot assay to detect protein interactions of C-terminal truncated proteins with full length GST-AL1. Total extracts from insect cells co-expressing GST-AL1 with truncated AL1 proteins were incubated with glutathione-sepharose, washed and eluted in SDS-sample buffer. Bound AL1 proteins were visualized by immunoblot assays. Input (lanes 1-3) and bound (lanes 4-6) fractions were resolved by SDS-polyacrylamide gel electrophoresis and analyzed by immunoblotting. AL1 1-180 (lanes 1 and 4), AL1 1-168 (lanes 2 and 5), AL1 1-158 (lanes 3 and 6).
Figure 2C:
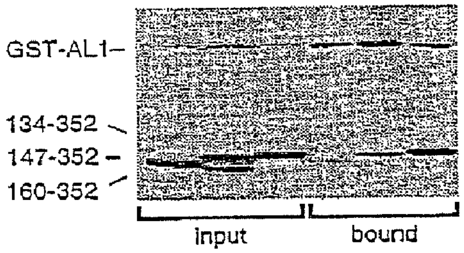
FIG. 2C shows the results of an immunoblot assay to detect protein interactions of N-terminal truncated proteins with full length GST-AL1. Total extracts from insect cells co-expressing GST-AL1 with truncated AL1 proteins were incubated with glutathione-sepharose, washed and eluted in SDS-sample buffer. Bound AL1 proteins were visualized by immunoblot assays. Input (lanes 1-3) and bound (lanes 4-6) fractions were resolved by SDS-polyacrylamide gel electrophoresis and analyzed by immunoblotting. AL1 134-352 (lanes 1 and 4), AL1 147-352 (lanes 2 and 5) and AL1 159-352 (lanes 3 and 6).

The domains for TGMV AL1 DNA binding and DNA cleavage/ligation activity have been well defined and key structural and sequence motifs have been identified for these activities (Orozco et al., *J. Biol. Chem.* 273:24448 (1998)). In contrast, TGMV AL1 protein interactions with the viral protein AL3, plant retinoblastoma (Rb) homologue, and AL1 itself have been broadly mapped to overlapping domains in the center of the protein. In the present studies, additional N- and C-terminal truncations were generated to further define the limits of the AL1 oligomerization domain (FIG. 2A). Full length GST-AL1 1-352 was co-expressed with truncated AL 1 proteins in baculovirus-infected insect cells and purified on glutathione-sepharose resin. Total extracts and purified proteins were resolved by SDS-PAGE and AL1 was visualized by immunoblotting with AL1 polyclonal antisera. As reported previously, the C-terminal truncation AL1 1-180 (FIG. 2B, lanes 3 and 6) co-purified with full length GST-AL1 1-352. Further deletion of the C-terminus to amino acids 168 (lanes 2 and 5) and 158 (lanes 1 and 4) abolished interactions with GST-AL1 protein, demonstrating that the C-terminal limits of the oligomerization domain are between positions 168 and 180. In contrast, N-terminal truncation mutations AL1 134-352 (FIG. 2C, lanes 3 and 6), AL1 147-352 (lanes 2 and 5) and AL1 160-352 (lanes 1 and 4) showed a gradual disappearance of interactions with GST-AL1 1-352; the AL1 147-352 and AL1 160-352 interactions varied between weak to background levels. Thus, the N-terminal limit of the oligomerization domain was more difficult to define.

Figure 2D:
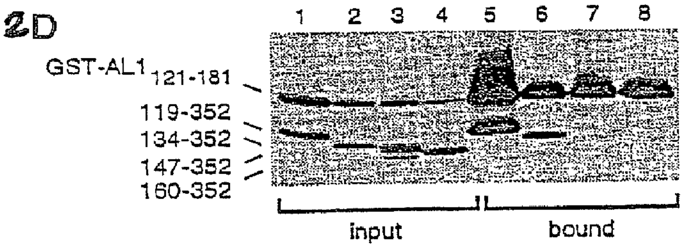
FIG. 2D shows the results of co-purification assays performed with GST-AL1 119-180 and N-terminal truncated AL1 119-352 (lanes 1 and 5), AL1 134-352 (lanes 2 and 6), AL1 147-352 (lanes 3 and 7), and AL1 158-352 (lanes 4 and 8).

Authentic (i.e., native or natural) AL1 also co-purified with a 60 amino-acid fragment of AL1 fused to GST (GST-AL1 119-180 but not with GST alone (FIG. 4A, lanes 1 and 2), demonstrating that sequences between amino acids 119 and 180 are sufficient for AL1 oligomerization. However, additional amino acid contacts can contribute to dimer stability or multimerization. Interactions between GST-AL1 119-180 and the N-terminal truncations of AL1 were then tested. In this assay, deletion to positions 119 (FIG. 2D, lanes 1 and 5) and 134 (lanes 2 and 6) did not affect oligomerization, whereas further deletion to positions 147 (lanes 3 and 7) and 160 (lanes 4 and 8) abolished interactions with GST-AL1 119-180.

Together, the results showed that AL1 amino acids 134 to 180 contain the core oligomerization domain and indicated that sequences outside the core contribute additional contacts.

Example 3

Figure 3:
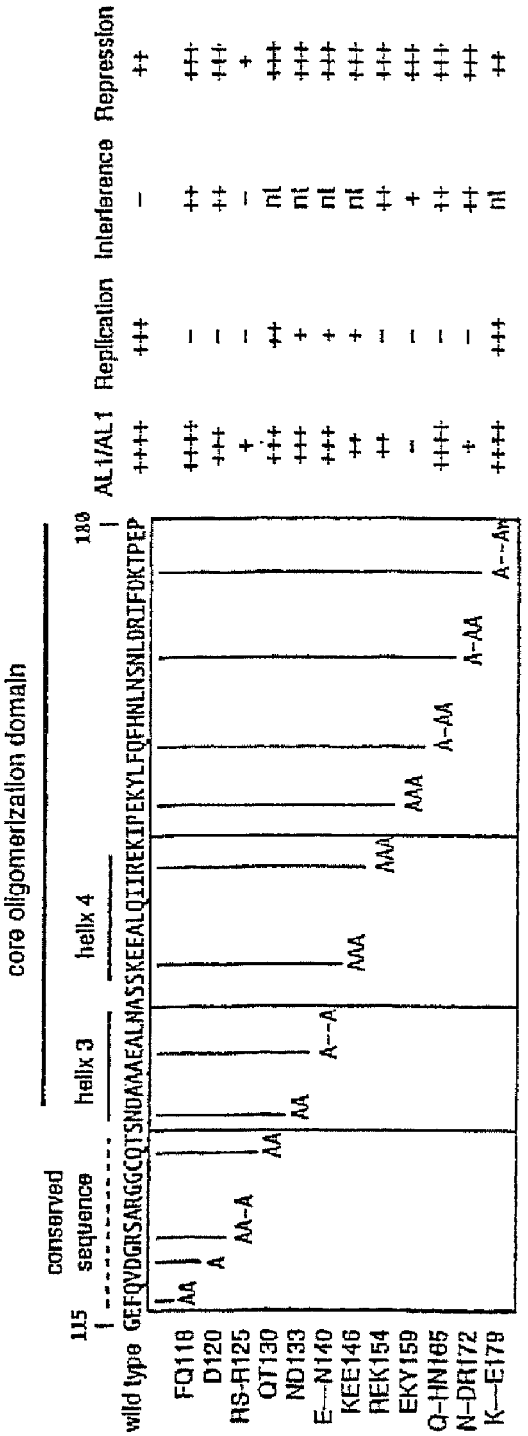
FIG. 3 shows mutations generated in the oligomerization domain of AL1, and their characteristics. The wild-type amino acid sequence presented in FIG. 3 corresponds to amino acids 115-180 of SEQ ID NO: 1.
Figures 4A, 4B, 4C:
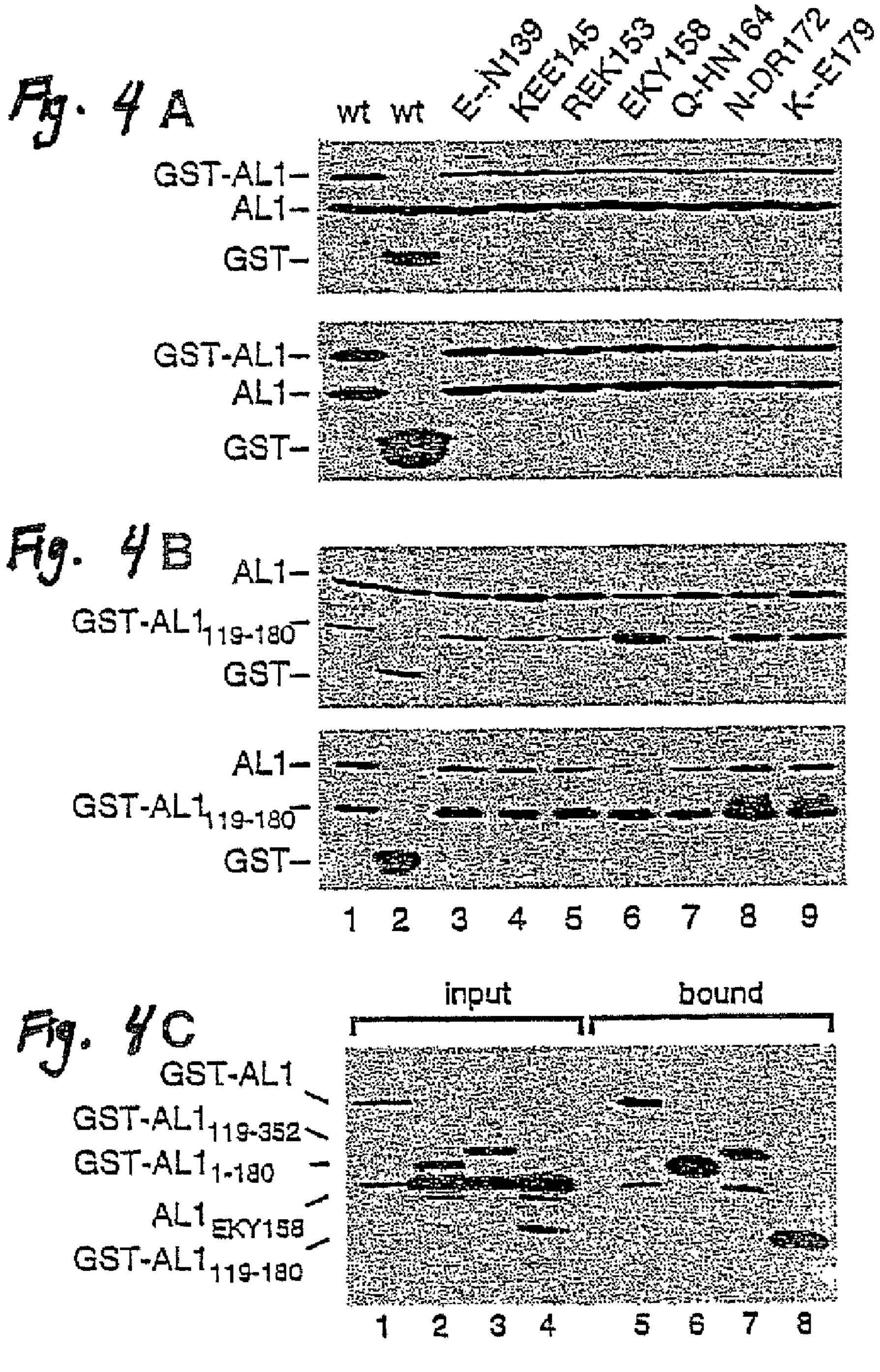
FIG. 4A shows oligomerization properties of AL1 proteins with mutations in the core oligomerization domain in insect cells. Protein interactions were assayed as described in FIG. 1. Mutant AL1 proteins co-expressed with full length GST-AL1 were extracted (top) and bound to glutathione-sepharose (bottom). Lanes correspond to wild type AL1 (lane 1), AL1 E-N140 (Ala4, lane 3), AL1 KEE146 (Ala5, lane 4), AL1 REK154 (Ala6, lane 5), AL1 EKY159 (Ala7, lane 6), AL1 Q-HN165 (Ala8, lane 7), AL1 N-DR172 (Ala9, lane 8), and AL1 K-E179 (Ala10, lane 9). Wild type AL1 was also co-expressed with GST alone (lane 2).
FIG. 4B shows oligomerization properties of AL1 proteins with mutations in the core oligomerization domain in insect cells. Protein interactions were assayed as described in FIG. 1. Mutant AL1 proteins were co-expressed with GST-AL1 119-180. The lanes are as described in panel A.
FIG. 4C shows the mutant AL1 EKY159 co-expressed with GST-AL1 fusion proteins of full-length and truncated AL1. Lanes 1-4 show AL1 proteins bound to glutathione-sepharose. The GST-AL1 proteins assayed were full-length GST-AL1 (lanes 1 and 5), GST-AL1(1-180) (lanes 2 and 6), GST-AL1(119-352) (lanes 3 and 7), and GST-AL1(119-180) (lanes 4 and 8).

Alanine substitutions were generated in conserved and charged residues within the core oligomerization domain and adjacent sequences to identify key amino acids that contribute to AL1 interactions (FIG. 3). Wild type AL1 and proteins with mutations in the core oligomerization domain (E-N140 (Ala4), KEE146 (Ala5), REK154 (Ala6), EKY159 (Ala7), Q-HN165 (Ala8), N-DR172 (Ala9) and K-E179 (Ala10) were expressed with full length GST-AL1 in insect cells (FIG. 4A, top panel) and co-purified on glutathione resin (FIG. 4A, bottom panel). Wild-type (lane 1) and mutant AL1 proteins (lanes 3-9) all interacted with GST-AL1. Wild type AL1 did not co-purify with GST alone (lane 2), demonstrating that the interactions were specific for AL1. Similar experiments using GST-AL1 119-180 (FIG. 4B) identified one mutant EKY159 (Ala7, lane 6), defective for AL1 interactions. Thus a mutation that impaired AL1 oligomerization was revealed only when co-purified with the core oligomerization domain alone, consistent with the observation that sequences outside the domain contribute to stabilizing interactions.

AL1 EKY159 was assayed for co-purification with truncated GST-AL1 proteins to identify the region that stabilized interactions with the mutant protein. As described above, AL1 EKY159 interacted with full length GST AL1 (FIG. 4C, lanes 1 and 5) but not with GST-AL1(119-180) (lanes 4 and 8). AL1 EKY159 interacted with an N-terminal truncation of AL1, GST-AL1(119-352) (lanes 3 and 7) whereas no interaction was detected with a C-terminal truncation of AL1, GST-AL1 (1-180) (lanes 2 and 6). These results demonstrate that the C-terminus contributes additional protein contacts outside of the oligomerization domain that can mask the effect of oligomerization mutations within the core domain.

Figure 5B:
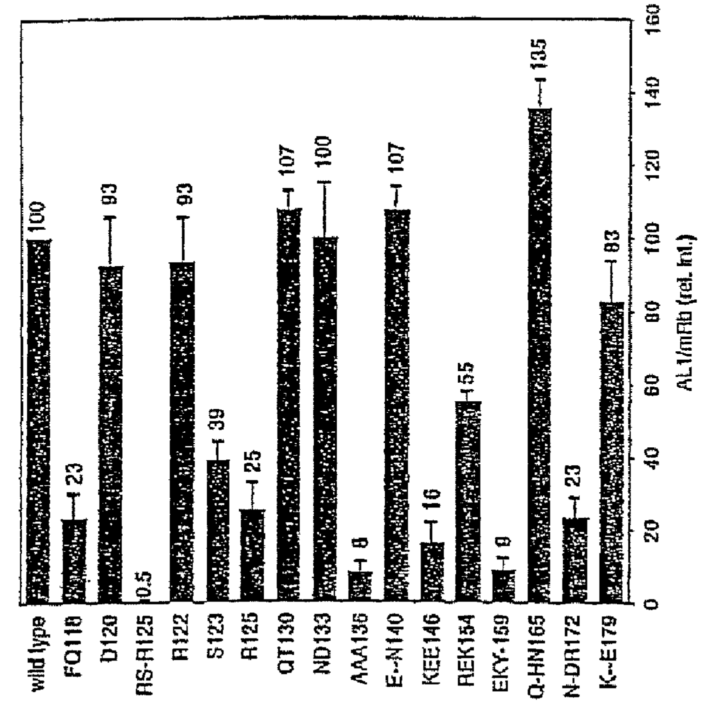
FIG. 5B shows the interaction of mutant AL1 proteins with maize Rb in a yeast dihybrid assay. Expression cassettes for maize Rb (amino acids 214-866, Ach et al., *Mol. Cell. Biol.* 17:5077 (1997)) fused to the GAL4 binding domain and mutant AL1 fused to the GAL4 DNA activation domain were co-transformed into yeast. Interactions between the wild type and mutant AL1 proteins were assayed by measuring B-galactosidase.
Figure 5A:
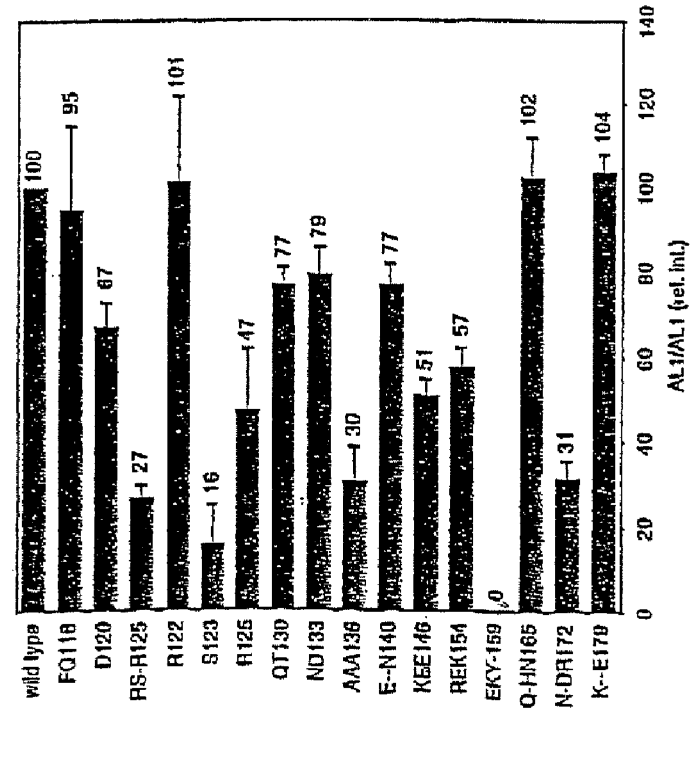
FIG. 5A shows the interaction of mutant AL1 proteins with wild type AL1 in a yeast dihybrid assay. Expression cassettes for wild type AL1 fused to the GAL4 DNA binding domain and mutant AL1 fused to the GAL4 activation domain were co-transformed into yeast. Interactions between the wild type and mutant AL1 proteins were assayed by measuring B-galactosidase.

The co-purification assay in insect cells established the limits of the AL1 oligomerization domain and identified amino acids that can be required for protein interactions. The quantitative impact of the mutations on AL1 oligomerization was then analyzed by yeast two-hybrid assays. Expression cassettes for AL1 fused to the GAL4 DNA binding domain and wild type or mutant AL1 fused to the GAL4 activation domain were co-transformed into yeast. Activation of the promoter was assayed by measuring the beta-galactosidase activity in total yeast extracts. Interactions between the mutant and wild type AL1 fusion proteins were then expressed as a percent of wild type AL1/AL1 mediated activation (FIG. 5A). Four of the mutations reduced AL1 interactions to 51% (KEE146, Ala5), 57% (REK154, Ala6), 0% (EKY159, Ala7), and 31% (N-DR172, Ala9) of wild type. In contrast, the mutation Q-HN165 (Ala8) and K-E179 (Ala10) interactions were comparable to wild type. These mutations, located between amino acids 143 and 172, are within the core oligomerization domain. Mutations N-terminal to the core domain, D120 (Ala14), QT130 (Ala2), ND133 (Ala3), and E-N140 (Ala4) were less impaired for AL1 oligomerization, consistent with a role in providing stabilizing contacts to the interaction. The mutation FQ118 (Ala 13) showed no impact on AL1 interactions. Although the mutation RS-R125 (Ala1) is located outside the core domain, AL1 interactions were reduced to 27% of wild type. However, this protein is also impaired for DNA binding. Mutant proteins with reduced AL1 interactions in yeast, REK154 (Ala6), EKY159 (Ala7) and N-DR172 (Ala9) were expressed at levels comparable to wild type, as determined by immunoblot of total protein extracts. Thus, the reduced interactions were not attributable to reduced protein expression levels.

The impact of the AL 1 mutations on binding to maize Rb was also analyzed by yeast two-hybrid assays. Expression cassettes for maize Rb (amino acids 214-866) fused to the GAL4 DNA binding domain and mutant AL1 proteins fused to the GAL4 activation domain were co-transformed into yeast. Activation of the promoter was assayed by measuring the beta-galactosidase activity in total yeast extracts. Results were then expressed as a percent of wild type AL1/Rb mediated activation (FIG. 5B).

Earlier studies have shown that TGMV AL1 and Rb interact with each other, but the region of the AL1 protein that mediates interaction was not known. The limits of the Rb binding domain were defined by using a baculovirus expression system. Insect cells were co-infected with recombinant baculoviruses corresponding to various AL1 truncations and to a GST fusion with amino acids 214-866 of Maize Rb (GST-mRb). The abilities of the different AL1 truncation to bind GST-mRb were assessed by cofractionation on glutathione-sepharose resin. Total extracts and purified proteins were resolved by SDS-PAGE, and AL1 and GST-mRb were visualized by immunoblotting with AL1 and GST antibodies, respectively. The C-terminal truncation AL1(1-180) copurified with GST-mRb. Further deletion to amino acids 168 and 158 abolished interactions with GST-mRb. Similarly, the N-terminal truncation AL1(101-352) cofractionated with GST-mRb, whereas truncations at positions 110 and 119 were unable to bind GST-mRb. Together, these results mapped the limits of the pRB binding domain between AL1 amino acids 101 and 180. Thus, the C-termini of the pRb binding and oligomerization domains of TGMV AL1 are contiguous, whereas an additional 33 N-terminal amino acids are required for Rb binding (data not shown).

Four of the AL1 mutants were wild type in their ability to bind maize Rb (mRb): D120 (Ala14), QT130 (Ala2), ND133 (Ala3), E-N140 (Ala4), and K-E179 (Ala10).

Seven mutants displayed reduced Rb binding activity. These mutants fell into two distinct classes. One group, which included the core oligomerization domain mutants REK154 (Ala6), EKY159 (Ala7), N-DR172 (Ala9), was impaired to similar degrees for Rb binding and AL1 oligomerization, suggesting that AL1/AL1 interactions may be a prerequisite for binding to Rb. The second group was more severely impaired for Rb binding than for AL1 oligomerization and thus most likely reflects specific AL1 amino acids that contact Rb. This group included FQ118 (Ala13), RS-R125 (Ala1), AAA136 (Leu), and KEE146 (Ala5). One mutant, Q-HN165 (Ala8), displayed enhanced Rb binding activity.

Example 4

The mutations were also assayed for their effect on AL1 functions in vivo. Plant expression cassettes for wild type and mutant AL1 were transfected into NT-1 protoplasts with TGMV B DNA and an expression cassette for AL3. Eleven of the twelve mutants were impaired for the ability to direct viral DNA replication (FIG. 6A) when compared to wild type AL1 (lane 1). Only the mutant AL1 K-E179 (Ala10) supported wild type replication levels (lane 13). Mutations within the core oligomerization domain (lanes 9-12) and the conserved sequence between amino acids 117 and 125 (lanes 2-4) abolished replication. The latter group of mutations is within the DNA cleavage and DNA binding domains as well as the enhancer region for AL1 oligomerization and may have pleiotropic effects on AL1 activity. For example, AL1RS-R125 is impaired for DNA binding (results not shown) as well as AL1 oligomerization. In contrast, low levels of DNA synthesis were observed with AL1 mutations in the predicted alpha-helices (lanes 5-8), suggesting that the sequence of this region is less critical for AL1 function.

Example 5

Figure 7A:
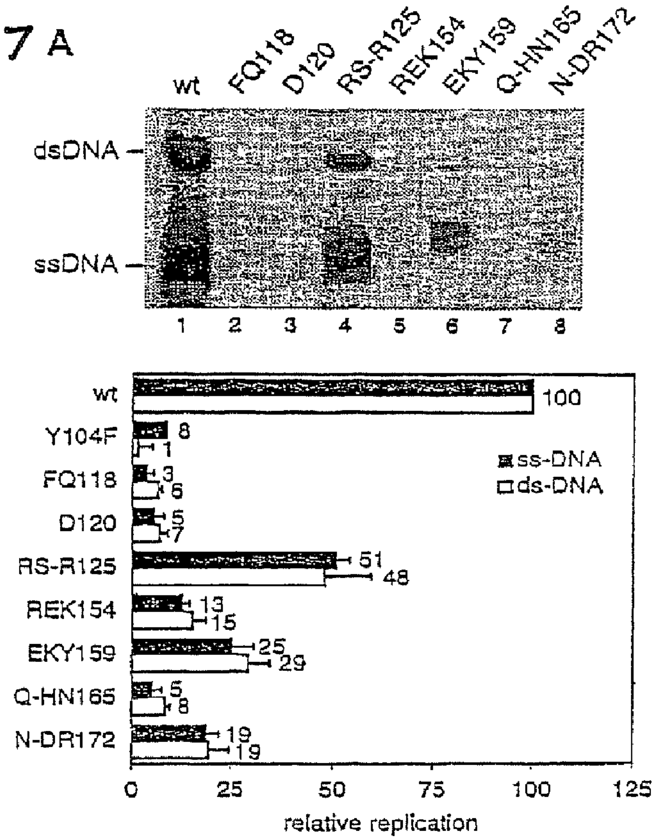
FIG. 7A shows that AL1 proteins defective for viral DNA replication interfere with TGMV A DNA replication. Protoplasts were co-transfected with 2 μg of a TGMV A replicon and 40 μg of expression cassettes coding for mutant AL1 proteins. Total DNA was isolated 3 days post-transfection and analyzed by DNA gel blot hybridization using a radiolabelled TGMV A probe. The top panel shows a representative blot of the replication interference assay. Lanes correspond to transfections of TGMV A DNA with an empty expression cassette (lane 1) and expression cassettes for AL1 FQ118 (Ala13, lane 2), AL1 D120 (Ala14, lane 3), AL1 RS-R125 (Ala1, lane 4), AL1 REK154 (Ala6, lane 5), AL1 EKY159 (Ala7, lane 6), AL1 Q-HIN165 (Ala8, lane 7), AL1 N-DR172 (Ala9, lane 8). The lower panel graphs the level of replicated viral DNA in the presence of excess mutant AL1 relative to wild type replication, averaged from at least three experiments.
Figure 7B:
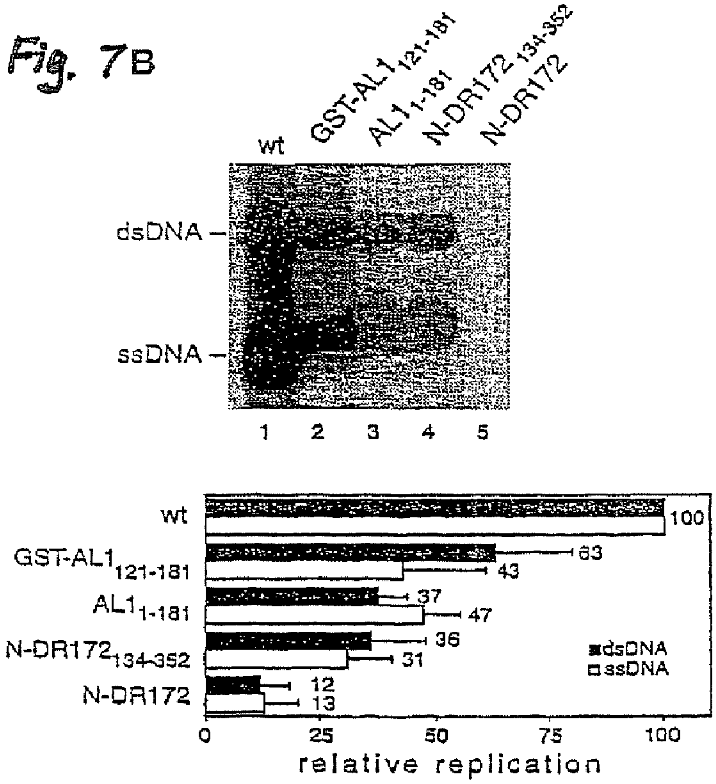
FIG. 7B shows results of experiments as described for FIG. 7A, where the top panel is a representative blot of wild type replication interference by truncated AL1 proteins. Lanes correspond to transfections of TGMV A DNA with an empty expression cassette (lane 1), GST-AL1(119-180) (lane 2), AL1(1-180) (lane 3), AL1 N-DR172(134-352) (lane 4) and AL1 N-DR172 (lane 5). The bottom panel shows the levels of replicated viral DNA in the presence of excess mutant AL1 relative to wild type replication, averaged from at least three experiments.

Whether replication defective AL1 could interfere with normal viral DNA replication was studied. The present inventors tested N-terminal and C-terminal truncations of wild type AL1, which lack the domains for one or more AL1 activities, and an N-terminal truncation of the AL1 N-DR172 mutant for dominant negative interference of viral replication. The oligomerization domain fused to GST (FIG. 7B) and a C-terminal truncation of AL1(1-181) (lane 3) reduced wild type replication, but were significantly less effective than the full length mutant proteins (FIG. 7A). In addition, replication interference by the N-DR172 mutant was less severe in the N-terminal truncated protein (FIG. 7B, lane 4) than in the full length AL1

A wild type TGMV A replicon (2 μg) was transfected into NT-1 protoplasts in the absence and presence of 20-fold excess (40 μg) mutant AL1 expression cassettes. Total DNA was isolated three days post-transfection and analyzed by DNA gel blot hybridization using a radiolabelled TGMV A probe. Mutations in the core oligomerization domain (FIG. 7A), REK154 (Ala6, lane 5), EKY159 (Ala7, lane 6), Q-HN165 (Ala8, lane 7), and N-DR172 (Ala9, lane 8) reduced single-stranded DNA accumulation 5 to 25% of wild type, and double-stranded DNA accumulation 8 to 29%.

Mutations outside the oligomerization domain, FQ118 (Ala13, lane 2) and D120 (Ala14, lane 3), also interfered with replication, reducing single stranded DNA to 3 and 5% of wild type, and double stranded DNA to 1% to 6%, respectively. The mutation RS-R125 (Ala1, lane 4) was the least detrimental, reducing single and double stranded DNA by about 50%.

AL1 proteins defective for viral DNA replication interfered with TGMV A DNA replication. These results demonstrate that AL1 mutations that impair replication in vivo and affect oligomerization in vitro are good candidates for developing transgenic plants resistant to geminivirus infection.

Example 6

Figure 6A:
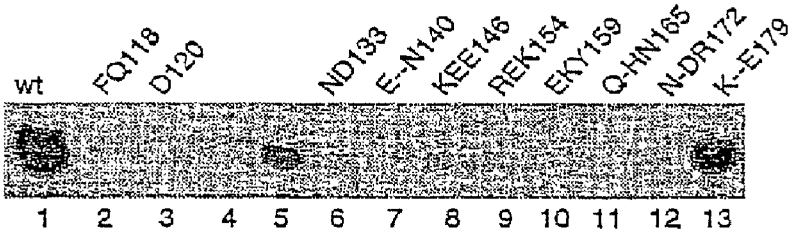
FIG. 6A shows that transient replication of TGMV B DNA is impaired by mutations in the AL1 oligomerization domain and upstream stabilizing region. Double-stranded DNA replication was analyzed in protoplasts co-transfected with expression cassettes for AL3, wild type or mutant AL1 proteins, and a TGMV B replicon. Total DNA was isolated three days post-transfection and analyzed by DNA gel blot hybridization using a radiolabeled TGMV B probe. Lanes correspond to transfections with wild type AL1 (lane 1), AL1 FQ118 (Ala13, lane 2), AL1 D120 (Ala14, lane 3), AL1 RS-R125 (Ala 1, lane 4), AL1 QT130 (Ala2, lane 5), AL1 ND133 (Ala3, lane 6), AL1 E-N140 (Ala4, lane 7), AL1 KEE146 (Ala5, lane 8), AL1 REK154 (Ala6, lane 9), AL1 EKY159 (Ala7, lane 10), AL1 Q-HN165 (Ala8, lane 11), AL1 N-DR172 (Ala9, lane 12), and AL1 K-E179 (Ala10, lane 13).
Figure 6B:
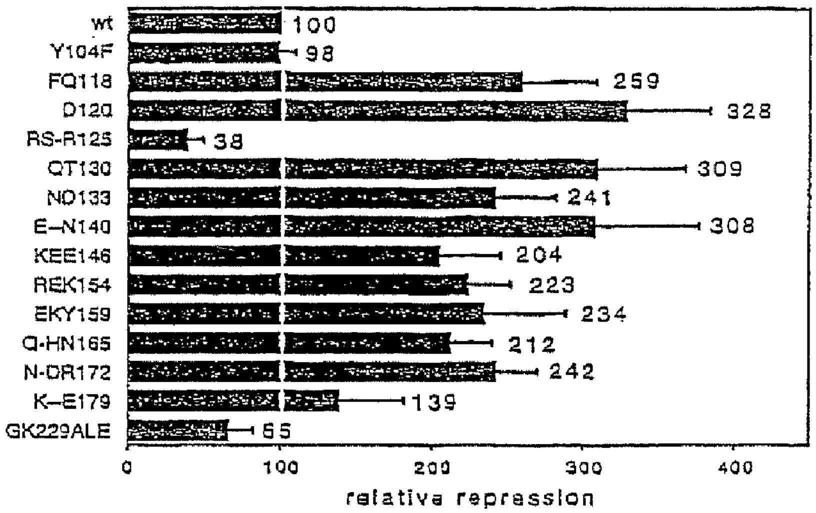
FIG. 6B graphs the relative repression of the AL1 promoter in protoplasts transfected with an expression cassette for wild type AL1 or a mutant AL1, and a reporter with the AL1 promoter and luciferase reporter gene (luc).

The ability of the mutants to repress AL1 promoter activity in vivo was studied. The AL1 promoter fused to the luciferase reporter gene (lux) was transfected into *N. benthamiana* protoplasts either alone or in the presence of plant expression cassettes for wild type and mutant AL1 proteins. In these experiments, wild type AL1 repressed transcription from the AL1 promoter approximately 20-fold. Repression mediated by mutant AL1 proteins was standardized to the percent of wild type repression within each experiment. All of the mutants that reduced viral DNA replication (except for Ala1) also repressed promoter activity 2- to 4-fold higher than wild type AL1. DNA binding is required for repression and Ala1 is a DNA binding mutant. AL1 K-E179 (Ala10) supported normal replication levels and repressed the AL1 promoter similar to wild type AL1. FIG. 6A (see lane 13) and FIG. 6B.

Example 7

The plasmid pNSB148, which contains the AL1 coding sequence in a pUC118 background, was used as the template for site-directed mutagenesis as described previously (Orozco et al., *J. Virol.* 273:24448-24456 (1998)). The oligonucleotide primers and resulting clones are listed in Table 5. Viral DNA fragments containing the mutations were verified by DNA sequence analysis. Viral replicons encoding some of the mutant AL1 proteins were generated, for example, by subcloning SalI/NheI fragments corresponding AL1 amino acids 120-232 from the mutant clones into the same sites into the wild type replicon, pMON1565 (Orozco et al. 1996), to give pNSB954 (K144), pNSB1032 (EE146), pNSB999 (A147Y), pNSB997 (L148), pNSB979 (L148V), pNSB1000 (L148G), and pNSB998 (II151). Alanine substitution mutants are designated [wild type amino acid(s)—final position number]. When the mutation was not to alanine, the mutant amino acid is given after the position number.

Site directed-mutagenesis of CbLCV AL1 was performed using a PCR-based method. Complementary oligonucleotides, Cb-M1 and Cb-M2 (Table 5), were used as primers in combination with the M13 universal and reverse primers, respectively, in two separate amplification reactions with pNSB1085 as a template. pNSB1085 contains a CbLCV A DNA fragment (positions 1499 to 33) carrying the AL1 coding sequence in a pUC118 background. The PCR products of Cb-M1/M13-universal and Cb-M2/M13-reverse amplification reactions were isolated from agarose gels and pooled for a new amplification reaction using M13-universal and reverse primers. The PCR product was digested with BamHI and BglII and cloned into the same sites of a modified pUC118 to give pNSB1097.

Yeast cassettes with the Gal4 DNA binding domain (DBD) were generated using pAS2-1 (Clontech, Palo Alto, Calif.). Zm214C includes a truncated maize RBR1 coding sequence consisting of the pocket and the C-terminal domains fused the DBD {Ach, 1997 #25}. pNSB736 contains a full-length, wild type TGMV AL1-DBD fusion (Orozco et al., *J. Biol. Chem.* 275:6144-6122 (2000)).

Yeast cassettes containing the Gal4 activation domain (AD) were generated using pACT2 (Clontech). Cassettes for wild type TGMV AL1 (pNSB809) and the mutants, KEE146 (pNSB894) and REK154 (pNSB759), have been described. Cassettes for the TGMV mutants, K144 (pNSB916), E146 (pNSB975), EE146 (pNSB1040), A147Y (pNSB1003), L148 (pNSB1001), L148V (pNSB980), L148G (pNSB1004), and 11151 (pNSB1002), were made by replacing the AatII-BamH1 fragment of pNSB735 with the equivalents fragments from pNSB946, pNSB968, pNSB1033, pNSB995, pNSB993, pNSB969, pNSB996 and pNSB994, respectively.

The C1 open reading frame was amplified from a TYLCV (Dominican Republic) genomic clone (Monsanto) using the oligonucleotides, 5'-GGACACCGATTggaTcCAgCATGC-CTC (SEQ ID NO: 103) and CCACAGTCgAatTC-CCCggGCTTACGC (SEQ ID NO: 104). (The lowercase letters indicate mutated nucleotides.) The resulting PCR product (positions 1686 to 12 of the TYLCV-DR genome) was digested with BamHI and SmaI and cloned into pUC119 to give pTYLC78. The corresponding yeast AD vector was constructed by cloning the BamHI (trimmed)/SmaI C1 fragment from pTYLC78 into pACT2 digested with SmaI to give pTYLC102.

pCPCbLCVA.001, which has a single copy of CbLCV A DNA (Turnage et al., Plant J. 30:107-114 (2002)), was modified by PCR mutagenesis using the oligonucleotide 5'-CCTAAATAagatcTACAAGgATcCCACGAAACCCTA (SEQ ID NO: 105) to introduce a BamHI site at the 5' end of the AL1 open reading frame. The resulting clone, pNSB900, was digested with BamHI, and the fragment containing the full-length AL1 sequence was cloned into the BamHI site of pACTII to give pNSB958. The NcoI fragment from pNSB958 encoding amino acids 2-178 of AL1 was then subcloned into pACTII to give pNSB974. The L145A mutation was introduced into the CbLCV AL1 coding sequence of pNSB900 by using the oligonucleotide 5'-GTGTGGAAGAGGCGGccGCAATTATAAGGGC (SEQ ID NO: 106) for PCR mutagenesis. A mutant fragment from the resulting plasmid (pNSB1097) with AatII/NcoI (repaired) ends was subcloned into pNSB974 with AatII/XhoI (repaired) ends to give pNSB1114.

Interactions between the Gal4 fusion proteins were evaluated in *Saccharomyces cerevisiae* strain Y187 by measuring β-galactosidase activity. Protein concentrations were measured by Bradford assays (Biorad, Hercules, Calif.). The enzyme specific activity (1 unit=1.0 μm product/min at pH7.3 at 37° C.) was determined using purified β-galactosidase (Sigma, St. Louis, Mo.) as the standard. The different constructs were tested in a minimum of four independent transformants in at least two experiments. The relative activities of the mutant proteins were normalized against wild type AL1, which was set to 100%.

TGMV A replicons carrying mutant AL1 coding sequences were made using pMON1565, a pUC-based plasmid that contains 1.5 copies of wild type TGMV A DNA (Orozco et al., *J. Virol.* 270:148-158 (1996)). The mutant replicons in Table 5 were generated by replacing the SalI/NheI fragment encoding AL1 amino acids 120 to 313 of pMON1565 with the equivalent fragment of mutant AL1 open reading frames described above. The plasmid, pTG1.4B, which includes 1.4 copies of wild type TGMV B has been described (Fontes et al., *Plant Cell* 6:405-416 (1994)).

For replication assays, protoplast were isolated from *Nicotiana tabacum* (BY2) suspension cells, electroporated and cultured according to published methods (Fontes et al., *J. Biol. Chem.* 269:8459-8465 (1994)) Cells were transfected with 5 μg of wild type or mutant TGMV A replicon DNA and 25 μg of sheared salmon sperm DNA. Total DNA was extracted 72 h after transfection, digested with DpnI and XhoI, and examined for double- and single-stranded viral DNA accumulation by DNA gel blot analysis using a TGMV A specific probe (Fontes et al., *Plant Cell* 6:405-416 (1994)). Viral DNA was quantified by phosphorimage analysis. Each protoplast assay was performed in at least three independent experiments.

For infectivity assays, *N. benthamiana* plants at the 6-leaves stage were inoculated using a biolistics device (Nagar et al., *Plant Cell* 7:705-719 (1995)). Wild type or mutant TGMV A replicon DNA (10 μg) was precipitated onto 1 μm microprojectiles in the presence of a wild-type TGMV B replicon (pTG1.4B) and bombarded into plants. Total DNA was extracted from leaf tissue 14 days after bombardment (Dellaporta et al., 1983), digested with XhoI, and analyzed on DNA gel blots.

The RBR1 binding domain of AL1 has been mapped to between amino acids 101-180 and mutations in residues KEE146 have been shown to impair binding. The KEE146 mutant contains three consecutive alanine substitutions, which may act alone or together to confer the mutant phenotype. To better understand the basis of the phenotype, four additional alanine substitution mutants, K144, E145, E146, and EE146 (FIG. 8A), were produced. The mutant AL1 open reading frames were fused to the coding sequence of Gal4 activation domain (AD) and expressed in yeast. Mutant proteins accumulated to levels comparable to an AD-wild type AL1 fusion, as determined by immunoblot analysis. The AL1 oligomerization properties of the mutant proteins were assessed in two hybrid assays using a wild type TGMV AL1 protein fused to the Gal4 DNA binding domain (DBD). The influence of the mutations on AL1/AL1 interactions was minimal (FIG. 8B, right) and not statistically significant, indicating that none of the mutations have a global effect on AL1 function.

Figure 8:
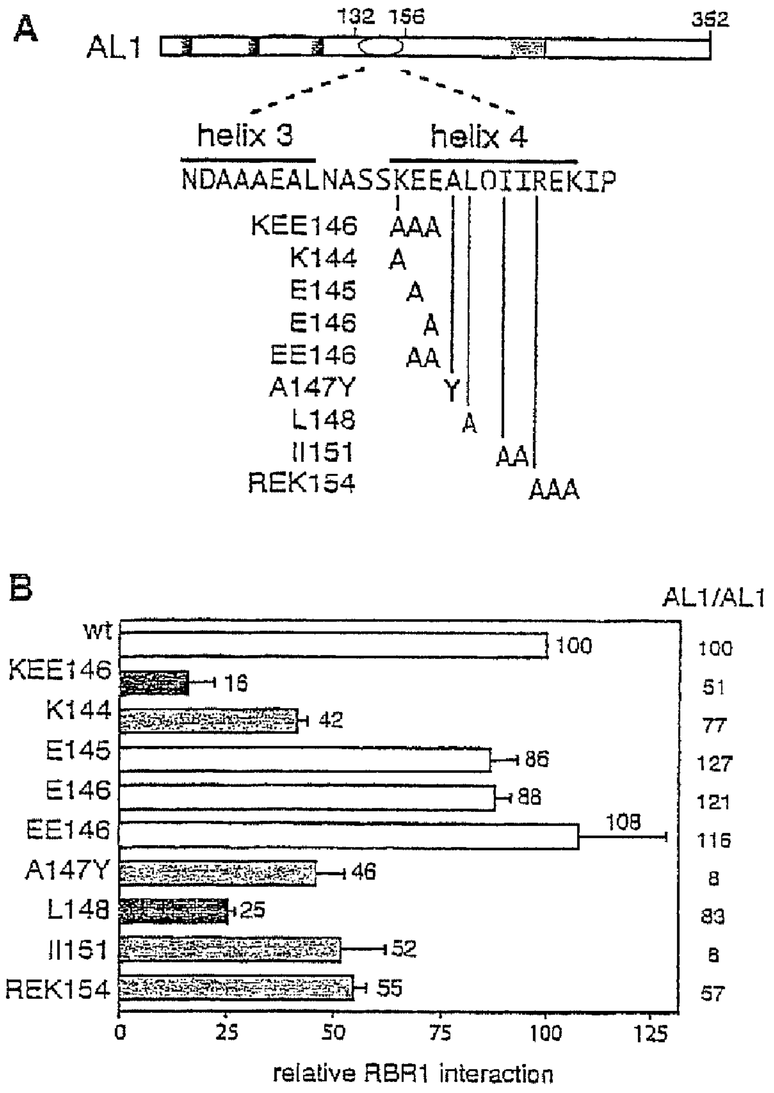
FIG. 8A shows a schematic of TGMV AL1. Solid boxes mark the location of the three motifs conserved among RCR initiator proteins, the oval indicates a predicted set of α-helices, and the stippled box shows the location of the ATP binding domain. The AL1 sequence between amino acids 132 to 156 (SEQ ID NO: 99) is shown, with the locations of the predicted α-helices 3 and 4 indicated. Vertical lines mark the positions of the alanine substitutions. Mutations are designated by the corresponding wild type sequence and the position of the last amino acid that was modified.
FIG. 8B shows results of studies wherein an expression cassette, Zm214C, encoding amino acids 214 to the C-terminus of ZmRBR1, fused to the Gal4 DNA binding domain, was co-transformed into yeast with cassettes for either wild type or mutant AL1 fused to the Gal4 activation domain. Protein interactions were assayed by measuring β-galactosidase activity in total protein extracts and normalized to wild type (100). Filled bars indicate mutants strongly impaired for ZmRBR1 binding, hatched bars mark mutants moderately impaired in this activity, whereas open bars indicate mutants with activity similar to or greater than wild type AL1. The error bars correspond to two standard errors. The effects of the mutations on AL1-AL1 interactions (oligomerization activity) are indicated on the right.

The impact of the mutations on AL1-RBR1 interactions was analyzed in two hybrid assays using a truncated version (Zm214C) of maize RBR1 from amino acid 214 to the C-terminus fused to the Gal4 DBD (Ach et al., Mol. Cell Biol. 17:5077-5086 (1997)). This region contains the A/B pocket domain and the C-terminal domain of RBR1. The E145, E146 and EE146 mutations did not alter AL1/RBR1 binding significantly (FIG. 8B), suggesting that the E residues are not essential for wild type binding activity. In contrast, the K144 mutation reduced RBR1 interactions to 42% of the wild type levels (FIG. 8B), indicating that this residue is required for full binding activity. However, the reduction in RBR1 binding activity was less for K144 than KEE146 (16%; FIG. 8B), thereby uncovering a role for one or both of the E residues in interaction with RBR1.

Mutations in the Helix 4 Motif of AL1 Impair RBR Interactions

The KEE sequence constitutes the first three residues of an 11 amino acid motif designated as Helix 4 (FIG. 8A). The Helix 4 motif is conserved across all geminivirus replication proteins both with respect to amino acid sequence and its predicted α-helical structure. Previous studies have shown that the RBR1 binding activity of an REK154 mutant, which contains three alanine substitution in the last three amino acids of the motif, is reduced 2-fold (FIG. 8B). To further explore the role of the Helix 4 motif in RBR1 binding, alanine substitutions were generated at the conserved L148 and II151 residues and a tyrosine substitution was generated at the invariant A147 position. The Q149 position, which is highly variable, was not mutated.

The mutant AL1 coding sequences were fused to the coding sequence of Gal4 AD and analyzed in yeast two hybrid assays as described herein. The A147Y and II151 mutants displayed significantly lower RBR1 binding activities than wild type AL1 (FIG. 8B). However, these mutations also reduced AL1 oligomerization activity (FIG. 8B, right), indicating that their effects are not specific for RBR1 binding. In contrast, the L148 mutation reduced the AL1/RBR1 interactions to 25% of wild type levels without a concomitant loss in AL1 oligomerization activity (FIG. 8B), thereby establishing the specificity of the mutation for RBR1 binding. Together, these results indicate that several of the amino acid residues in the Helix 4 motif are important for both AL1/RBR and AL1/AL1 interactions in yeasts, and that both the KEE146 and the L148 residues contribute specifically to RBR1 binding.

The KEE146 mutation alters the level of TGMV DNA accumulation in cultured cells and the tissue specificity and symptoms of TGMV infection in plants. To determine if mutations in other Helix 4 residues also impact these viral processes, additional mutants were analyzed in transient replication and infectivity assays. The mutations were transferred into the AL1 open reading frame of a TGMV A replicon and viral DNA accumulation in *Nicotiana tabacum* BY-2 protoplasts was assessed on DNA gel blots. The K144 (FIG. 9A, lane 2) and EE146 (lane 3) mutants replicated to wild type levels (lane 1). A similar result was observed with mutants E145 and E146 (data not shown). The L148 mutant (FIG. 9A, lane 5) also supported viral DNA synthesis but at levels significantly lower than wild type TGMV A (lane 1). This reduction in DNA accumulation (13% of wild type levels) was observed for both double- and single-stranded forms of TGMV DNA. In contrast, the A147Y (FIG. 9A, lane 4) and II151 (lane 5) mutants, both of which severely impaired AL1 oligomerization (FIG. 8B), failed to replicate to detectable levels in cultured cells. Similar viral DNA accumulation patterns were observed when BY-2 protoplasts were co-transfected with a TGMV B replicon and with plant expression cassettes for AL1 and AL3.

Figure 9:
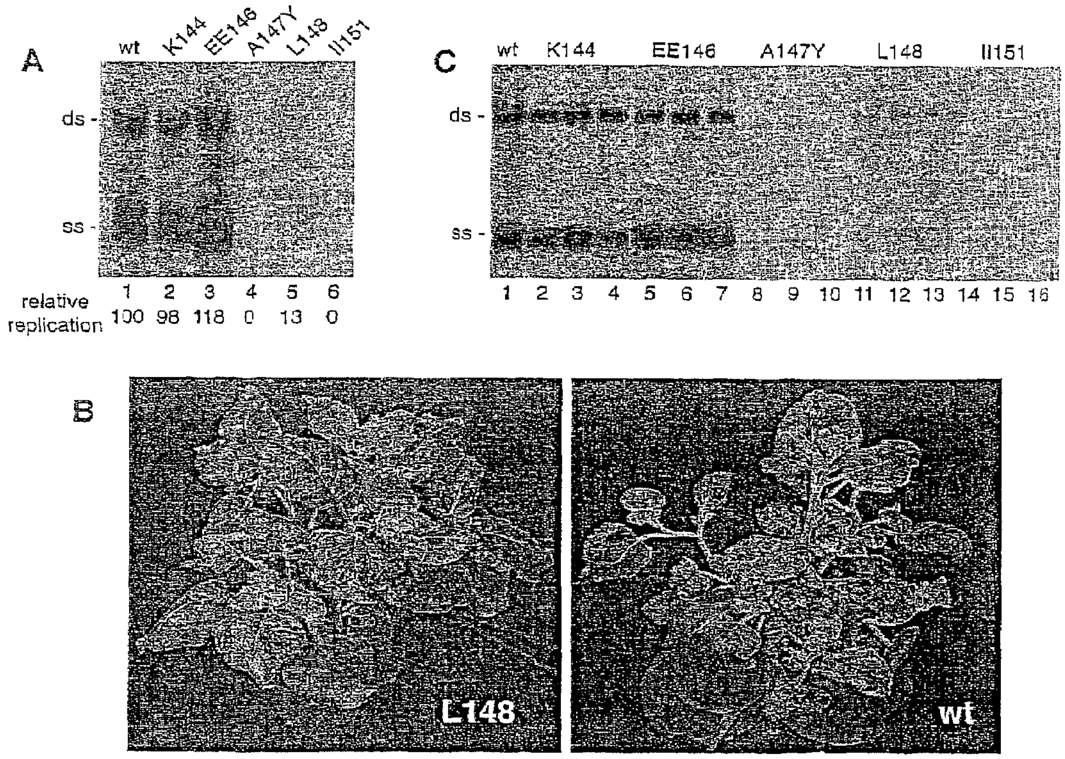
FIG. 9A shows that mutant L148 reduces replication and symptom severity. DNA replication of TGMV AL1 mutants was analyzed in tobacco protoplasts. Total DNA was isolated 72 hours post-transfection and analyzed by DNA gel blot hybridization using a radiolabeled TGMV A probe. Lanes 1-6 are transfections with TGMV A replicons with either wild type (lane 1) or mutant AL1 open reading frames corresponding to K144 (lane 2), EE146 (lane 3), A147Y (lane 4), L148 (lane 5), and II151 (lane 6). The positions of double (ds) and single (ss) stranded forms of TGMV A DNA are marked on the left. The relative accumulation of viral DNA is given at the bottom of each lane with wild type set at 100. No signal was detected in mutants A147Y and II151 even with longer exposures.
FIG. 9B shows that *N. benthamiana* plants infected with the pRBR-binding mutant L148 developed chlorosis along the veins but no leaf curling and stunting characteristic of wild type TGMV infection. These milder symptoms were maintained over a 5-week infection period.
FIG. 9C shows the results of *N. benthamiana* plants cobombarded with DNAs corresponding to TGMV A and B replicons. The AL1 open reading frames of the A components were either wild type (lane 1), or carried the K144 (lanes 2-4), EE146 (lanes 5-7), A147Y (lanes 8-10), L148 (lanes 11-13), or II151 (lanes 14-16) mutations. Total DNA (2.5 μg/lane) was isolated from young leaves of three plants for each construct at 14 days post-infection and analyzed on DNA gel blots. Viral DNA was detected using a radiolabeled probe specific for TGMV A.

Plant infection experiments were carried out by co-bombarding either wild type or mutant A component DNA with a TGMV B replicon onto *N. benthamiana* plants. Plants inoculated with the wild type virus developed clear symptoms by 6-7 days post-inoculation, exhibiting leaf curling, general chlorosis and stunting of new growth (FIG. 9B, wt). The K144, E145, E146 and EE146 mutants developed wild type symptoms with a similar timing (data not shown), indicating that these mutations do not visibly alter the infection process. In contrast, the L148 mutant produced milder symptoms that appeared 14-21 days post infection. L148-infected plants displayed no stunted growth or leaf curling, and only developed chlorosis along the veins (FIG. 9B, L148). These symptoms, which resemble those of KEE146-infected plants, were observed in all 12 inoculated plants and were maintained over a 5-week infection period. Mutants A147Y and II151 produced no detectable symptoms even at 5 weeks post-inoculation, consistent with their inability to replicate in tobacco protoplasts.

TGMV DNA accumulation was also examined in *N. benthamiana* plants inoculated with either wild type or mutant virus. Total DNA was isolated from systemically infected leaves 14 days post-inoculation and analyzed on DNA gel blots using a TGMV A probe. Viral DNA was detected in extracts of plants infected with all mutant viruses that produced symptoms (FIG. 9C), but not in asymptomatic plants inoculated with the A147Y (lanes 8-10) and II151 (lanes 14-16) mutants. Plants infected with K144 (FIG. 9C, lanes 2-4) or EE146 (lanes 5-7) contained wild type levels of single- and double-stranded viral DNA (lane 1). The same results were obtained with E145- and E146-infected plants. In contrast, both DNA forms were reduced in L148-inoculated plants relative to wild type (FIG. 9C, cf. lane 1 and 11-13). DNA gel blot analysis at 7, 14, and 21 days post inoculation showed that the differences in TGMV DNA levels between L148- and wild-type TGMV-infected plants are stable over time. A similar reduction in the accumulation of viral DNA was previously observed in plants infected with the KEE146 mutant. However, these earlier experiments established that there is not a direct relationship between attenuation of symptoms and reduction of virus DNA accumulation during infection. Instead, the attenuated symptoms caused by the L148 mutation are likely to be due to reduced RBR1 binding as has been hypothesized for KEE146.

Figure 10:
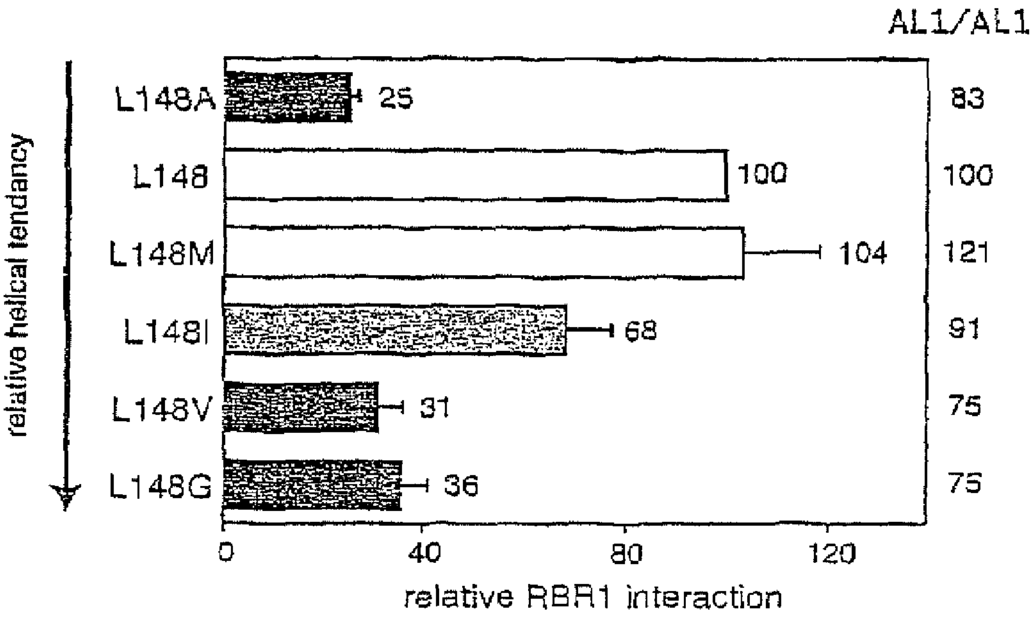
FIG. 10 shows that the ZmRBR1-binding activity of AL1 is differentially affected by substitutions at position 148. The ZmRBR1 214C cassette fused to the Gal4 DNA binding domain was co-transformed into yeast with Gal4 activation domain cassettes for either wild type (L148) or mutant AL1 coding sequences (on the left) and analyzed as described in FIG. 8B. The arrow indicates the relative α-helical tendency of each amino acid substitution (O'Neil et al., *Science* 250: 646-651 (1990)). Filled, hatched and open bars are as in FIG. 8. The effect of the mutations on AL1 oligomerization activity is indicated on the right.

Even though the phenotypes caused by the KEE146 and L148 mutations are very similar, the L148 mutation is the only single-site substitution in the RBR1 binding domain of AL1 that produced a clear effect. The role of L148 in AL1/RBR1 interactions was thus examined in greater detail. The L148 residue may facilitate RBR1 binding by contributing molecular contacts and/or by stabilizing the predicted structure of the Helix 4 motif. To address these possibilities, a series of amino acids were substituted at position L148 with different side chains and tendencies to occur in α-helices. The impact of the different mutations on the RBR1 binding and oligomerization activities of TGMV AL1 was analyzed in yeast dihybrid assays (FIG. 10). A L148M mutation had no detectable effect on RBR1 binding activity, whereas a L148I substitution resulted in a moderate reduction. Like the L148 mutant, the L148V and L148G mutants displayed significantly less RBR1 binding activity than wild type AL1. In general, the binding activities of the mutants declined with the probability of the substituted amino acid to occur in an α-helix (O'Neil et al., *Science* 250:646-51 (1990)). However, the low activity of the L148 mutant, which is predicted to readily form an α-helical structure, supports the involvement of side-chain contacts. Together, these results suggested that L148 contributes both structural and specific contacts to RBR1 binding. None of the mutations had a strong effect on AL1 oligomerization activity, indicating that the reduced RBR1 binding activities are not due to a general destabilization of AL1.

Figure 11:
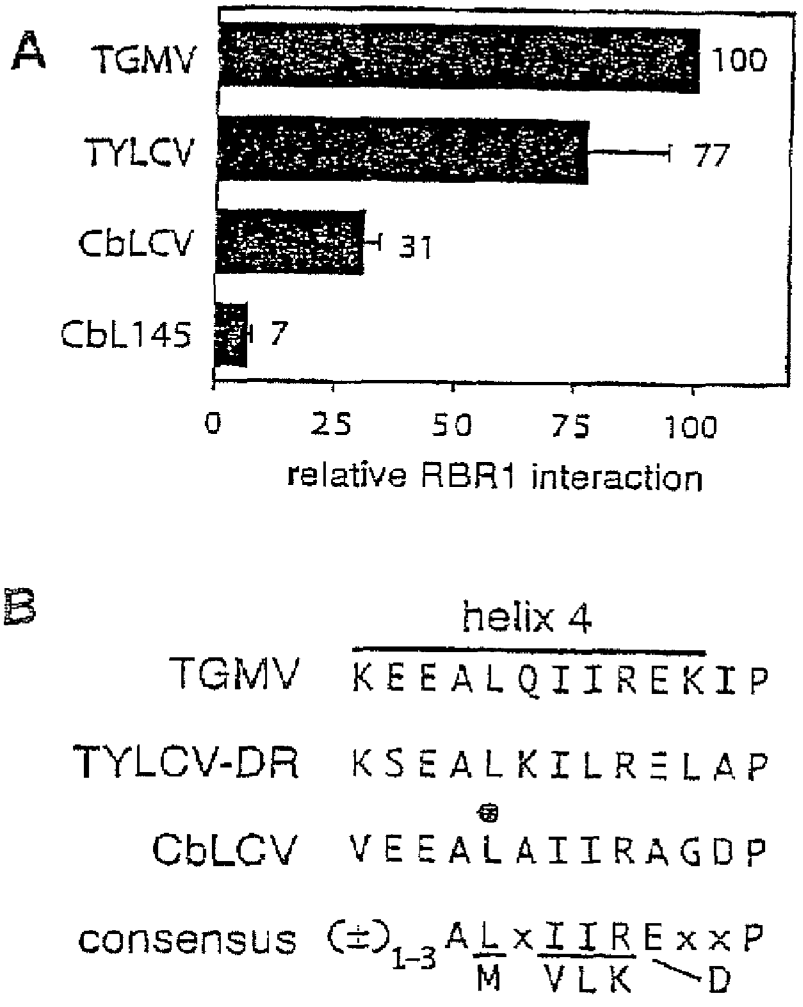
FIG. 11A shows how RBR1 interacts with the replication proteins of CbLCV and TYLCV. The ZmRBR1 214C cassette fused to the Gal4 DNA binding domain was co-transformed into yeast with Gal4 activation domain cassettes for either TGMV AL1, TYLCV C1, CbLCV AL1 or mutant CbLCV AL1 CbL148 (on the left). Protein interactions were assayed by measuring β-galactosidase activity in total protein extracts and normalized to wild type TGMV AL1 (100). The error bars correspond to two standard errors.
FIG. 11B shows the helix 4 motifs of TGMV AL1 (amino acids 144-156; SEQ ID NO:100), TYLCV-DR C1 (amino acids 142-154; SEQ ID NO:101) and CbLCV AL1 (amino acids 141-153; SEQ ID NO:102). The conserved leucine residue in the helix center that was mutated to an alanine in CbL145 is marked with a dot. A consensus for begomovirus AL1/C1 proteins is shown at the bottom (SEQ ID NO:113).

To determine if RBR1 binding is a general property of begomovirus replication proteins, the ability of C1/AL1 proteins of other begomoviruses to interact with RBR1 was examined. The studies employed two geminiviruses, tomato yellow leaf curl virus (Dominican Republic isolate; TYLCV-DR) and cabbage leaf curl virus (CbLCV), which are evolutionarily distant from TGMV and from each other. TYLCV-DR, which has a single genome component, is representative of Old World begomoviruses (Salati et al., *Phytopathology* 87:S84 (1997)). CbLCV is from a small group of New World begomoviruses whose AL1 proteins lack a highly conserved sequence of unknown function between the DNA cleavage motif III and the predicted Helix 3 (Hill et al., *Virology* 250: 283-292 (1998)). Gal4 AD fusions corresponding to full-length TYLCV C1 and CbLCV AL1 were generated and tested for interaction with a DBD-RBR1 fusion in yeast. The RBR1 binding activity of TYLCV C1 was similar to that detected for TGMV AL1 in parallel assays (FIG. 11A). In contrast, no colonies carrying the expression cassette corresponding to the CbLCV full-length AL1 fusion were recovered. Similar problems have been encountered in bacterial and insect cell systems with full-length CbLCV AL1, indicating that its expression is detrimental. To overcome this problem, a Gal4 AD fusion, corresponding to amino acids 2-178 of CbLCV AL1, was generated. Using this fusion, a reduced but significant level of RBR1 binding by the CbLCV AL1 N-terminus was detected (FIG. 11A).

The AL1/C1 sequences from 78 begomoviruses of both Old World and New World descent were compared to derive a consensus sequence for the Helix 4 motif (FIG. 11B). These comparisons revealed that the motif consists of a conserved hydrophobic core flanked by charged residues. The core includes an invariant alanine residue followed by a leucine in 67 of the examined AL1/C1 proteins and methionine in the remaining 11 proteins. The L/M position corresponds to L148 in TGMV and is represented by a leucine in both TYLCV and CbLCV. The substitution of an alanine at position L145 in CbLCV AL1 was examined for the ability to impair RBR1 binding analogous to the TGMV L148 mutant. The L145A mutation was introduced into Gal4 AD fusion vector carrying amino acids 2-178 of the CbLCV AL1 coding sequence and tested for RBR1 binding in yeast dihybrid assays. As shown in FIG. 11A, the CbL145A mutation caused a significant reduction in RBR binding activity. The CbLCV L145A and TGMV L148 mutations reduced RBR binding to 23% (FIG. 11A) and 25% (FIG. 8B) of their respective wild type controls. Together, these data show that diverse begomovirus replication proteins interact with RBR through a conserved motif.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

TABLE 1

TGMV Rep Retinoblastoma Binding Mutants and Phenotypes

| Rep Mutant (a) | Rep1 (b) | oligomer. (c) | Rep/Rb (d) | Repress (e) | Dom. Neg (f) |
|---|---|---|---|---|---|
| Ala1 (SEQ ID NO: 56) | neg. | 27 | 20 | 30 | + |
| Ala4 + 5 (SEQ ID NO: 78) | neg. | 88 | 45 | 322 | + |
| Ala6 (SEQ ID NO: 66) | neg. | 57 | 69 | 223 | + |
| Ala7 (SEQ ID NO: 68) | neg. | 0 | 31 | 234 | + |
| Ala13 (SEQ ID NO: 52) | neg. | 95 | 23 | 259 | + |
| Leu (SEQ ID NO: 76) | neg. | 30 | 8 | 206 | + |

TABLE 2

TGMV Rep Oligomerization Mutants and Phenotypes

| Rep Mutant (a) | Rep1 (b) | oligomer. (c) | Repress (e) | Dom. Neg. (f) |
|---|---|---|---|---|
| Ala13 (SEQ ID NO: 52) | neg. | 95 | 259 | + |
| Ala14 (SEQ ID NO: 54) | neg. | 67 | 328 | + |
| Ala1 (SEQ ID NO: 56) | neg. | 27 | 38 | + |
| Ala4 + 5 (SEQ ID NO: 78) | neg. | 88 | 322 | + |
| Ala6 (SEQ ID NO: 66) | neg. | 57 | 223 | + |
| Ala7 (SEQ ID NO: 68) | neg. | 0 | 234 | + |

TABLE 2-continued

TGMV Rep Oligomerization Mutants and Phenotypes

| Rep Mutant (a) | Rep1 (b) | oligomer. (c) | Repress (e) | Dom. Neg. (f) |
|---|---|---|---|---|
| Ala8 (SEQ ID NO: 70) | neg. | 102 | 212 | + |
| Ala9 (SEQ ID NO: 72) | neg. | 31 | 242 | + |

(a) Rep sequence mutations located in the TGMV AL1 region from amino acids 120-179 (see FIG. 1)
(b) Rep1 = the capacity for each mutant to support TGMV replication in tobacco protoplasts.
(c) oligomer. = the oligomerization activity of each mutant relative to wild type (100) in yeast dihybrid assays.
(d) Rep/Rb = the Rb binding activity of each mutant relative to wild type (100) in yeast dihybrid assays (maize Rb).
(e) Repress = the ability of each mutant to repress the AL1 promoter relative to wild type Rep (100) in tobacco protoplasts.
(f) Dom. Neg. = the capacity of each mutant to interfere with replication of wild type TGMV A component in tobacco protoplasts.

TABLE 3

| Name | Amino Acid substitution sites | SEQ. ID NO. |
|---|---|---|
| Alanine Substitutions | | |
| Ala1 | RS-R125 | 56 |
| Ala2 | QT130 | 58 |
| Ala3 | ND133 | 60 |
| Ala4 | E--N140 | 62 |
| Ala4 + 5 | E--N140 + KEE146 | 78 |
| Ala5 | KEE146 | 64 |
| Ala6 | REK154 | 66 |
| Ala7 | EKY159 | 68 |
| Ala8 | Q-HN165 | 70 |
| Ala9 | N-DR172 | 72 |
| Ala10 | K--E179 | 74 |
| Ala13 | FQ118 | 52 |
| Ala14 | D120 | 54 |
| Leucine Substitutions | | |
| Leu | AAA136 | 76 |

TABLE 4

AL1 Mutations

| Mutation | Oligonucleotide | SEQ ID NO: | Baculo-virus Vector | Yeast GAL4-AD | Plant Expression |
|---|---|---|---|---|---|
| Wt | N/A | | pMON1680 | pNSB809 | pMON1549 |
| FQ118 (Ala13) | CACTTCGACCGTCGACCGCGGCTTCTCCCCA | 26 | N/A | pNSB872 | pNSB866 |
| D120 (Ala14) | CACTTCGGCCGGCGACCGCGGCTTCTCCCCA | 27 | N/A | pNSB871 | pNSB865 |
| RS-R125 (Ala1) | GCAACCTCCTgcAGCggccgcACCGTCGACCTGGA | 28 | N/A | pNSB786 | pNSB695 |
| QT130 (Ala2) | CAGCGTCGTTgcaGcTgcGCAACCTCCTCTAGCA | 29 | N/A | pNSB788 | pNSB696 |
| ND133 (Ala3) | CTGCTGCAGCGgCcgcAGATGTTTGGCAA | 30 | pNSB603 | pNSB970 | pNSB670 |
| E--N140 (Ala4) | GGAAGAAGCAgcTAACGCggCcGCTGCAGCGTCGT | 31 | pNSB604 | ND | pNSB640 |
| KEE146 (Ala5) | TCTGCAGGGCTgCggCcgcGGAAGAAGCATTTAA | 32 | pNSB605 | ND | pNSB641 |
| REK154 (Ala6) | TTCTGGGATTgcggCcgcAATTATCTGCAGGG | 33 | pNSB605 | pNSB759 | pNSB671 |
| EKY159 (Ala7) | GAACTGAAATAAAgcggccgCTGGGATTTTCTCTC | 34 | pNSB607 | pNSB760 | pNSB672 |
| Q-HN165 (Ala8) | GCTATTTAGAgcGgcGAACgcAAATAAATATTTTTCTGGGAT | 35 | pNSB608 | pNSB761 | pNSB698 |
| N-DR172 (Ala9) | ATCAAATATCgcAgcTAgcgcGCTATTTAGATTGTG | 36 | pNSB609 | pNSB762 | pNSB707 |

TABLE 4-continued

AL1 Mutations

| Mutation | Oligonucleotide | SEQ ID NO: | Baculo-virus Vector | Yeast GAL4-AD | |
|---|---|---|---|---|---|
| K--E179 (Ala10) | GAAGCCATGGcgCcGGAGTCgcATCAAATATCC | 37 | pNSB610 | pNSB763 | pNSB697 |
| AAA136 (Leu) | GAAGCAATTTAAgGCCTCTagTagAagGTCGTTAGATG | 38 | pNSB743 | pNSB785 | pNSB676 |
| E--N140 + KEE146 (Ala4 + 5) | TCTGCAGGGCTgCggCcgcGGAAGAAGCAgcTAACGCggCcGCTGCAGCGTCGT | 39 | pNSB659 | pNSB757 | pNSB648 |
| | | | | | Viral Replicon |
| K144 | TCTGCAGGGCTTCTTCcgcGGAAGAAGCATTTAA | 40 | | pNSB916 | pNSB954 |
| E145 | TCTGCAGGGCcTCTgCTTTGGAAGAAGCATTTAA | 41 | | pNSB917 | |
| E146 | CTGCAGGGCTgCTTCTTTGGAAGAAGCA | 42 | | pNSB975 | |
| EE146 | TCTGCAGGGCggCcgCTTTGGAAGAAGCATTTAAC | 43 | | pNSB1040 | pNSB1032 |
| A147Y | TAATTATCTGaAGGtaTTCTTCTTTGGAAGAAGCATTTAA | 44 | | pNSB1003 | pNSB999 |
| L148 | TAATTATCTGCgcaGCTTCTTCTTTGGAAGAAGCATTTAA | 45 | | pNSB1001 | pNSB997 |
| L148V | ATTATCTGCAcGGCcTCTTCTTTGGAAGAAGCATTTAA | 46 | | pNSB980 | pNSB979 |
| L148V* | TAATTATCTGaAcGGCTTCTTCTTTGGAAGAAGCATTTAAC | | | pNSB1039 | pNSB1030 |
| L148G | CTAATTATCTGgccGGCTTCTTCTTTGGAAGAAGCATTTA | 47 | | pNSB1004 | pNSB1000 |
| II151 | TTTCTCTCTAgcTgcCTGaAGGGCTTCTTCTTTGGAAGA | 48 | | pNSB1002 | pNSB998 |

TABLE 5

Constructs

| Mutation | Mutagenesis oligonucleotides | SEQ ID NO: | Yeast dihybrid vectors GAL4-AD-AL1 | GAL4-BD | Viral Replicons |
|---|---|---|---|---|---|
| TGMV AL1 | | | pNSB809 | pNSB736 | pMON1565 |
| KEE146 | | | pNSB894 | | |
| K144 | TCTGCAGGGCTTCTTCcgcGGAAGAAGCATTTAA | 40 | pNSB916 | | pNSB954 |
| E145 | TCTGCAGGGCcTCTgCTTTGGAAGAAGCATTTAA | 41 | pNSB917 | | |
| E146 | CTGCAGGGCTgCTTCTTTGGAAGAAGCA | 42 | pNSB975 | | |
| EE146 | TCTGCAGGGCggCcgCTTTGGAAGAAGCATTTAAC | 43 | pNSB1040 | | pNSB1032 |
| A147Y | TAATTATCTGaAGGtaTTCTTCTTTGGAAGAAGCATTTAA | 44 | pNSB1003 | | pNSB999 |
| L148 | TAATTATCTGCgcaGCTTCTTCTTTGGAAGAAGCATTTAA | 45 | pNSB1001 | | pNSB997 |
| L148V | ATTATCTGCAcGGCcTCTTCTTTGGAAGAAGCATTTAA | 46 | pNSB980 | | pNSB979 |
| L148V* | TAATTATCTGaAcGGCTTCTTCTTTGGAAGAAGCATTTAAC | 47 | pNSB1039 | | pNSB1030 |
| L148M | pNSB979 revertant | | pNSB1112 | | |
| L148G | CTAATTATCTGgccGGCTTCTTCTTTGGAAGAAGCATTTA | 48 | pNSB1004 | | pNSB1000 |
| L148I | pNSB1030 revertant | | pNSB1079 | | |
| II-150-AA | TTTCTCTCTAgcTgcCTGaAGGGCTTCTTCTTTGGAAGA | 49 | pNSB1002 | | pNSB998 |
| REK154 | | | pNSB759 | | |
| CbLCV AL1 | | | pNSB901 | pNSB909 | |
| Cb1-207 | | | pNSB974 | | |

TABLE 5-continued

| Constructs | | | | | |
|---|---|---|---|---|---|
| | | SEQ ID | Yeast dihybrid vectors | | Viral |
| Mutation | Mutagenesis oligonucleotides | NO: | GAL4-AD-AL1 | GAL4-BD | Replicons |
| Cb1-207, L145A | GTGTGGAAGAGGCGgccGCAATTATAAGGGC | 106 | pNSB1114 | | |
| TYLCV-DR C1 | | | pTYLC102 | pTYLC103 | |
| Maize RBR1 | | | | 214C | |

What is claimed is:

1. A plant comprising transformed plant cells, said transformed plant cells comprising a heterologous nucleic acid construct comprising a nucleotide sequence encoding the amino acid sequence of SEQ ID NO:101 having a mutation of a leucine to an alanine at amino acid position number five, and the nucleotide sequence of SEQ ID NO:26.

2. The plant of claim 1, wherein said plant has increased tolerance or resistance to infection by a geminivirus as compared to a plant lacking said heterologous nucleic acid construct.

3. The plant of claim 2, wherein said plant has increased tolerance or resistance to infection by a geminivirus selected from the group consisting of tomato golden mosaic virus, tomato mottle virus, tomato yellow leaf curl virus, tomato leaf curl virus, African cassava mosaic virus, Indian cassava mosaic virus, potato yellow mosaic virus, bean golden mosaic virus, bean dwarf mosaic virus, squash leaf curl virus, Texas pepper virus, cotton leaf curl virus and beet curly top virus.

4. A plant according to claim 1, wherein said plant is selected from the group consisting of tomato, cassava, potato, bean, squash and beet.

5. A plant according to claim 1, wherein said plant is of the family Solanaceae.

6. A plant according to claim 1, wherein said plant is a tomato plant and has increased resistance or tolerance to infection by tomato yellow leaf curl virus (TYLCV).

7. A method of combating geminivirus infection in an agricultural field, comprising planting the field with a crop of plants according to claim 1.

8. A method of making the transgenic plant of claim 1, comprising:

a) transforming a plant cell with a heterologous nucleic acid construct comprising a nucleotide sequence encoding the amino acid sequence of SEQ ID NO:101 having a mutation of a leucine to an alanine at amino acid position number five, and a nucleotide sequence of SEQ ID NO:26; and b) regenerating the transgenic plant from said transformed plant cell.

9. An isolated nucleic acid construct comprising a nucleotide sequence encoding a rep protein, wherein said nucleotide sequence encodes the amino acid sequence of SEQ ID NO:101 having a mutation of a leucine to an alanine at amino acid position number five.

10. The nucleic acid construct of claim 9, further comprising the nucleotide sequence of SEQ ID NO:26 (Ala13).

11. A vector comprising the nucleic acid construct of claim 9.

12. A vector comprising the nucleic acid construct of claim 10.

13. A cell comprising the vector of claim 11.

14. A cell comprising the vector of claim 12.

15. Seed or progeny of the plant of claim 1, which seed or progeny comprises said nucleic acid construct.

* * * * *

UNITED STATES PATENT AND TRADEMARK OFFICE

CERTIFICATE OF CORRECTION

PATENT NO. : 8,039,688 B2
APPLICATION NO. : 12/433085
DATED : October 18, 2011
INVENTOR(S) : Hanley-Bowdoin et al.

It is certified that error appears in the above-identified patent and that said Letters Patent is hereby corrected as shown below:

In the Patent:

Column 26, Line 48: Please correct “and 11151” to read -- and II151 --

Signed and Sealed this
Twenty-seventh Day of March, 2012

David J. Kappos
*Director of the United States Patent and Trademark Office*

SEQUENCE LISTING

<160> NUMBER OF SEQ ID NOS: 113

<210> SEQ ID NO 1
<211> LENGTH: 352
<212> TYPE: PRT
<213> ORGANISM: Tomato golden mosaic virus

<400> SEQUENCE: 1

Met Pro Ser His Pro Lys Arg Phe Gln Ile Asn Ala Lys Asn Tyr Phe
1 5 10 15

Leu Thr Tyr Pro Gln Cys Ser Leu Ser Lys Glu Glu Ser Leu Ser Gln
20 25 30

Leu Gln Ala Leu Asn Thr Pro Ile Asn Lys Lys Phe Ile Lys Ile Cys
35 40 45

Arg Glu Leu His Glu Asp Gly Gln Pro His Leu His Val Leu Ile Gln
50 55 60

Phe Glu Gly Lys Tyr Cys Cys Gln Asn Gln Arg Phe Phe Asp Leu Val
65 70 75 80

Ser Pro Thr Arg Ser Ala His Phe His Pro Asn Ile Gln Arg Ala Lys
85 90 95

Ser Ser Ser Asp Val Lys Thr Tyr Ile Asp Lys Asp Gly Asp Thr Leu
100 105 110

Val Trp Gly Glu Phe Gln Val Asp Gly Arg Ser Ala Arg Gly Gly Cys
115 120 125

Gln Thr Ser Asn Asp Ala Ala Ala Glu Ala Leu Asn Ala Ser Ser Lys
130 135 140

Glu Glu Ala Leu Gln Ile Ile Arg Glu Lys Ile Pro Glu Lys Tyr Leu
145 150 155 160

Phe Gln Phe His Asn Leu Asn Ser Asn Leu Asp Arg Ile Phe Asp Lys
165 170 175

Thr Pro Glu Pro Trp Leu Pro Pro Phe His Val Ser Ser Phe Thr Asn
180 185 190

Val Pro Asp Glu Met Arg Gln Trp Ala Glu Asn Tyr Phe Gly Lys Ser
195 200 205

Ser Ala Ala Arg Pro Glu Arg Pro Ile Ser Ile Ile Glu Gly Asp
210 215 220

Ser Arg Thr Gly Lys Thr Met Trp Ala Arg Ser Leu Gly Pro His Asn
225 230 235 240

Tyr Leu Ser Gly His Leu Asp Leu Asn Ser Arg Val Tyr Ser Asn Lys
245 250 255

Val Glu Tyr Asn Val Ile Asp Asp Val Thr Pro Gln Tyr Leu Lys Leu
260 265 270

Lys His Trp Lys Glu Leu Ile Gly Ala Gln Arg Asp Trp Gln Thr Asn

```
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 2
<211> LENGTH: 70
<212> TYPE: PRT
<213> ORGANISM: Tomato golden mosaic virus
<220> FEATURE:
<221> NAME/KEY: MISC_FEATURE
<222> LOCATION: (1)..(70)
<223> OTHER INFORMATION: Wild-type TGMV AL1 amino acids 111-180

<400> SEQUENCE: 2

Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70


<210> SEQ ID NO 3
<211> LENGTH: 70
<212> TYPE: PRT
<213> ORGANISM: Tomato golden mosaic virus
<220> FEATURE:
<221> NAME/KEY: MISC_FEATURE
<222> LOCATION: (12)..(15)
<223> OTHER INFORMATION: RS-R125 (Ala1) mutation

<400> SEQUENCE: 3

Thr Leu Val Trp Gly Glu Phe Gln Val Asp Gly Ala Ala Ala Ala Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70


<210> SEQ ID NO 4
<211> LENGTH: 70
<212> TYPE: PRT
<213> ORGANISM: Tomato golden mosaic virus
<220> FEATURE:
<221> NAME/KEY: MICS_FEATURE
<222> LOCATION: (27)..(36)
<223> OTHER INFORMATION: E--N140 + KEE146 (Ala4+5) mutation

<400> SEQUENCE: 4
```

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Ala Ala Leu Ala Ala Ser
            20                  25                  30

Ser Ala Ala Ala Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70


<210> SEQ ID NO 5
<211> LENGTH: 70
<212> TYPE: PRT
<213> ORGANISM: Tomato golden mosaic virus
<220> FEATURE:
<221> NAME/KEY: MISC_FEATURE
<222> LOCATION: (42)..(44)
<223> OTHER INFORMATION: REK154 (Ala6) mutation

<400> SEQUENCE: 5

Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Ala Ala Ala Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70


<210> SEQ ID NO 6
<211> LENGTH: 70
<212> TYPE: PRT
<213> ORGANISM: Tomato golden mosaic virus
<220> FEATURE:
<221> NAME/KEY: MISC_FEATURE
<222> LOCATION: (47)..(49)
<223> OTHER INFORMATION: EKY159 (Ala7) mutation

<400> SEQUENCE: 6

Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Ala Ala
        35                  40                  45

Ala Leu Phe Gln Phe His Asn Leu Asn Ser Asn Leu Asp Arg Ile Phe
    50                  55                  60

Asp Lys Thr Pro Glu Pro
65                  70


<210> SEQ ID NO 7
<211> LENGTH: 70
<212> TYPE: PRT
<213> ORGANISM: Tomato golden mosaic virus
<220> FEATURE:
<221> NAME/KEY: MISC_FEATURE
<222> LOCATION: (52)..(55)
<223> OTHER INFORMATION: Q-HN165 (Ala8) mutation

<400> SEQUENCE: 7
```

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Ala Phe Ala Ala Leu Asn Ser Asn Leu Asp Arg Ile Phe
    50                  55                  60

Asp Lys Thr Pro Glu Pro
65                  70


<210> SEQ ID NO 8
<211> LENGTH: 70
<212> TYPE: PRT
<213> ORGANISM: Tomato golden mosaic virus
<220> FEATURE:
<221> NAME/KEY: MISC_FEATURE
<222> LOCATION: (59)..(62)
<223> OTHER INFORMATION: N-DR172 (Ala9) mutation

<400> SEQUENCE: 8

Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Ala Leu Ala Ala Ile Phe
    50                  55                  60

Asp Lys Thr Pro Glu Pro
65                  70


<210> SEQ ID NO 9
<211> LENGTH: 70
<212> TYPE: PRT
<213> ORGANISM: Tomato golden mosaic virus
<220> FEATURE:
<221> NAME/KEY: MISC_FEATURE
<222> LOCATION: (7)..(8)
<223> OTHER INFORMATION: FQ118 (Ala13) mutation

<400> SEQUENCE: 9

Thr Leu Val Trp Gly Glu Ala Ala Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70


<210> SEQ ID NO 10
<211> LENGTH: 70
<212> TYPE: PRT
<213> ORGANISM: Tomato golden mosaic virus
<220> FEATURE:
<221> NAME/KEY: MISC_FEATURE
<222> LOCATION: (10)..(10)
<223> OTHER INFORMATION: D120 (Ala14) mutation
```

<400> SEQUENCE: 10

Thr Leu Val Trp Gly Glu Phe Gln Val Ala Gly Arg Ser Ala Arg Gly
1 5 10 15

Gly Cys Gln Thr Ser Asn Asp Ala Ala Ala Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 11
<211> LENGTH: 70
<212> TYPE: PRT
<213> ORGANISM: Tomato golden mosaic virus
<220> FEATURE:
<221> NAME/KEY: MISC_FEATURE
<222> LOCATION: (24)..(26)
<223> OTHER INFORMATION: AAA136 (Leu) mutation

<400> SEQUENCE: 11

Thr Leu Val Trp Gly Glu Phe Gln Val Asp Gly Arg Ser Ala Arg Gly
1 5 10 15

Gly Cys Gln Thr Ser Asn Asp Leu Leu Leu Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 12
<211> LENGTH: 70
<212> TYPE: PRT
<213> ORGANISM: Tomato golden mosaic virus
<220> FEATURE:
<221> NAME/KEY: MISC_FEATURE
<222> LOCATION: (19)..(20)
<223> OTHER INFORMATION: QT130 (Ala2) mutation

<400> SEQUENCE: 12

Thr Leu Val Trp Gly Glu Phe Gln Val Asp Gly Arg Ser Ala Arg Gly
1 5 10 15

Gly Cys Ala Ala Ser Asn Asp Ala Ala Ala Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 13
<211> LENGTH: 70
<212> TYPE: PRT
<213> ORGANISM: Tomato golden mosaic virus
<220> FEATURE:
<221> NAME/KEY: MISC_FEATURE
<222> LOCATION: (22)..(23)
<223> OTHER INFORMATION: ND133 (Ala3) mutation

<400> SEQUENCE: 13

Thr Leu Val Trp Gly Glu Phe Gln Val Asp Gly Arg Ser Ala Arg Gly
1 5 10 15

Gly Cys Gln Thr Ser Ala Ala Ala Ala Ala Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 14
<211> LENGTH: 70
<212> TYPE: PRT
<213> ORGANISM: Tomato golden mosaic virus
<220> FEATURE:
<221> NAME/KEY: MISC_FEATURE
<222> LOCATION: (27)..(30)
<223> OTHER INFORMATION: E--N140 (Ala4) mutation

<400> SEQUENCE: 14

Thr Leu Val Trp Gly Glu Phe Gln Val Asp Gly Arg Ser Ala Arg Gly
1 5 10 15

Gly Cys Gln Thr Ser Asn Asp Ala Ala Ala Ala Ala Leu Ala Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 15
<211> LENGTH: 70
<212> TYPE: PRT
<213> ORGANISM: Tomato golden mosaic virus
<220> FEATURE:
<221> NAME/KEY: MISC_FEATURE
<222> LOCATION: (34)..(36)
<223> OTHER INFORMATION: KEE146 (Ala5) mutation

<400> SEQUENCE: 15

Thr Leu Val Trp Gly Glu Phe Gln Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Ala Ala Ala Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 16
<211> LENGTH: 70
<212> TYPE: PRT
<213> ORGANISM: Tomato golden mosaic virus
<220> FEATURE:
<221> NAME/KEY: MISC_FEATURE
<222> LOCATION: (66)..(69)

<223> OTHER INFORMATION: K--E179 (Ala10) mutation

<400> SEQUENCE: 16

Thr Leu Val Trp Gly Glu Phe Gln Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Lys Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Ala Thr Pro Ala Pro
65 70

<210> SEQ ID NO 17
<211> LENGTH: 70
<212> TYPE: PRT
<213> ORGANISM: Tomato golden mosaic virus
<220> FEATURE:
<221> NAME/KEY: MISC_FEATURE
<222> LOCATION: (34)..(34)
<223> OTHER INFORMATION: K144 mutation

<400> SEQUENCE: 17

Thr Leu Val Trp Gly Glu Phe Gln Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Ala Glu Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 18
<211> LENGTH: 70
<212> TYPE: PRT
<213> ORGANISM: Tomato golden mosaic virus
<220> FEATURE:
<221> NAME/KEY: MISC_FEATURE
<222> LOCATION: (35)..(35)
<223> OTHER INFORMATION: E145 mutation

<400> SEQUENCE: 18

Thr Leu Val Trp Gly Glu Phe Gln Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Lys Ala Glu Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 19
<211> LENGTH: 70
<212> TYPE: PRT
<213> ORGANISM: Tomato golden mosaic virus
<220> FEATURE:
<221> NAME/KEY: MISC_FEATURE -continued
<222> LOCATION: (36)..(36)
<223> OTHER INFORMATION: E146 mutation

<400> SEQUENCE: 19

Thr Leu Val Trp Gly Glu Phe Gln Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Lys Glu Ala Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 20
<211> LENGTH: 70
<212> TYPE: PRT
<213> ORGANISM: Tomato golden mosaic virus
<220> FEATURE:
<221> NAME/KEY: MISC_FEATURE
<222> LOCATION: (35)..(36)
<223> OTHER INFORMATION: EE146 mutation

<400> SEQUENCE: 20

Thr Leu Val Trp Gly Glu Phe Gln Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Lys Ala Ala Ala Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 21
<211> LENGTH: 70
<212> TYPE: PRT
<213> ORGANISM: Tomato golden mosaic virus
<220> FEATURE:
<221> NAME/KEY: MISC_FEATURE
<222> LOCATION: (37)..(37)
<223> OTHER INFORMATION: A147Y mutation

<400> SEQUENCE: 21

Thr Leu Val Trp Gly Glu Phe Gln Val Asp Gly Arg Ser Ala Arg Gly
1 5 10 15

Gly Cys Gln Thr Ser Asn Asp Ala Ala Ala Glu Ala Leu Asn Ala Ser
20 25 30

Ser Lys Glu Glu Tyr Leu Gln Ile Ile Arg Glu Lys Ile Pro Glu Lys
35 40 45

Tyr Leu Phe Gln Phe His Asn Leu Asn Ser Asn Leu Asp Arg Ile Phe
50 55 60

Asp Lys Thr Pro Glu Pro
65 70

<210> SEQ ID NO 22
<211> LENGTH: 70
<212> TYPE: PRT
<213> ORGANISM: Tomato golden mosaic virus
<220> FEATURE:

<221> NAME/KEY: MISC_FEATURE
<222> LOCATION: (38)..(38)
<223> OTHER INFORMATION: L148 mutation

<400> SEQUENCE: 22

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Ala Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 23
<211> LENGTH: 70
<212> TYPE: PRT
<213> ORGANISM: Tomato golden mosaic virus
<220> FEATURE:
<221> NAME/KEY: MISC_FEATURE
<222> LOCATION: (38)..(38)
<223> OTHER INFORMATION: L148V and L148V* mutations

<400> SEQUENCE: 23

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Val Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 24
<211> LENGTH: 70
<212> TYPE: PRT
<213> ORGANISM: Tomato golden mosaic virus
<220> FEATURE:
<221> NAME/KEY: MISC_FEATURE
<222> LOCATION: (38)..(38)
<223> OTHER INFORMATION: L148G mutation

<400> SEQUENCE: 24

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Gly Gln Ile Ile Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 25
<211> LENGTH: 70
<212> TYPE: PRT
<213> ORGANISM: Tomato golden mosaic virus -continued
<220> FEATURE:
<221> NAME/KEY: MISC_FEATURE
<222> LOCATION: (40)..(41)
<223> OTHER INFORMATION: II151 mutation

<400> SEQUENCE: 25

```
Thr Leu Val Trp Gly Glu Phe Gln Val Asp Gly Arg Ser Ala Arg Gly
1               5                   10                  15

Gly Cys Gln Thr Ser Asn Asp Ala Ala Ala Glu Ala Leu Asn Ala Ser
            20                  25                  30

Ser Lys Glu Glu Ala Leu Gln Ala Ala Arg Glu Lys Ile Pro Glu Lys
        35                  40                  45

Tyr Leu Phe Gln Phe His Asn Leu Asn Ser Asn Leu Asp Arg Ile Phe
    50                  55                  60

Asp Lys Thr Pro Glu Pro
65                  70
```

<210> SEQ ID NO 26
<211> LENGTH: 31
<212> TYPE: DNA
<213> ORGANISM: Artificial sequence
<220> FEATURE:
<223> OTHER INFORMATION: Mutagenesis oligonucleotide for FQ118 (Ala13)

<400> SEQUENCE: 26
cacttcgacc gtcgaccgcg gcttctcccc a 31

<210> SEQ ID NO 27
<211> LENGTH: 31
<212> TYPE: DNA
<213> ORGANISM: Artificial sequence
<220> FEATURE:
<223> OTHER INFORMATION: Mutagenesis oligonucleotide for D120 (Ala14)

<400> SEQUENCE: 27
cacttcggcc ggcgaccgcg gcttctcccc a 31

<210> SEQ ID NO 28
<211> LENGTH: 35
<212> TYPE: DNA
<213> ORGANISM: Artificial sequence
<220> FEATURE:
<223> OTHER INFORMATION: Mutagenesis oligonucleotide for RS-R125 (Ala1)

<400> SEQUENCE: 28
gcaacctcct gcagcggccg caccgtcgac ctgga 35

<210> SEQ ID NO 29
<211> LENGTH: 35
<212> TYPE: DNA
<213> ORGANISM: Artificial sequence
<220> FEATURE:
<223> OTHER INFORMATION: Mutagenesis oligonucleotide for QT130 (Ala2)

<400> SEQUENCE: 29
cagcgtcgtt gctagctgcg caacctcctc tagca 35

<210> SEQ ID NO 30
<211> LENGTH: 29
<212> TYPE: DNA
<213> ORGANISM: Artificial sequence
<220> FEATURE:
<223> OTHER INFORMATION: Mutagenesis oligonucleotide for ND133 (Ala3)

<400> SEQUENCE: 30
ctgctgcagc ggccgcagat gtttggcaa 29

<210> SEQ ID NO 31
<211> LENGTH: 35
<212> TYPE: DNA
<213> ORGANISM: Artificial sequence
<220> FEATURE:
<223> OTHER INFORMATION: Mutagenesis oligonucleotide for E--N140 (Ala4)

<400> SEQUENCE: 31
ggaagaagca gctaacgcgg ccgctgcagc gtcgt 35

<210> SEQ ID NO 32
<211> LENGTH: 35
<212> TYPE: DNA
<213> ORGANISM: Artificial sequence
<220> FEATURE:
<223> OTHER INFORMATION: Mutagenesis oligonucleotide for KEE146 (Ala5)

<400> SEQUENCE: 32
cagcgtcgtt agcagctgcg caacctcctc tagca 35

<210> SEQ ID NO 33
<211> LENGTH: 32
<212> TYPE: DNA
<213> ORGANISM: Artificial sequence
<220> FEATURE:
<223> OTHER INFORMATION: Mutagenesis oligonucleotide for REK154 (Ala6)

<400> SEQUENCE: 33
ttctgggatt gcggccgcaa ttatctgcag gg 32

<210> SEQ ID NO 34
<211> LENGTH: 35
<212> TYPE: DNA
<213> ORGANISM: Artificial sequence
<220> FEATURE:
<223> OTHER INFORMATION: Mutagenesis oligonucleotide for EKY159 (Ala7)

<400> SEQUENCE: 34
gaactgaaat aaagcggccg ctgggatttt ctctc 35

<210> SEQ ID NO 35
<211> LENGTH: 42
<212> TYPE: DNA
<213> ORGANISM: Artificial sequence
<220> FEATURE:
<223> OTHER INFORMATION: Mutagenesis oligonucleotide for Q-HN165 (Ala8)

<400> SEQUENCE: 35
gctatttaga gcggcgaacg caaataaata tttttctggg at 42

<210> SEQ ID NO 36
<211> LENGTH: 36
<212> TYPE: DNA
<213> ORGANISM: Artificial sequence
<220> FEATURE:
<223> OTHER INFORMATION: Mutagenesis oligonucleotide for N-DR172 (Ala9)

<400> SEQUENCE: 36
atcaaatatc gcagctagcg cgctatttag attgtg 36

<210> SEQ ID NO 37
<211> LENGTH: 33
<212> TYPE: DNA
<213> ORGANISM: Artificial sequence
<220> FEATURE:

<223> OTHER INFORMATION: Mutagenesis oligonucleotide for K--E179 (Ala10)

<400> SEQUENCE: 37
gaagccatgg cgccggagtc gcatcaaata tcc 33

<210> SEQ ID NO 38
<211> LENGTH: 37
<212> TYPE: DNA
<213> ORGANISM: Artificial sequence
<220> FEATURE:
<223> OTHER INFORMATION: Mutagenesis oligonucleotide for AAA136 (Leu)

<400> SEQUENCE: 38
gaagcattta aggcctctag tagaaggtcg ttagatg 37

<210> SEQ ID NO 39
<211> LENGTH: 54
<212> TYPE: DNA
<213> ORGANISM: Artificial sequence
<220> FEATURE:
<223> OTHER INFORMATION: Mutagenesis oligonucleotide for E--N140 +
KEE146 (Ala4+5)

<400> SEQUENCE: 39
tctgcagggc tgcggccgcg gaagaagcag ctaacgcggc cgctgcagcg tcgt 54

<210> SEQ ID NO 40
<211> LENGTH: 34
<212> TYPE: DNA
<213> ORGANISM: Artificial sequence
<220> FEATURE:
<223> OTHER INFORMATION: Mutagenesis oligonucleotide for K144

<400> SEQUENCE: 40
tctgcagggc ttcttccgcg gaagaagcat ttaa 34

<210> SEQ ID NO 41
<211> LENGTH: 34
<212> TYPE: DNA
<213> ORGANISM: Artificial sequence
<220> FEATURE:
<223> OTHER INFORMATION: Mutagenesis oligonucleotide for E145

<400> SEQUENCE: 41
tctgcagggc ctctgctttg gaagaagcat ttaa 34

<210> SEQ ID NO 42
<211> LENGTH: 28
<212> TYPE: DNA
<213> ORGANISM: Artificial sequence
<220> FEATURE:
<223> OTHER INFORMATION: Mutagenesis oligonucleotide for E146

<400> SEQUENCE: 42
ctgcagggct gcttctttgg aagaagca 28

<210> SEQ ID NO 43
<211> LENGTH: 35
<212> TYPE: DNA
<213> ORGANISM: Artificial sequence
<220> FEATURE:
<223> OTHER INFORMATION: Mutagenesis oligonucleotide for EE146

<400> SEQUENCE: 43
tctgcagggc ggccgctttg gaagaagcat ttaac 35

<210> SEQ ID NO 44
<211> LENGTH: 40
<212> TYPE: DNA
<213> ORGANISM: Artificial sequence
<220> FEATURE:
<223> OTHER INFORMATION: Mutagenesis oligonucleotide for A147Y

<400> SEQUENCE: 44
taattatctg aaggtattct tctttggaag aagcatttaa 40

<210> SEQ ID NO 45
<211> LENGTH: 40
<212> TYPE: DNA
<213> ORGANISM: Artificial sequence
<220> FEATURE:
<223> OTHER INFORMATION: Mutagenesis oligonucleotide for L148

<400> SEQUENCE: 45
taattatctg cgcagcttct tctttggaag aagcatttaa 40

<210> SEQ ID NO 46
<211> LENGTH: 38
<212> TYPE: DNA
<213> ORGANISM: Artificial sequence
<220> FEATURE:
<223> OTHER INFORMATION: Mutagenesis oligonucleotide for L148V

<400> SEQUENCE: 46
attatctgca cggcctcttc tttggaagaa gcatttaa 38

<210> SEQ ID NO 47
<211> LENGTH: 41
<212> TYPE: DNA
<213> ORGANISM: Artificial sequence
<220> FEATURE:
<223> OTHER INFORMATION: Mutagenesis oligonucleotide for L148V*

<400> SEQUENCE: 47
taattatctg aacggcttct tctttggaag aagcatttaa c 41

<210> SEQ ID NO 48
<211> LENGTH: 40
<212> TYPE: DNA
<213> ORGANISM: Artificial sequence
<220> FEATURE:
<223> OTHER INFORMATION: Mutagenesis oligonucleotide for L148G

<400> SEQUENCE: 48
ctaattatct ggccggcttc ttctttggaa gaagcattta 40

<210> SEQ ID NO 49
<211> LENGTH: 39
<212> TYPE: DNA
<213> ORGANISM: Artificial sequence
<220> FEATURE:
<223> OTHER INFORMATION: Mutagenesis oligonucleotide for II151

<400> SEQUENCE: 49
tttctctcta gctgcctgaa gggcttcttc tttggaaga 39

<210> SEQ ID NO 50
<211> LENGTH: 1056
<212> TYPE: DNA
<213> ORGANISM: Tomato golden mosaic virus
<220> FEATURE:
<221> NAME/KEY: misc_feature
<222> LOCATION: (1)..(1056)
<223> OTHER INFORMATION: TGMV AL1 coding sequence

<400> SEQUENCE: 50

```
atgccatcgc atccaaaacg gtttcaaata aatgccaaaa attattttct tacatatcct      60
cagtgctcct tgtccaaaga agaatcactt tctcaattac aagccctaaa cactccgatt     120
aacaaaaaat tcataaaaat ctgcagagag cttcatgaag atgggcaacc tcacctccac     180
gtgcttattc agttcgaggg aaaatactgc tgccaaaatc aacgattctt cgacctggta     240
tccccaacaa ggtcagcaca tttccatcca aacattcaga gagctaaatc gtcttccgac     300
gtcaagacgt acatcgacaa agacggagat actcttgtat ggggagaatt ccaggtcgac     360
ggtcgaagtg ctagaggagg ttgccaaaca tctaacgacg ctgcagcaga ggcgttaaat     420
gcttcttcca aagaagaagc cctgcagata attagagaga aaatcccaga aaaatattta     480
tttcagttcc acaatctaaa tagcaattta gataggatat ttgataagac tcctgaacca     540
tggcttcctc cgttccacgt ctcatcattt actaacgtgc cagacgagat gagacaatgg     600
gctgaaaatt attttggaaa gagttccgct gcgcggccgg agagacctat tagtattatc     660
atcgagggcg atagtcggac gggaaagact atgtgggctc gttcactagg cccacataat     720
tatttgagcg ggcatttgga tctcaattct agggtttact caaacaaggt tgagtataac     780
gtcatcgatg atgtcacacc gcaatatcta aagttgaaac attggaaaga actcattggg     840
gcccaaagag attggcagac taactgtaaa tacggaaagc cagttcaaat taaaggaggt     900
atcccgtcaa tcgtgctgtg caatcctgga gagggtgcta gctataaagt tttcctcgac     960
aaagaggaaa acactccact aaagaactgg actttccata atgcgaaatt cgtcttcctc    1020
aactcccccc tctatcaaag ctcaacacag agcagc                             1056
```

<210> SEQ ID NO 51
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 FQ118 mutant (Ala13)

<400> SEQUENCE: 51

```
atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa gcc gcg gtc gac ggt cga agt gct aga gga ggt tgc      384
```

```
Val Trp Gly Glu Ala Ala Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 52
<211> LENGTH: 352
<212> TYPE: PRT
<213> ORGANISM: Tomato golden mosaic virus

<400> SEQUENCE: 52

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
```

```
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Ala Ala Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 53
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 D120 (Ala14) mutant

<400> SEQUENCE: 53

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60
```

```
ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa gcc gcg gtc gcc ggc cga agt gct aga gga ggt tgc      384
Val Trp Gly Glu Ala Ala Val Ala Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350
```

<210> SEQ ID NO 54
<211> LENGTH: 352
<212> TYPE: PRT
<213> ORGANISM: Tomato golden mosaic virus

<400> SEQUENCE: 54

```
Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Ala Ala Val Ala Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350
```

<210> SEQ ID NO 55
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 RS-R125 (Ala1) mutant

<400> SEQUENCE: 55

```
atg cca tcg cat cca aaa cgg ttt caa ata aat gcc aaa aat tat ttt       48
```

-continued

```
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt gcg gcc gct gca gga ggt tgc      384
Val Trp Gly Glu Phe Gln Val Asp Gly Ala Ala Ala Ala Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
```

-continued

```
Lys Glu Glu Asn Thr Pro Leu Lys Asn Trp Thr Phe His Asn Ala Lys
            325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 56
<211> LENGTH: 352
<212> TYPE: PRT
<213> ORGANISM: Tomato golden mosaic virus

<400> SEQUENCE: 56

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Ala Ala Ala Ala Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
            325                 330                 335

Phe Val Phe Leu Asn Ser Pro Leu Tyr Gln Ser Ser Thr Gln Ser Ser
            340                 345                 350
```

```
<210> SEQ ID NO 57
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 QT130 (Ala2) mutant

<400> SEQUENCE: 57

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

gca gct agc aac gac gct gca gca gag gcg tta aat gct tct tcc aaa      432
Ala Ala Ser Asn Asp Ala Ala Ala Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270
```

```
aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 58
<211> LENGTH: 352
<212> TYPE: PRT
<213> ORGANISM: Tomato golden mosaic virus

<400> SEQUENCE: 58

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Ala Ala Ser Asn Asp Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270
```

```
Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 59
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 ND133 (Ala3) mutant

<400> SEQUENCE: 59

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct gcg gcc gct gca gca gag gcg tta aat gct tct tcc aaa      432
Gln Thr Ser Ala Ala Ala Ala Ala Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
```

```
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 60
<211> LENGTH: 352
<212> TYPE: PRT
<213> ORGANISM: Tomato golden mosaic virus

<400> SEQUENCE: 60

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Ala Ala Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
```

```
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 61
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 E--N140 (Ala4) mutant

<400> SEQUENCE: 61

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gcg gcc gcg tta gct gct tct tcc aaa      432
Gln Thr Ser Asn Asp Ala Ala Ala Ala Ala Leu Ala Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160
```

-continued

```
ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 62
<211> LENGTH: 352
<212> TYPE: PRT
<213> ORGANISM: Tomato golden mosaic virus

<400> SEQUENCE: 62

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125
```

```
Gln Thr Ser Asn Asp Ala Ala Ala Ala Ala Leu Ala Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 63
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 KEE146 (Ala5) mutant

<400> SEQUENCE: 63

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
```

-continued

```
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc gcg      432
Gln Thr Ser Asn Asp Ala Ala Ala Glu Ala Leu Asn Ala Ser Ser Ala
    130                 135                 140

gcc gca gcc ctg cag ata att aga gag aaa atc cca gaa aaa tat tta      480
Ala Ala Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350
```

<210> SEQ ID NO 64
<211> LENGTH: 352
<212> TYPE: PRT
<213> ORGANISM: Tomato golden mosaic virus

<400> SEQUENCE: 64

```
Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45
```

```
Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Ala
    130                 135                 140

Ala Ala Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 65
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 REK154 (Ala6) mutant

<400> SEQUENCE: 65

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45
```

```
aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctg cag ata att gcg gcc gca atc cca gaa aaa tat tta      480
Glu Glu Ala Leu Gln Ile Ile Ala Ala Ala Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350
```

<210> SEQ ID NO 66
<211> LENGTH: 352

<212> TYPE: PRT
<213> ORGANISM: Tomato golden mosaic virus

<400> SEQUENCE: 66

```
Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Ala Ala Ala Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350
```

<210> SEQ ID NO 67
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 EKY159 (Ala7) mutant -continued

```
<400> SEQUENCE: 67

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctg cag ata att aga gag aaa atc cca gcg gcc gct tta      480
Glu Glu Ala Leu Gln Ile Ile Arg Glu Lys Ile Pro Ala Ala Ala Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
```

```
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa      1008
Lys Glu Glu Asn Thr Pro Leu Lys Asn Trp Thr Phe His Asn Ala Lys
            325                 330                 335

ttc gtc ttc ctc aac tcc ccc ctc tat caa agc tca aca cag agc agc      1056
Phe Val Phe Leu Asn Ser Pro Leu Tyr Gln Ser Ser Thr Gln Ser Ser
            340                 345                 350


<210> SEQ ID NO 68
<211> LENGTH: 352
<212> TYPE: PRT
<213> ORGANISM: Tomato golden mosaic virus

<400> SEQUENCE: 68

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Arg Glu Lys Ile Pro Ala Ala Ala Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
```

```
                325                 330                 335

Phe Val Phe Leu Asn Ser Pro Leu Tyr Gln Ser Ser Thr Gln Ser Ser
            340                 345                 350


<210> SEQ ID NO 69
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 Q-HN165 (Ala8) mutant

<400> SEQUENCE: 69

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt gcg ttc gcc gct cta aat agc aat tta gat agg ata ttt gat aag      528
Phe Ala Phe Ala Ala Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255
```

```
gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 70
<211> LENGTH: 352
<212> TYPE: PRT
<213> ORGANISM: Tomato golden mosaic virus

<400> SEQUENCE: 70

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Ala Phe Ala Ala Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255
```

```
Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 71
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 N-DR172 (Ala9) mutant

<400> SEQUENCE: 71

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc gcg cta gct gcg ata ttt gat aag      528
Phe Gln Phe His Asn Leu Asn Ser Ala Leu Ala Ala Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
```

```
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 72
<211> LENGTH: 352
<212> TYPE: PRT
<213> ORGANISM: Tomato golden mosaic virus

<400> SEQUENCE: 72

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Ala Leu Ala Ala Ile Phe Asp Lys
                165                 170                 175
```

```
Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 73
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 K--E179 (Ala10) mutant

<400> SEQUENCE: 73

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140
```

```
gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat gcg      528
Phe Gln Phe His Asn Leu Asn Ser Asn Leu Asp Arg Ile Phe Asp Ala
                165                 170                 175

act ccg gcg cca tgg ctt cct ccg ttc cac gtc tca tca ttt act aac      576
Thr Pro Ala Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 74
<211> LENGTH: 352
<212> TYPE: PRT
<213> ORGANISM: Tomato golden mosaic virus

<400> SEQUENCE: 74

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
```

```
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Ala
                165                 170                 175

Thr Pro Ala Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 75
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 AAA136 (Leu) mutant

<400> SEQUENCE: 75

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
```

-continued

```
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac ctt cta cta gag gcc tta aat gct tct tcc aaa      432
Gln Thr Ser Asn Asp Leu Leu Leu Glu Ala Leu Asn Ala Ser Ser Lys
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 76
<211> LENGTH: 352
<212> TYPE: PRT
<213> ORGANISM: Tomato golden mosaic virus

<400> SEQUENCE: 76

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30
```

```
Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Leu Leu Leu Glu Ala Leu Asn Ala Ser Ser Lys
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 77
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 E--N140 + KEE146 (Ala4+5) mutant

<400> SEQUENCE: 77

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30
```

-continued

```
tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gcg gcc gcg tta gct gct tct tcc gcg      432
Gln Thr Ser Asn Asp Ala Ala Ala Ala Ala Leu Ala Ala Ser Ser Ala
    130                 135                 140

gcc gca gcc ctg cag ata att aga gag aaa atc cca gaa aaa tat tta      480
Ala Ala Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350
```

<210> SEQ ID NO 78
<211> LENGTH: 352
<212> TYPE: PRT
<213> ORGANISM: Tomato golden mosaic virus

<400> SEQUENCE: 78

Met Pro Ser His Pro Lys Arg Phe Gln Ile Asn Ala Lys Asn Tyr Phe
1 5 10 15

Leu Thr Tyr Pro Gln Cys Ser Leu Ser Lys Glu Glu Ser Leu Ser Gln
20 25 30

Leu Gln Ala Leu Asn Thr Pro Ile Asn Lys Lys Phe Ile Lys Ile Cys
35 40 45

Arg Glu Leu His Glu Asp Gly Gln Pro His Leu His Val Leu Ile Gln
50 55 60

Phe Glu Gly Lys Tyr Cys Cys Gln Asn Gln Arg Phe Phe Asp Leu Val
65 70 75 80

Ser Pro Thr Arg Ser Ala His Phe His Pro Asn Ile Gln Arg Ala Lys
85 90 95

Ser Ser Ser Asp Val Lys Thr Tyr Ile Asp Lys Asp Gly Asp Thr Leu
100 105 110

Val Trp Gly Glu Phe Gln Val Asp Gly Arg Ser Ala Arg Gly Gly Cys
115 120 125

Gln Thr Ser Asn Asp Ala Ala Ala Ala Ala Leu Ala Ala Ser Ser Ala
130 135 140

Ala Ala Ala Leu Gln Ile Ile Arg Glu Lys Ile Pro Glu Lys Tyr Leu
145 150 155 160

Phe Gln Phe His Asn Leu Asn Ser Asn Leu Asp Arg Ile Phe Asp Lys
165 170 175

Thr Pro Glu Pro Trp Leu Pro Pro Phe His Val Ser Ser Phe Thr Asn
180 185 190

Val Pro Asp Glu Met Arg Gln Trp Ala Glu Asn Tyr Phe Gly Lys Ser
195 200 205

Ser Ala Ala Arg Pro Glu Arg Pro Ile Ser Ile Ile Ile Glu Gly Asp
210 215 220

Ser Arg Thr Gly Lys Thr Met Trp Ala Arg Ser Leu Gly Pro His Asn
225 230 235 240

Tyr Leu Ser Gly His Leu Asp Leu Asn Ser Arg Val Tyr Ser Asn Lys
245 250 255

Val Glu Tyr Asn Val Ile Asp Asp Val Thr Pro Gln Tyr Leu Lys Leu
260 265 270

Lys His Trp Lys Glu Leu Ile Gly Ala Gln Arg Asp Trp Gln Thr Asn
275 280 285

Cys Lys Tyr Gly Lys Pro Val Gln Ile Lys Gly Gly Ile Pro Ser Ile
290 295 300

Val Leu Cys Asn Pro Gly Glu Gly Ala Ser Tyr Lys Val Phe Leu Asp
305 310 315 320

Lys Glu Glu Asn Thr Pro Leu Lys Asn Trp Thr Phe His Asn Ala Lys
325 330 335

Phe Val Phe Leu Asn Ser Pro Leu Tyr Gln Ser Ser Thr Gln Ser Ser
340 345 350

<210> SEQ ID NO 79
<211> LENGTH: 1056
<212> TYPE: DNA
<213> ORGANISM: Tomato golden mosaic virus

```
<220> FEATURE:
<221> NAME/KEY: CDS
<222> LOCATION: (1)..(1056)
<223> OTHER INFORMATION: TGMV AL1 K144 mutant

<400> SEQUENCE: 79

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc gcg      432
Gln Thr Ser Asn Asp Ala Ala Ala Glu Ala Leu Asn Ala Ser Ser Ala
    130                 135                 140

gaa gaa gcc ctg cag ata att aga gag aaa atc cca gaa aaa tat tta      480
Glu Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
```

-continued

```
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 80
<211> LENGTH: 352
<212> TYPE: PRT
<213> ORGANISM: Tomato golden mosaic virus

<400> SEQUENCE: 80

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Ala
    130                 135                 140

Glu Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300
```

```
Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 81
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 E145 mutant

<400> SEQUENCE: 81

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gca gag gcc ctg cag ata att aga gag aaa atc cca gaa aaa tat tta      480
Ala Glu Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240
```

-continued

```
tat ttg agc ggg cat ttg gat ctc aat tct agg gtt tac tca aac aag      768
Tyr Leu Ser Gly His Leu Asp Leu Asn Ser Arg Val Tyr Ser Asn Lys
            245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
            325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 82
<211> LENGTH: 352
<212> TYPE: PRT
<213> ORGANISM: Tomato golden mosaic virus

<400> SEQUENCE: 82

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Ala Glu Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
```

-continued

```
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 83
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 E146 mutant

<400> SEQUENCE: 83

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gca gcc ctg cag ata att aga gag aaa atc cca gaa aaa tat tta      480
Glu Ala Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
```

```
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
            245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
            325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 84
<211> LENGTH: 352
<212> TYPE: PRT
<213> ORGANISM: Tomato golden mosaic virus

<400> SEQUENCE: 84

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Ala Ala Leu Gln Ile Ile Arg Glu Lys Ile Pro Glu Lys Tyr Leu
145                 150                 155                 160
```

```
Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 85
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 EE146 mutant

<400> SEQUENCE: 85

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125
```

-continued

```
caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gcg gcc gcc ctg cag ata att aga gag aaa atc cca gaa aaa tat tta      480
Ala Ala Ala Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 86
<211> LENGTH: 352
<212> TYPE: PRT
<213> ORGANISM: Tomato golden mosaic virus

<400> SEQUENCE: 86

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80
```

```
Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Ala Ala Ala Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 87
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 A147Y mutant

<400> SEQUENCE: 87

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
```

```
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa tac ctt cag ata att aga gag aaa atc cca gaa aaa tat tta      480
Glu Glu Tyr Leu Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350
```

```
<210> SEQ ID NO 88
<211> LENGTH: 352
<212> TYPE: PRT
<213> ORGANISM: Tomato golden mosaic virus

<400> SEQUENCE: 88

Met Pro Ser His Pro Lys Arg Phe Gln Ile Asn Ala Lys Asn Tyr Phe
```

-continued

```
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Tyr Leu Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 89
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 L148 mutant

<400> SEQUENCE: 89

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15
```

-continued

```
ctt aca tat cct cag tgc tcc ttg tcc aaa gaa gaa tca ctt tct caa        96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc       144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag       192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta       240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa       288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt       336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc       384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa       432
Gln Thr Ser Asn Asp Ala Ala Ala Glu Ala Leu Asn Ala Ser Ser Lys
    130                 135                 140

gaa gaa gct gcg cag ata att aga gag aaa atc cca gaa aaa tat tta       480
Glu Glu Ala Ala Gln Ile Ile Arg Glu Lys Ile Pro Glu Lys Tyr Leu
145                 150                 155                 160

ttt cag ttc cac aat cta aat agc aat tta gat agg ata ttt gat aag       528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac       576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt       624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat       672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat       720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag       768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg       816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac       864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc       912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac       960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa      1008
Lys Glu Glu Asn Thr Pro Leu Lys Asn Trp Thr Phe His Asn Ala Lys
                325                 330                 335
```

```
ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350
```

<210> SEQ ID NO 90
<211> LENGTH: 352
<212> TYPE: PRT
<213> ORGANISM: Tomato golden mosaic virus

<400> SEQUENCE: 90

```
Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Ala Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350
```

```
<210> SEQ ID NO 91
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 L148V mutant

<400> SEQUENCE: 91

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gag gcc gtg cag ata att aga gag aaa atc cca gaa aaa tat tta      480
Glu Glu Ala Val Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
```

```
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 92
<211> LENGTH: 352
<212> TYPE: PRT
<213> ORGANISM: Tomato golden mosaic virus

<400> SEQUENCE: 92

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Val Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285
```

```
Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 93
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 L148V* mutant

<400> SEQUENCE: 93

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc gtt cag ata att aga gag aaa atc cca gaa aaa tat tta      480
Glu Glu Ala Val Gln Ile Ile Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220
```

-continued

```
agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 94
<211> LENGTH: 352
<212> TYPE: PRT
<213> ORGANISM: Tomato golden mosaic virus

<400> SEQUENCE: 94

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Val Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205
```

```
Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 95
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 L148G mutant

<400> SEQUENCE: 95

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110

gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ggc cag ata att aga gag aaa atc cca gaa aaa tat tta      480
Glu Glu Ala Gly Gln Ile Ile Arg Glu Lys Ile Pro Glu Lys Tyr Leu
145                 150                 155                 160

ttt cag ttc cac aat cta aat agc aat tta gat agg ata ttt gat aag      528
```

```
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350


<210> SEQ ID NO 96
<211> LENGTH: 352
<212> TYPE: PRT
<213> ORGANISM: Tomato golden mosaic virus

<400> SEQUENCE: 96

Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60

Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
```

```
    130                 135                 140

Glu Glu Ala Gly Gln Ile Ile Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350


<210> SEQ ID NO 97
<211> LENGTH: 1056
<212> TYPE: DNA
<213> ORGANISM: Tomato golden mosaic virus
<220> FEATURE:
<221> NAME/KEY: CDS
<222> LOCATION: (1)..(1056)
<223> OTHER INFORMATION: TGMV AL1 II151 mutant

<400> SEQUENCE: 97

atg cca tcg cat cca aaa cgg ttt caa ata aat gcc aaa aat tat ttt       48
Met Pro Ser His Pro Lys Arg Phe Gln Ile Asn Ala Lys Asn Tyr Phe
1               5                   10                  15

ctt aca tat cct cag tgc tcc ttg tcc aaa gaa gaa tca ctt tct caa       96
Leu Thr Tyr Pro Gln Cys Ser Leu Ser Lys Glu Glu Ser Leu Ser Gln
            20                  25                  30

tta caa gcc cta aac act ccg att aac aaa aaa ttc ata aaa atc tgc      144
Leu Gln Ala Leu Asn Thr Pro Ile Asn Lys Lys Phe Ile Lys Ile Cys
        35                  40                  45

aga gag ctt cat gaa gat ggg caa cct cac ctc cac gtg ctt att cag      192
Arg Glu Leu His Glu Asp Gly Gln Pro His Leu His Val Leu Ile Gln
    50                  55                  60

ttc gag gga aaa tac tgc tgc caa aat caa cga ttc ttc gac ctg gta      240
Phe Glu Gly Lys Tyr Cys Cys Gln Asn Gln Arg Phe Phe Asp Leu Val
65                  70                  75                  80

tcc cca aca agg tca gca cat ttc cat cca aac att cag aga gct aaa      288
Ser Pro Thr Arg Ser Ala His Phe His Pro Asn Ile Gln Arg Ala Lys
                85                  90                  95

tcg tct tcc gac gtc aag acg tac atc gac aaa gac gga gat act ctt      336
Ser Ser Ser Asp Val Lys Thr Tyr Ile Asp Lys Asp Gly Asp Thr Leu
            100                 105                 110
```

```
gta tgg gga gaa ttc cag gtc gac ggt cga agt gct aga gga ggt tgc      384
Val Trp Gly Glu Phe Gln Val Asp Gly Arg Ser Ala Arg Gly Gly Cys
        115                 120                 125

caa aca tct aac gac gct gca gca gag gcg tta aat gct tct tcc aaa      432
Gln Thr Ser Asn Asp Ala Ala Ala Glu Ala Leu Asn Ala Ser Ser Lys
    130                 135                 140

gaa gaa gcc ctt cag gca gct aga gag aaa atc cca gaa aaa tat tta      480
Glu Glu Ala Leu Gln Ala Ala Arg Glu Lys Ile Pro Glu Lys Tyr Leu
145                 150                 155                 160

ttt cag ttc cac aat cta aat agc aat tta gat agg ata ttt gat aag      528
Phe Gln Phe His Asn Leu Asn Ser Asn Leu Asp Arg Ile Phe Asp Lys
                165                 170                 175

act cct gaa cca tgg ctt cct ccg ttc cac gtc tca tca ttt act aac      576
Thr Pro Glu Pro Trp Leu Pro Pro Phe His Val Ser Ser Phe Thr Asn
            180                 185                 190

gtg cca gac gag atg aga caa tgg gct gaa aat tat ttt gga aag agt      624
Val Pro Asp Glu Met Arg Gln Trp Ala Glu Asn Tyr Phe Gly Lys Ser
        195                 200                 205

tcc gct gcg cgg ccg gag aga cct att agt att atc atc gag ggc gat      672
Ser Ala Ala Arg Pro Glu Arg Pro Ile Ser Ile Ile Ile Glu Gly Asp
    210                 215                 220

agt cgg acg gga aag act atg tgg gct cgt tca cta ggc cca cat aat      720
Ser Arg Thr Gly Lys Thr Met Trp Ala Arg Ser Leu Gly Pro His Asn
225                 230                 235                 240

tat ttg agc ggg cat ttg gat ctc aat tct agg gtt tac tca aac aag      768
Tyr Leu Ser Gly His Leu Asp Leu Asn Ser Arg Val Tyr Ser Asn Lys
                245                 250                 255

gtt gag tat aac gtc atc gat gat gtc aca ccg caa tat cta aag ttg      816
Val Glu Tyr Asn Val Ile Asp Asp Val Thr Pro Gln Tyr Leu Lys Leu
            260                 265                 270

aaa cat tgg aaa gaa ctc att ggg gcc caa aga gat tgg cag act aac      864
Lys His Trp Lys Glu Leu Ile Gly Ala Gln Arg Asp Trp Gln Thr Asn
        275                 280                 285

tgt aaa tac gga aag cca gtt caa att aaa gga ggt atc ccg tca atc      912
Cys Lys Tyr Gly Lys Pro Val Gln Ile Lys Gly Gly Ile Pro Ser Ile
    290                 295                 300

gtg ctg tgc aat cct gga gag ggt gct agc tat aaa gtt ttc ctc gac      960
Val Leu Cys Asn Pro Gly Glu Gly Ala Ser Tyr Lys Val Phe Leu Asp
305                 310                 315                 320

aaa gag gaa aac act cca cta aag aac tgg act ttc cat aat gcg aaa     1008
Lys Glu Glu Asn Thr Pro Leu Lys Asn Trp Thr Phe His Asn Ala Lys
                325                 330                 335

ttc gtc ttc ctc aac tcc ccc ctc tat caa agc tca aca cag agc agc     1056
Phe Val Phe Leu Asn Ser Pro Leu Tyr Gln Ser Ser Thr Gln Ser Ser
            340                 345                 350
```

<210> SEQ ID NO 98
<211> LENGTH: 352
<212> TYPE: PRT
<213> ORGANISM: Tomato golden mosaic virus

<400> SEQUENCE: 98

```
Met Pro Ser His Pro Lys Arg Phe Gln Ile Asn Ala Lys Asn Tyr Phe
1               5                   10                  15

Leu Thr Tyr Pro Gln Cys Ser Leu Ser Lys Glu Glu Ser Leu Ser Gln
            20                  25                  30

Leu Gln Ala Leu Asn Thr Pro Ile Asn Lys Lys Phe Ile Lys Ile Cys
        35                  40                  45

Arg Glu Leu His Glu Asp Gly Gln Pro His Leu His Val Leu Ile Gln
    50                  55                  60
```

```
Phe Glu Gly Lys Tyr Cys Cys Gln Asn Gln Arg Phe Phe Asp Leu Val
65                  70                  75                  80

Ser Pro Thr Arg Ser Ala His Phe His Pro Asn Ile Gln Arg Ala Lys
                85                  90                  95

Ser Ser Ser Asp Val Lys Thr Tyr Ile Asp Lys Asp Gly Asp Thr Leu
            100                 105                 110

Val Trp Gly Glu Phe Gln Val Asp Gly Arg Ser Ala Arg Gly Gly Cys
        115                 120                 125

Gln Thr Ser Asn Asp Ala Ala Ala Glu Ala Leu Asn Ala Ser Ser Lys
    130                 135                 140

Glu Glu Ala Leu Gln Ala Ala Arg Glu Lys Ile Pro Glu Lys Tyr Leu
145                 150                 155                 160

Phe Gln Phe His Asn Leu Asn Ser Asn Leu Asp Arg Ile Phe Asp Lys
                165                 170                 175

Thr Pro Glu Pro Trp Leu Pro Pro Phe His Val Ser Ser Phe Thr Asn
            180                 185                 190

Val Pro Asp Glu Met Arg Gln Trp Ala Glu Asn Tyr Phe Gly Lys Ser
        195                 200                 205

Ser Ala Ala Arg Pro Glu Arg Pro Ile Ser Ile Ile Ile Glu Gly Asp
    210                 215                 220

Ser Arg Thr Gly Lys Thr Met Trp Ala Arg Ser Leu Gly Pro His Asn
225                 230                 235                 240

Tyr Leu Ser Gly His Leu Asp Leu Asn Ser Arg Val Tyr Ser Asn Lys
                245                 250                 255

Val Glu Tyr Asn Val Ile Asp Asp Val Thr Pro Gln Tyr Leu Lys Leu
            260                 265                 270

Lys His Trp Lys Glu Leu Ile Gly Ala Gln Arg Asp Trp Gln Thr Asn
        275                 280                 285

Cys Lys Tyr Gly Lys Pro Val Gln Ile Lys Gly Gly Ile Pro Ser Ile
    290                 295                 300

Val Leu Cys Asn Pro Gly Glu Gly Ala Ser Tyr Lys Val Phe Leu Asp
305                 310                 315                 320

Lys Glu Glu Asn Thr Pro Leu Lys Asn Trp Thr Phe His Asn Ala Lys
                325                 330                 335

Phe Val Phe Leu Asn Ser Pro Leu Tyr Gln Ser Ser Thr Gln Ser Ser
            340                 345                 350
```

<210> SEQ ID NO 99
<211> LENGTH: 25
<212> TYPE: PRT
<213> ORGANISM: Tomato golden mosaic virus
<220> FEATURE:
<221> NAME/KEY: MISC_FEATURE
<222> LOCATION: (1)..(25)
<223> OTHER INFORMATION: Amino acids 132-156 of TGMV AL1

<400> SEQUENCE: 99

```
Asn Asp Ala Ala Ala Glu Ala Leu Asn Ala Ser Ser Lys Glu Glu Ala
1               5                   10                  15

Leu Gln Ile Ile Arg Glu Lys Ile Pro
            20                  25
```

<210> SEQ ID NO 100
<211> LENGTH: 13
<212> TYPE: PRT
<213> ORGANISM: Tomato golden mosaic virus
<220> FEATURE:
<221> NAME/KEY: MISC_FEATURE
<222> LOCATION: (1)..(13)
<223> OTHER INFORMATION: TGMV AL1 amino acids 144-156

<400> SEQUENCE: 100

Lys Glu Glu Ala Leu Gln Ile Ile Arg Glu Lys Ile Pro
1 5 10

<210> SEQ ID NO 101
<211> LENGTH: 13
<212> TYPE: PRT
<213> ORGANISM: tomato yellow leaf curl virus
<220> FEATURE:
<221> NAME/KEY: MISC_FEATURE
<222> LOCATION: (1)..(13)
<223> OTHER INFORMATION: TYLCV C1 amino acids 142-154

<400> SEQUENCE: 101

Lys Ser Glu Ala Leu Lys Ile Leu Arg Glu Leu Ala Pro
1 5 10

<210> SEQ ID NO 102
<211> LENGTH: 13
<212> TYPE: PRT
<213> ORGANISM: cabbage leaf curl virus
<220> FEATURE:
<221> NAME/KEY: MISC_FEATURE
<222> LOCATION: (1)..(13)
<223> OTHER INFORMATION: CbLCV AL1 amino acids 141-153

<400> SEQUENCE: 102

Val Glu Glu Ala Leu Ala Ile Ile Arg Ala Gly Asp Pro
1 5 10

<210> SEQ ID NO 103
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 103
ggacaccgat tggatccagc atgcctc 27

<210> SEQ ID NO 104
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 104
ccacagtcga attccccggg cttacgc 27

<210> SEQ ID NO 105
<211> LENGTH: 36
<212> TYPE: DNA
<213> ORGANISM: Artificial sequence
<220> FEATURE:
<223> OTHER INFORMATION: Mutagenesis oligonucleotide

<400> SEQUENCE: 105
cctaaataag atctacaagg atcccacgaa acccta 36

<210> SEQ ID NO 106
<211> LENGTH: 31
<212> TYPE: DNA
<213> ORGANISM: Artificial sequence
<220> FEATURE:

<223> OTHER INFORMATION: CbLCV AL1 L145A mutagenesis oligonucleotide

<400> SEQUENCE: 106
gtgtggaaga ggcggccgca attataaggg c 31

<210> SEQ ID NO 107
<211> LENGTH: 349
<212> TYPE: PRT
<213> ORGANISM: cabbage leaf curl virus

<400> SEQUENCE: 107

Met Pro Arg Asn Pro Lys Ser Phe Arg Leu Ala Ala Arg Asn Ile Phe
1 5 10 15

Leu Thr Tyr Pro Gln Cys Asp Ile Pro Lys Asp Glu Ala Leu Gln Met
20 25 30

Leu Gln Thr Leu Ser Trp Ser Val Val Lys Pro Thr Tyr Ile Arg Val
35 40 45

Ala Arg Glu Glu His Ser Asp Gly Phe Pro His Leu His Cys Leu Ile
50 55 60

Gln Leu Ser Gly Lys Ser Asn Ile Lys Asp Ala Arg Phe Phe Asp Ile
65 70 75 80

Thr His Pro Arg Arg Ser Ala Asn Phe His Pro Asn Ile Gln Ala Ala
85 90 95

Lys Asp Thr Asn Ala Val Lys Asn Tyr Ile Thr Lys Asp Gly Asp Tyr
100 105 110

Cys Glu Ser Gly Gln Tyr Lys Val Ser Gly Gly Thr Lys Ala Asn Lys
115 120 125

Asp Asp Val Tyr His Asn Ala Val Asn Ala Gly Cys Val Glu Glu Ala
130 135 140

Leu Ala Ile Ile Arg Ala Gly Asp Pro Lys Thr Phe Ile Val Ser Tyr
145 150 155 160

His Asn Val Arg Ala Asn Ile Glu Arg Leu Phe Thr Lys Ala Pro Glu
165 170 175

Pro Trp Ala Pro Pro Phe Gln Leu Ser Ser Phe Thr Asn Val Pro Asp
180 185 190

Glu Met Ser Ser Trp Ala Asp Asp Tyr Phe Gly Arg Ser Ala Ala Ala
195 200 205

Arg Ala Glu Arg Pro Ile Ser Ile Ile Val Glu Gly Asp Ser Arg Thr
210 215 220

Gly Lys Thr Met Trp Ala Arg Ala Leu Gly Pro His Asn Tyr Leu Ser
225 230 235 240

Gly His Leu Asp Phe Asn Ser Lys Val Phe Ser Asn Asn Ala Glu Tyr
245 250 255

Asn Val Ile Asp Asp Ile Ala Pro His Tyr Leu Lys Leu Lys His Trp
260 265 270

Lys Glu Leu Ile Gly Ala Gln Arg Asp Trp Gln Ser Asn Cys Lys Tyr
275 280 285

Gly Lys Pro Val Gln Ile Lys Gly Gly Ile Pro Ser Ile Val Leu Cys
290 295 300

Asn Pro Gly Glu Gly Ser Ser Tyr Ile Ser Phe Leu Asn Lys Glu Glu
305 310 315 320

Asn Ala Ser Leu Arg Ala Trp Thr Thr Lys Asn Ala Lys Phe Ile Thr
325 330 335

Leu Glu Ala Pro Leu Tyr Gln Ser Thr Ala Gln Asp Cys
340 345

<210> SEQ ID NO 108
<211> LENGTH: 70
<212> TYPE: PRT
<213> ORGANISM: cabbage leaf curl virus
<220> FEATURE:
<221> NAME/KEY: MISC_FEATURE
<222> LOCATION: (1)..(70)
<223> OTHER INFORMATION: Wild-type CbLCV AL1 amino acids 111-180

<400> SEQUENCE: 108

```
Asp Tyr Cys Glu Ser Gly Gln Tyr Lys Val Ser Gly Gly Thr Lys Ala
1               5                   10                  15

Asn Lys Asp Asp Val Tyr His Asn Ala Val Asn Ala Gly Cys Val Glu
            20                  25                  30

Glu Ala Leu Ala Ile Ile Arg Ala Gly Asp Pro Lys Thr Phe Ile Val
        35                  40                  45

Ser Tyr His Asn Val Arg Ala Asn Ile Glu Arg Leu Phe Thr Lys Ala
    50                  55                  60

Pro Glu Pro Trp Ala Pro
65                  70
```

<210> SEQ ID NO 109
<211> LENGTH: 70
<212> TYPE: PRT
<213> ORGANISM: cabbage leaf curl virus
<220> FEATURE:
<221> NAME/KEY: MISC_FEATURE
<222> LOCATION: (35)..(35)
<223> OTHER INFORMATION: L145A mutation

<400> SEQUENCE: 109

```
Asp Tyr Cys Glu Ser Gly Gln Tyr Lys Val Ser Gly Gly Thr Lys Ala
1               5                   10                  15

Asn Lys Asp Asp Val Tyr His Asn Ala Val Asn Ala Gly Cys Val Glu
            20                  25                  30

Glu Ala Ala Ala Ile Ile Arg Ala Gly Asp Pro Lys Thr Phe Ile Val
        35                  40                  45

Ser Tyr His Asn Val Arg Ala Asn Ile Glu Arg Leu Phe Thr Lys Ala
    50                  55                  60

Pro Glu Pro Trp Ala Pro
65                  70
```

<210> SEQ ID NO 110
<211> LENGTH: 1047
<212> TYPE: DNA
<213> ORGANISM: cabbage leaf curl virus
<220> FEATURE:
<221> NAME/KEY: misc_feature
<222> LOCATION: (1)..(1047)
<223> OTHER INFORMATION: CbLCV AL1 coding sequence

<400> SEQUENCE: 110

```
atgccacgaa accctaaatc gtttcgttta gcagcccgaa atatattctt aacatatccc      60

cagtgcgaca tacccaaaga tgaagctctt cagatgcttc aaaccctgtc gtggtcagtc     120

gtcaaaccca catacatcag agtcgcaaga gaggaacatt cagacgggtt cccccattta     180

cactgtctca tccaactatc aggaaagtcg aacatcaagg atgctagatt tttcgacatc     240

actcacccca gaaggtctgc caattttcac ccaaacattc aggcagccaa agacaccaat     300

gccgtcaaga attacatcac caaagatggt gattattgtg aatccgggca gtacaaggtg     360

tctgggggta caaaggcaaa taaagacgac gtctaccaca acgccgtcaa tgcgggatgt     420
```

gtggaagagg ctctcgcaat tataagggct ggagatccaa agacgttcat tgttagttat 480
cataatgtta gagctaacat agagcgactc tttactaagg ctccggaacc atgggctcct 540
ccgtttcaac tctcctcctt tactaacgtc ccggacgaga tgagttcatg ggcagatgac 600
tattttggtc ggagtgccgc tgcgcgggcg gaaagaccta ttagtatcat agttgaaggt 660
gattcacgaa ccggcaagac catgtgggcg cgtgctttag gaccacataa ttatttgagt 720
gggcacctcg actttaattc aaaggtcttt tcaaataatg cggagtataa cgtcattgat 780
gacatagctc cgcattatct aaagctaaag cactggaaag agcttattgg ggcccaaagg 840
gactggcaat caaactgtaa gtacggcaag ccagttcaaa ttaaaggtgg cataccctca 900
atcgtgctgt gcaatccagg agaggggagc agttatataa gtttcctcaa caaagaggaa 960
aatgcatcac taagagcgtg gactaccaaa aatgcaaaat tcatcactct tgaagccccc 1020
ctctatcaaa gcacagcaca agattgc 1047

<210> SEQ ID NO 111
<211> LENGTH: 1047
<212> TYPE: DNA
<213> ORGANISM: cabbage leaf curl virus
<220> FEATURE:
<221> NAME/KEY: CDS
<222> LOCATION: (1)..(1047)
<223> OTHER INFORMATION: CbLCV AL1 L145A mutation

<400> SEQUENCE: 111 atg cca cga aac cct aaa tcg ttt cgt tta gca gcc cga aat ata ttc 48
Met Pro Arg Asn Pro Lys Ser Phe Arg Leu Ala Ala Arg Asn Ile Phe
1 5 10 15 tta aca tat ccc cag tgc gac ata ccc aaa gat gaa gct ctt cag atg 96
Leu Thr Tyr Pro Gln Cys Asp Ile Pro Lys Asp Glu Ala Leu Gln Met
20 25 30 ctt caa acc ctg tcg tgg tca gtc gtc aaa ccc aca tac atc aga gtc 144
Leu Gln Thr Leu Ser Trp Ser Val Val Lys Pro Thr Tyr Ile Arg Val
35 40 45 gca aga gag gaa cat tca gac ggg ttc ccc cat tta cac tgt ctc atc 192
Ala Arg Glu Glu His Ser Asp Gly Phe Pro His Leu His Cys Leu Ile
50 55 60 caa cta tca gga aag tcg aac atc aag gat gct aga ttt ttc gac atc 240
Gln Leu Ser Gly Lys Ser Asn Ile Lys Asp Ala Arg Phe Phe Asp Ile
65 70 75 80 act cac ccc aga agg tct gcc aat ttt cac cca aac att cag gca gcc 288
Thr His Pro Arg Arg Ser Ala Asn Phe His Pro Asn Ile Gln Ala Ala
85 90 95 aaa gac acc aat gcc gtc aag aat tac atc acc aaa gat ggt gat tat 336
Lys Asp Thr Asn Ala Val Lys Asn Tyr Ile Thr Lys Asp Gly Asp Tyr
100 105 110 tgt gaa tcc ggg cag tac aag gtg tct ggg ggt aca aag gca aat aaa 384
Cys Glu Ser Gly Gln Tyr Lys Val Ser Gly Gly Thr Lys Ala Asn Lys
115 120 125 gac gac gtc tac cac aac gcc gtc aat gcg gga tgt gtg gaa gag gcg 432
Asp Asp Val Tyr His Asn Ala Val Asn Ala Gly Cys Val Glu Glu Ala
130 135 140 gcc gca att ata agg gct gga gat cca aag acg ttc att gtt agt tat 480
Ala Ala Ile Ile Arg Ala Gly Asp Pro Lys Thr Phe Ile Val Ser Tyr
145 150 155 160 cat aat gtt aga gct aac ata gag cga ctc ttt act aag gct ccg gaa 528
His Asn Val Arg Ala Asn Ile Glu Arg Leu Phe Thr Lys Ala Pro Glu
165 170 175 cca tgg gct cct ccg ttt caa ctc tcc tcc ttt act aac gtc ccg gac 576
Pro Trp Ala Pro Pro Phe Gln Leu Ser Ser Phe Thr Asn Val Pro Asp

```
            180                 185                 190

gag atg agt tca tgg gca gat gac tat ttt ggt cgg agt gcc gct gcg      624
Glu Met Ser Ser Trp Ala Asp Asp Tyr Phe Gly Arg Ser Ala Ala Ala
        195                 200                 205

cgg gcg gaa aga cct att agt atc ata gtt gaa ggt gat tca cga acc      672
Arg Ala Glu Arg Pro Ile Ser Ile Ile Val Glu Gly Asp Ser Arg Thr
    210                 215                 220

ggc aag acc atg tgg gcg cgt gct tta gga cca cat aat tat ttg agt      720
Gly Lys Thr Met Trp Ala Arg Ala Leu Gly Pro His Asn Tyr Leu Ser
225                 230                 235                 240

ggg cac ctc gac ttt aat tca aag gtc ttt tca aat aat gcg gag tat      768
Gly His Leu Asp Phe Asn Ser Lys Val Phe Ser Asn Asn Ala Glu Tyr
                245                 250                 255

aac gtc att gat gac ata gct ccg cat tat cta aag cta aag cac tgg      816
Asn Val Ile Asp Asp Ile Ala Pro His Tyr Leu Lys Leu Lys His Trp
            260                 265                 270

aaa gag ctt att ggg gcc caa agg gac tgg caa tca aac tgt aag tac      864
Lys Glu Leu Ile Gly Ala Gln Arg Asp Trp Gln Ser Asn Cys Lys Tyr
        275                 280                 285

ggc aag cca gtt caa att aaa ggt ggc ata ccc tca atc gtg ctg tgc      912
Gly Lys Pro Val Gln Ile Lys Gly Gly Ile Pro Ser Ile Val Leu Cys
    290                 295                 300

aat cca gga gag ggg agc agt tat ata agt ttc ctc aac aaa gag gaa      960
Asn Pro Gly Glu Gly Ser Ser Tyr Ile Ser Phe Leu Asn Lys Glu Glu
305                 310                 315                 320

aat gca tca cta aga gcg tgg act acc aaa aat gca aaa ttc atc act     1008
Asn Ala Ser Leu Arg Ala Trp Thr Thr Lys Asn Ala Lys Phe Ile Thr
                325                 330                 335

ctt gaa gcc ccc ctc tat caa agc aca gca caa gat tgc                 1047
Leu Glu Ala Pro Leu Tyr Gln Ser Thr Ala Gln Asp Cys
            340                 345


<210> SEQ ID NO 112
<211> LENGTH: 349
<212> TYPE: PRT
<213> ORGANISM: cabbage leaf curl virus

<400> SEQUENCE: 112

Met Pro Arg Asn Pro Lys Ser Phe Arg Leu Ala Ala Arg Asn Ile Phe
1               5                   10                  15

Leu Thr Tyr Pro Gln Cys Asp Ile Pro Lys Asp Glu Ala Leu Gln Met
            20                  25                  30

Leu Gln Thr Leu Ser Trp Ser Val Val Lys Pro Thr Tyr Ile Arg Val
        35                  40                  45

Ala Arg Glu Glu His Ser Asp Gly Phe Pro His Leu His Cys Leu Ile
    50                  55                  60

Gln Leu Ser Gly Lys Ser Asn Ile Lys Asp Ala Arg Phe Phe Asp Ile
65                  70                  75                  80

Thr His Pro Arg Arg Ser Ala Asn Phe His Pro Asn Ile Gln Ala Ala
                85                  90                  95

Lys Asp Thr Asn Ala Val Lys Asn Tyr Ile Thr Lys Asp Gly Asp Tyr
            100                 105                 110

Cys Glu Ser Gly Gln Tyr Lys Val Ser Gly Gly Thr Lys Ala Asn Lys
        115                 120                 125

Asp Asp Val Tyr His Asn Ala Val Asn Ala Gly Cys Val Glu Glu Ala
    130                 135                 140
```

```
Ala Ala Ile Ile Arg Ala Gly Asp Pro Lys Thr Phe Ile Val Ser Tyr
145                 150                 155                 160

His Asn Val Arg Ala Asn Ile Glu Arg Leu Phe Thr Lys Ala Pro Glu
                165                 170                 175

Pro Trp Ala Pro Pro Phe Gln Leu Ser Ser Phe Thr Asn Val Pro Asp
            180                 185                 190

Glu Met Ser Ser Trp Ala Asp Asp Tyr Phe Gly Arg Ser Ala Ala Ala
        195                 200                 205

Arg Ala Glu Arg Pro Ile Ser Ile Ile Val Glu Gly Asp Ser Arg Thr
    210                 215                 220

Gly Lys Thr Met Trp Ala Arg Ala Leu Gly Pro His Asn Tyr Leu Ser
225                 230                 235                 240

Gly His Leu Asp Phe Asn Ser Lys Val Phe Ser Asn Asn Ala Glu Tyr
                245                 250                 255

Asn Val Ile Asp Asp Ile Ala Pro His Tyr Leu Lys Leu Lys His Trp
            260                 265                 270

Lys Glu Leu Ile Gly Ala Gln Arg Asp Trp Gln Ser Asn Cys Lys Tyr
        275                 280                 285

Gly Lys Pro Val Gln Ile Lys Gly Gly Ile Pro Ser Ile Val Leu Cys
    290                 295                 300

Asn Pro Gly Glu Gly Ser Ser Tyr Ile Ser Phe Leu Asn Lys Glu Glu
305                 310                 315                 320

Asn Ala Ser Leu Arg Ala Trp Thr Thr Lys Asn Ala Lys Phe Ile Thr
                325                 330                 335

Leu Glu Ala Pro Leu Tyr Gln Ser Thr Ala Gln Asp Cys
            340                 345
```

<210> SEQ ID NO 113
<211> LENGTH: 13
<212> TYPE: PRT
<213> ORGANISM: Artificial
<220> FEATURE:
<223> OTHER INFORMATION: Consensus begomovirus AL1/C1 sequence
<220> FEATURE:
<221> NAME/KEY: MISC_FEATURE
<222> LOCATION: (1)..(3)
<223> OTHER INFORMATION: Xaa can be any naturally occurring amino acid, but is generally a charged amino acid which is optionally present or absent
<220> FEATURE:
<221> NAME/KEY: MISC_FEATURE
<222> LOCATION: (5)..(5)
<223> OTHER INFORMATION: Xaa can be Leu or Met
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be Ile or Val
<220> FEATURE:
<221> NAME/KEY: MISC_FEATURE
<222> LOCATION: (8)..(8)
<223> OTHER INFORMATION: Xaa can be Ile or Leu
<220> FEATURE:
<221> NAME/KEY: MISC_FEATURE
<222> LOCATION: (9)..(9)
<223> OTHER INFORMATION: Xaa can be Arg or Lys
<220> FEATURE:
<221> NAME/KEY: MISC_FEATURE
<222> LOCATION: (10)..(10)
<223> OTHER INFORMATION: Xaa can be Glu or Asp -continued

```
<220> FEATURE:
<221> NAME/KEY: misc_feature
<222> LOCATION: (11)..(12)
<223> OTHER INFORMATION: Xaa can be any naturally occurring amino acid

<400> SEQUENCE: 113

Xaa Xaa Xaa Ala Xaa Xaa Xaa Xaa Xaa Xaa Xaa Xaa Pro
1               5                   10
```